United States Patent
Lancaster

(10) Patent No.: US 11,282,088 B1
(45) Date of Patent: *Mar. 22, 2022

(54) BUSINESS METHODS AND SYSTEMS FOR OFFERING AND OBTAINING RESEARCH SERVICES

(71) Applicant: James Justin Lancaster, Winchester, MA (US)

(72) Inventor: James Justin Lancaster, Winchester, MA (US)

(*) Notice: Subject to any disclaimer, the term of this patent is extended or adjusted under 35 U.S.C. 154(b) by 134 days.

This patent is subject to a terminal disclaimer.

(21) Appl. No.: 16/383,605

(22) Filed: Apr. 13, 2019

Related U.S. Application Data

(60) Division of application No. 13/351,210, filed on Jan. 16, 2012, now Pat. No. 10,311,442, which is a
(Continued)

(51) Int. Cl.
*G06Q 30/00* (2012.01)
*G16H 15/00* (2018.01)
(Continued)

(52) U.S. Cl.
CPC .......... *G06Q 30/00* (2013.01); *G06Q 10/083* (2013.01); *G06Q 50/22* (2013.01); *G16H 10/00* (2018.01); *G16H 10/40* (2018.01); *G16H 15/00* (2018.01)

(58) Field of Classification Search
CPC ...... G06Q 30/00; G06Q 50/22; G06Q 10/083; G16H 10/40; G16H 10/00; G16H 15/00
See application file for complete search history.

(56) References Cited

U.S. PATENT DOCUMENTS

| 2004/0267562 A1* | 12/2004 | Fuhrer | G16H 10/40 705/2 |
| 2005/0165594 A1* | 7/2005 | Chandra | G16B 5/00 703/11 |

(Continued)

FOREIGN PATENT DOCUMENTS

| WO | WO-2005073893 A2 * | 8/2005 | ............. G06Q 10/06 |
| WO | WO-2005073893 A3 * | 1/2006 | ............. G16B 50/00 |

OTHER PUBLICATIONS

5 Top Medical Product Manufacturers Create Internet Transaction Site, Mar. 31, 2000, Biomedical Market Newsletter, vol. 10, Issue. 3. (Year: 2000).*

Salazar et al., The Strategic Impact of Internet Technology in Biotechnology and Pharmaceutical Firms: Insights from a Knowledge Management Perspective, Apr.-Jul. 2003, Information Technology and Management, pp. 289-301. (Year: 2003).*

*Primary Examiner* — Christopher L Gilligan

(57) ABSTRACT

Systems and methods that provide for automation-assisted research into the workings of one or more studied systems include software modules that communicate with domain knowledge bases, research professionals, automated laboratories, research service objects, and data analysis processes. When implemented in conjunction with online business methods and systems, ordering processes can interface directly with research services, such as medical research services and biomedical research services. In some implementations, automatically selected research service objects can correspond to 3rd-party research services that can produce research results, and subsequent data-processing can update the knowledge bases and provide guidance to a next phase of research.

9 Claims, 39 Drawing Sheets

Related U.S. Application Data continuation-in-part of application No. 12/290,731, filed on Nov. 3, 2008, now abandoned, and a continuation-in-part of application No. 12/009,793, filed on Jan. 22, 2008, now Pat. No. 8,099,297.

(60) Provisional application No. 60/881,638, filed on Jan. 22, 2007, provisional application No. 60/985,160, filed on Nov. 2, 2007.

(51) Int. Cl.
*G16H 10/40* (2018.01)
*G06Q 10/08* (2012.01)
*G06Q 50/22* (2018.01)
*G16H 10/00* (2018.01)

(56) References Cited

U.S. PATENT DOCUMENTS

| | | | | |
|---|---|---|---|---|
| 2005/0266494 A1* | 12/2005 | Hodge | G06Q 30/00 | 435/6.12 |
| 2006/0161472 A1* | 7/2006 | Weild, IV | G06Q 40/00 | 705/1.1 |
| 2007/0203747 A1* | 8/2007 | Baharloo | G06Q 10/10 | 705/2 |
| 2009/0099868 A1* | 4/2009 | Lustig | G16H 10/40 | 705/2 |
| 2009/0192854 A1* | 7/2009 | Pietrucha, Jr. | G06Q 30/06 | 705/56 |

* cited by examiner

BUSINESS METHODS AND SYSTEMS FOR OFFERING AND OBTAINING RESEARCH SERVICES

CROSS-REFERENCE TO RELATED APPLICATIONS

Pursuant to 35 U.S.C. § 121, § 1.53(b)(1), and § 1.78(a)(1), this application is a divisional application continuing from an unpublished U.S. patent application Ser. No. 13/351,210, filed Jan. 16, 2012, (and see U.S. patent Ser. No. 10/311,442 b1, issue date Jun. 4, 2019), said prior application being a continuation-in-part (C-I-P) application claiming benefit of non-provisional parent application, U.S. patent application Ser. No. 12/009,793, filed Jan. 22, 2008 (US Publication No. 20080215364-A1; Publication date Sep. 4, 2008; now U.S. Pat. No. 8,099,297, issued Jan. 17, 2012), which application claims priority from U.S. Provisional Application No. 60881638, filed 1/2212007, which parent and provisional applications are, hereby, incorporated by reference herein in their entirety, and the prior CIP application further claiming benefit of non-provisional parent application, U.S. Pat. No. 12,290,731, filed Mar. 11, 2008 (US Publication No. 20090138415-A1; Publication date May 28, 2009), which application claims priority from U.S. Provisional Application No. 60/985,160, filed Nov. 2, 2007, which parent and provisional applications are, hereby, incorporated by reference herein in their entirety. Reference is also made to related U.S. Pat. No. 8,571,887 (see U.S. patent application Ser. No. 13/339,370, filed Dec. 28, 2011, being a divisional from U.S. patent application Ser. No. 12/009, 793, above).

FIELD OF THE INVENTION

The invention described herein relates generally to the field of online business methods and systems for supporting, inter alia, the offering of, searching for, selection of and purchase of research services applicable to a system domain under study. Such systems can include, inter alia, biological, environmental, and other energetic systems. Research services can include, inter alia, biomedical.

BACKGROUND

Research into biological systems is moving from manual experimental techniques to robotics, and toward automated fluorescent detection in high throughput and/or high content screening. Continuing improvements in automation and data processing are useful and important. Specific advanced software technologies within the bioinformatics industry, particularly association mining, reverse engineering, knowledge assembly and simulation components, have enhanced computational biology to create new capabilities that are needed to improve and accelerate biomedical research.

As shown in FIG. 1, it has been understood for more than fifteen years that likely consequences of global warming will impose damages through storms, storm surge, erosion, flooding, disease vectors, sea-level rise and impacts upon domestic water, among other impacts. Uncertainty in measurement and modeling, variability in human perception of risk, and avoiding costs of precautionary measures all played together to leave the city vulnerable.

In U.S. Pat. No. 6,448,983, issued Sep. 10, 2002, incorporated herein by reference in its entirety, Ali et al. disclose a method for assisting a user in selecting an experimental design by obtaining attributes associated with a many experimental designs. Wang et al. have previously disclosed a computer-implemented method of designing a set of experiments to be performed with a set of resources (U.S. Pat. No. 6,996,550, issued Feb. 7, 2006, incorporated by reference herein in its entirety). D. R. Dorsett has described a computer-implemented method for processing experimental data according to an object model (U.S. Pat. No. 7,213,034, issued May 1, 2007, incorporated by reference herein in its entirety). L. B. Hales et al. have disclosed process control optimization systems that use adaptive optimization software with goal-seeking intelligent software objects (U.S. Pat. No. 6,112,126, issued Aug. 29, 2000, incorporated by reference herein in its entirety). Bondarenko has described a system that digitally represents an experiment design with a definition that provides the logical structure for data analysis of scans from one or more biological experiments (U.S. Pat. No. 7,269,517, issued Sep. 11, 2007, incorporated by reference herein in its entirety). Lorenzen et al. disclosed an expert system for the design and analysis of experiments that includes a descriptive mathematical model of the experiment under consideration yielding tests that supply information for comparing different designs and choosing the best possible design, providing a layout for data collection of data, and the system Once the data has been collected and entered, the system analyzes and interprets the results. (U.S. Pat. No. 5,253,331, issued Oct. 12, 1993, incorporated by reference herein in its entirety).

U.S. Pat. No. 6,615,157 issued to Tsai on Sep. 2, 2003, herein incorporated by reference in its entirety, discloses a system and method and computer program product for automatically assessing experiment results obtained in a process by analyzing attributes representing experimental results of a process. A method and system for managing and evaluating life science data is described in U.S. patent application Ser. No. 10/644,582 (D. N. Chandra, et al., filed Aug. 20, 2003), incorporated herein by reference in its entirety, where life science data is placed in a knowledge base and used for creating a knowledge base. U.S. patent application Ser. No. 10/992,973 (D. N. Chandra, et al., published Jul. 28, 2005), incorporated herein by reference in its entirety, includes methods for performing logical simulations within a biological knowledge base, including backward logical simulations. U.S. patent application Ser. No. 10/717,224 (D. N. Chandra et al.), which is incorporated herein by reference in its entirety, discloses a system that uses an epistemic engine that accepts biological data from real or thought experiments probing a biological system, and uses these data to produce a network model of component interactions consistent with the data and prior knowledge about the system, and thereby 'deconstructs biological reality and proposes testable hypotheses/explanations/models of the system operation. U.S. Pat. No. 7,415,359 issued Aug. 19, 2008 to Hill et al., which is incorporated herein by reference in its entirety, discloses systems and methods for cell simulation and cell-state prediction, where a cellular network can be simulated by representing interrelationships with equations solved to simulate a first state of the cell, then perturbing the network mathematically to simulate a second state of the cell which, upon comparison to the first state, identifies components as targets. U.S. patent application Ser. No. 11/985,618 by Hill et al. (Filed Nov. 15, 2007; Publ. No. 20080208784, Published Aug. 28, 2008), which is incorporated herein by reference in its entirety, discloses using a probabilistic modeling framework for reverse engineering an ensemble of causal models from data, pertaining to numerous types of systems, and then forward simulating the ensemble of models to analyze and predict the behavior of the network. Hood et al. (U.S. patent application Ser. No. 09/993,312, incorporated herein by reference in its entirety) disclose methods of predicting a behavior of a biochemical system by comparing data integration maps of the system under different conditions, comprising at least two networks, and identifying correlative changes in value sets between the maps to predict behavior of the system. U.S. Pat. No. 6,493,637 issued to Steeg on Dec. 10, 2002, which is incorporated herein by reference in its entirety, discloses a method and system for detecting coincidences in a data set of objects (See also Evan W. Steeg, Derek A. Robinson, Ed Willis: Coincidence Detection: A Fast Method for Discovering Higher-Order Correlations in Multidimensional Data. KDD 1998: 112-120; incorporated herein by reference in its entirety).

U.S. Pat. No. 5,384,895 to Rogers et al. (issued Jan. 24, 1995), which is incorporated herein by reference in its entirety, describes a self-organizing neural network and method for classifying a pattern signature having N-features where the network provides a posteriori conditional class probability that the pattern signature belongs to a selected class from a plurality of classes with which the neural network was trained. U.S. patent application Ser. No. 11/668,671 to Shaw, filed Jan. 30, 2007 and incorporated herein by reference in its entirety, discloses a computational method of determining a set of proposed pharmacophore features describing interactions between a known biological target and ligands showing activity towards the target by identifying a set of n-dimensional inter-site distance (ISD) vectors.

There is a continuing need to improve the conduct and data processing aspects of research into complex systems. Particularly, there is a need to improve access to automated experimentation in order to accelerate the pace of productive research. It is a further goal to provide a business method and system that employs computerized, automated steps and standardization at numerous points in the process of providing a medical or biomedical service.

SUMMARY

The invention provides for automated research systems and automated research methods, useful for studying systems, particularly complex systems. More specifically, the invention generally includes a method and system for detecting, monitoring, modeling and managing systemic function in complex biological and social systems, including, for example, without limitation, a method and system for finding cures for diseases in humans. Further, the invention provides a method and system for finding cures for diseases, including hardware, software and material inputs, and including automated experimental process connected to an analysis and modeling component, coupled with a management and query component, and further including a business method for implementing the research method and system in the marketplace with business partners and with customers.

The invention provides further for an automated biological research system (ABRS), comprised of multiple hardware and software components connected in such combination and sequence that (i) a connected series/set of research steps is automated to accelerate a goal-directed, search-function-based, iterative experimental cycle, (ii) complete functionality for each of the connected series/set of research steps is included, and (iii) these steps provide an iterative, looping-cycle, learning process that seeks the research goal and stops when the research goal is met.

An embodiment of the invention provides a system that facilitates management of a biotechnology and/or biomedical research process, comprising: a research component in communication with the biotechnology and/or biomedical research process which operates according to conditions of the process, which research component at least one of monitors and controls the process using modularized code; a standards-based model employed to modularize control code into testable blocks such that higher order modules are built from tested, approved modules; and a rules engine component that processes one or more rules in association with the modularized code to affect conditions of the process in real time. Further the system can have modularized code for development according to an International Standards for Automation (ISA) S88.01 standard. The invention further provides wherein the research component includes a process control component that interfaces to the process and associated equipment for control thereof according to conditions of the process, wherein the research component includes a data acquisition component that interfaces to the process and associated equipment for the measurement of data, and wherein the rules engine processes a prompt received from the research component in accordance with the one or more rules. An embodiment can provide for the rules engine to process the one or more rules to prioritize resource utilization as requested by the research component.

An embodiment further provides for a method for automating research of a studied system comprising the steps of providing an automated research system having at least one computer software module, a database component for holding a Library of Possible Experiments (LOPE) that contains at least two Experiment Objects (EOs), an Experiment Director (ExpDir) Module, a user interface, a computer, a data processing module, an experimental result analysis module, a database object for holding at least one first studied-system knowledge model ($SSKM_1$) (or knowledge-base assembly), a research progress evaluation module (RPEM), a module for (i) comparing results to said first studied system knowledge model ($SSKM_1$), (ii) updating $SSKM_1$ to a second SSKM ($SSKM_2$), and (iii) comparing $SSKM_2$ and $SSKM_1$ to evaluate an increase in value-of-information (VOI) against a prior research goal; and further providing at least a first studied system, providing at least two EOs, providing a research goal via the user-specified goal (USG), causing the ExpDir to evaluate the $SSKM_1$ against the USG to yield an information gap analysis result, passing the information gap result to the congruence module to analyze the highest probability path to reduce the gap, producing a result out that translates into 'info needed', passing the 'info-needed' descriptor to an Experiment Chooser (ExpChooser), with ExpChooser having access to the LOPE, yielding choice of at least one Experiment Object (EO) passing the chosen EO to Experiment Director Module (ExpDir) to direct at least one laboratory to process the experiment, the lab running the experiment to yield parameter results, passing the results to a data processing engine/module, and passing the processed data to the research progress evaluation module (RPEM) and/or Modeling module and Congruence Module (CM)), updating the SSKM index n+1 and looping again unless the 'info-needed' gap is zero and if the gap is zero, then stop.

The invention provides for an automated research system comprising: a processor; a memory storing instructions adapted to be executed by the processor to receive an 'experiment directive' indication to run an experiment; receive an 'experiment-run' command to run the experiment, the command being a permitted experiment; determine whether said permitted experiment is proprietary as to subject-matter or procedure or other parameter; and run the experiment defined by the experiment directive and experiment-run command; if said experiment-run command is proprietary as to method or intellectual property (IP) then adjust as to legal issues, said experiment being run so that a source of the experiment directive to run the experiment and a source of the experiment-run command are anonymous to each other, wherein price is passively determined, transaction is invisible to other participants, and the project can be executed by a sponsor acting as an agent or as a riskless principal.

In order to remain competitive, many research tool manufacturers seek to continuously improve overall equipment and research effectiveness. To facilitate these improvements, the invention provides implementing computer-based applications to employ such techniques as research-robot equipment monitoring, fault detection and classification, run-to-run control, predictive and preventative maintenance, collection and analysis of data from research equipment, equipment experimental result monitoring, in-line QA/QC monitoring, integrated data reduction/filtering, the reduction or elimination of uncontrolled experimental results, equipment matching, and other aspects of automated robot control.

A further embodiment provides for a storage service that includes one or more of the following steps and/or processes: a Web-based ordering page; the web-ordering page connected automatically to a secondary, automated service-order directive transmission; the order and purchase process connected to an optionally clinician-supervised step of automatically preserving and storing the stem cells; the order and purchase process connected to a step of delivering the storage vial (or ampule) to a secure storage location maintained by a 3rd-party provider (such as, for example, a safe-deposit storage box in a bank or other facility); the purchase process connected to a step of delivering to the purchaser a physical key to the storage facility and lock-box or a "delivery key code" that enables the purchaser at any chosen time to initiate physical delivery of the stored vial to the purchaser's possession.

A further preferred embodiment of the business method includes the steps of providing for a transmittal envelope that is especially suited and/or designed for a particular storage container and routing to a particular storage facility, whereby the transmittal envelopes bear sufficient identifying coding so that the envelopes can be automatically manipulated by robotic handling, processed, stored and later retrieved and reshipped based on the exterior coding.

A further embodiment provides for transmitting the container with storage directions and/or with usage directions. The storage directions and/or usage directions can be combined with other data incorporated into a data component that is affixed to or otherwise permanently integrated with the primary container, secondary container and/or special envelope or special mailing container.

A preferred embodiment of the business method provides additionally for offering and selling the service as a prepaid component of an obstetrical service.

A preferred embodiment of the invention provides for a stem-cell-storage, service-business system comprising: a database that stores information about a plurality of medical service professionals, hospitals, clinics or a combination thereof who deliver at least one of the services of delivering babies, attending births, taking samples of umbilical cord tissue or blood, storing umbilical cord tissue or blood, extracting cord blood stem cells, and storing cord blood stem cells; business system software; an application server that is connected to the database and accessible to customers via an Internet connection and that hosts the business system software; a communication means that communicates information about the professional, hospitals, clinics or a combination thereof to potential customers of the business system, communicates information about one or more customers' choosing of services of the professionals, hospitals, clinics or combination thereof to the business system, or both; an input means, whereby a customer inputs information to a relational database relative to the customer; and a planning means that plans stem-cell storage for a customer accessing the system, wherein said information in said database is stored in a form of a relational database, wherein a customer accessing the application server through an Internet connection causes the business system software to initiate the planning means based on input information from the customer, wherein the planning means connects or relates the customer's input information to information about the medical services and retrieves from the relational database information sufficient to complete and deliver a standard service order.

Another preferred embodiment provides a computer implemented system for selling stem cell storage services comprising: a database containing storage-method and medical-service-provider information wherein the storage-method and medical-service-provider information comprises service provider data and pre-storage processing and storage methods; an online purchasing interface where a customer or a reseller accesses the purchasing interface to acquire at least one storage service; a planning interface where a customer accesses a presentation of available options for medical services to acquire at least one storage-service product; a front office interface for providing purchase order information and marketing information and for receiving at least one order from at least one customer wherein the at least one order is related to at least one of the plurality of stem cell storage service products; and a processor for processing orders received from the front office interface; wherein the database, the purchasing interface, the planning interface, the front office interface, and the processor are interoperably connected.

BRIEF DESCRIPTION OF THE DRAWINGS

FIG. 21 illustrates aspects of a business method for automated research system services according to an embodiment of the invention, being a succession of web pages or web screens that can appear according to an embodiment as part of the providing of an offer to a potential customer and the recording of order information and completion of the ordering transaction.

DETAILED DESCRIPTION

Figure 1:
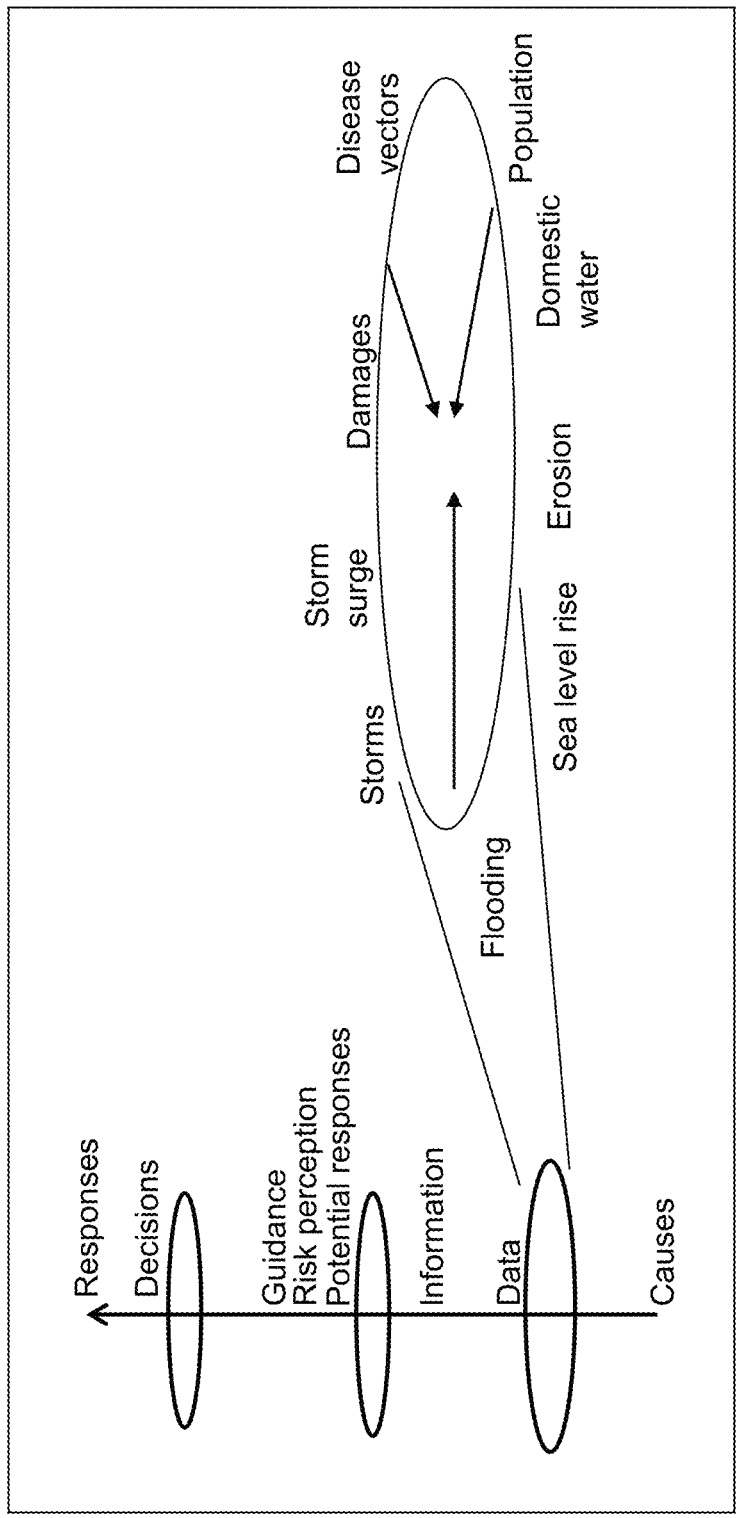
FIG. 1 illustrates dimensions of an integrated monitoring, modeling and management (IM3) methodology addressing global environmental change that can be automated according to an embodiment of the invention.

This specification explicitly references U.S. patent application Ser. No. 12/009,793, filed Jan. 22, 2008, having priority to U.S. Provisional Application No. 60/881,638, filed Jan. 22, 2007; U.S. patent application Ser. No. 12/290,731, filed Nov. 3, 2008, having priority to U.S. Provisional Application No. 60/985,160, filed Nov. 2, 2007; U.S. Divisional patent application Ser. No. 13/339,370, filed Dec. 28, 2011; and U.S. C-I-P patent application Ser. No. 13/351,210, filed Jan. 16, 2012, all of which foregoing referenced applications are inventions or co-inventions of this same inventor and/or are applications assigned to a common person or inventorship entity as this instant application, and all of which foregoing referenced patent applications are incorporated herein by reference in their entirety.

One embodiment of the invention provides a method for attaching a learning process to a linked object database (ODB), with artificial intelligence (AI) rules, constraint-based decision modeling, and simulation based on learning-revised instruction sets, model congruence testing, model conflict detection, and model variation, in order to configure optimized search for experiment objects (EOs) that can be executed with minimum supervision (e.g., automatically by robots) in order to create a desired experimental outcome.

The invention further provides for creating a bridge between current computing and biomedical research technologies and a new era of R&D optimization technologies based on the most advanced Internet and software technologies by connecting distributed libraries of EOs with distributed providers of robotic lab services and flexible data analysis engines (DAE) and systems modeling, such as, e.g., cellular systems biology research methods, that can be provided as contract research services to produce new knowledge.

The invention disclosed and claimed herein, in one aspect thereof, comprises a system that facilitates management of an automated research process. An Experimental Object (EO) research component in communication with one or more laboratory processes operates according to process conditions to output an experimental result, which EO research component at least one of monitors and controls the process using modularized code. A rules engine component in an Experimental Director (ExpDir) module processes one or more rules in association with the modularized code to control the laboratory process conditions in real time by balancing process efficiency criteria to arrive at an optimal result.

ARS and System Functions

The invention can include an automated research system (ARS) to establish a normal set of functional operations in a system under study (hereinafter the 'studied system', or SS. In general, then, an ARS will be used in specific domains of an SS. The invention can include a generalized ARS that can be directed toward many differing domains of SS, or it can include specialized ARSs that are tailored for a specific domain of a specific SS (such as human biology, SS-HB, or global environmental change, SS-GEC). In general, an ARS can be directed to solve the following problems:

A. Whole System Functions
Subsystems/module/object/component
B. Problems(s):
(1) To solve for causes of system dysfunction.
(2) To solve for solutions to correct system function
 (a) single-function solutions
 (b) multiple-function solutions Prior observations (data) may have established a normal set of functional operations (NSFO), which can be described in a manual of operations (such as, for example, in the case of human health, one or more manuals of medicine, the Merck Medical Manual, a standard medical dictionary, and/or one or more knowledge bases or knowledge assemblies that are products of companies such as Genstruct Inc. (Cambridge, Mass.), and/or other assemblages of biomedical knowledge).

The ARS of one embodiment of the invention can establish a manual of normal operation for an SS by multiple testing of numerous example systems, in each test monitoring or observing one or more functional observables (or parameters, or factors). The ARS of one embodiment of the invention can test dysfunctional systems or functions (or component subsystems of such systems) in order to solve for causes of system or subsystem dysfunction. Further, the ARS of additional embodiments of the invention can test dysfunctional systems (or component subsystems of such systems) in order to solve for functional solutions (which can include added or corrected components) in order to correct system (or subsystem) function.

One embodiment of the invention provides for a learning machine and method of use thereof for learning about any system of any domain, wherein the learning machine (LM) comprises a knowledge base (KB), Library of Possible Experiments (LOPE), etc., and wherein the method of use includes providing a user-specified goal (USG). The LM according to an embodiment of the invention includes at least a LOPE, at least two EOs, at least an experiment director (ExpDir) module and a data analysis engine (DAE).

Experiment Chamber

An ARS according to an embodiment of the invention can focus on instances, samples, parameters, factors or other measurable aspects or characteristics of a SS, where the SS is studied in an experiment chamber (EC, or ExpCh), which EC can be a laboratory, or a series of laboratories, or a combinations of chambers within one laboratory or distributed between multiple laboratories or locations. In the case of an environmental system, such as the global environment, the experiment can comprise a series of observations of aspects of the global environment itself, either from remotely sensed satellite perspectives, or from measurements taken within the system itself (such as, for example, air samples or water samples that are taken and measured in a laboratory, or in situ measurements in a body of water, or in the atmosphere, or in a biosphere or ecological location. Therefore, it is an aspect of the ARS to have at least one experimental chamber (EC) where observations are made at one or more time points and/or time intervals, with the understanding that the EC can be without walls. By way of example and without limitation, the EC can be a Petri dish, a volume of a fluid between two microscope slides, a cell, multiple cells within one or more wells of a microplate, a gene-expression chip, an organ, an organism, a bioreactor, a test tube, a population of organisms, a vat, an oven, a target, a crop field, a nuclear reactor, a particle-accelerator chamber, a planet, a reaction chamber, a virtual simulation environment, and/or any other volume, region, locale, substrate, environment or background within, upon, through, from and/or against which can be taken a measurement of a parameter, factor, function, behavior and/or aspect of a studied system (SS). This testing and/or observing in the EC can include spatial measurements in x, y and z and in time (t), including measurement and/or description of what, when, where, why and how a progression of observed events occurred. A group of people can comprise an EC, as can a town or a city, or a corporation, or a subs-population of consumers, or a defined market. As previously mentioned, the EC can be a combination of constituent ECs, such that, for example, an experiment could be conducted in an EC that could be established through and over a set of laboratories in multiple geographical locations.

Note that the experiment chamber can be a virtual environment that exists in a computing environment in one, two, three or many dimensions. For example, an experiment chamber could include the 2-dimensional and higher-dimensional test spaces used for studying cellular automata, such as described by Wolfram (2002, The New Science, Wolfram Press), which is herein incorporated by reference in its entirety).

To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

Definitions

As used in this application, the terms "component" and "system", when used in the context of an automated research system (ARS), which can be provided by embodiments of the invention, are intended to refer to a computer-related entity, either hardware, a combination of hardware and software, software, or software in execution. For example, a component can be, but is not limited to being, a process running on a processor, a processor, a software module, a software object (including an experiment object), an executable, a thread of execution, a software program, and/or a computer. By way of illustration, both an application running on a server and the server can be a component. An information management system (IMS) can be located on a server, or distributed across multiple servers. One or more components can reside within a process and/or thread of execution, and a component can be localized on one computer and/or distributed between two or more computers. Software program modules can include routines, programs, components, data structures, etc., that perform particular tasks or implement particular abstract data types. Computer system configurations can include personal computers, hand-held computing devices, microprocessor-based or programmable consumer electronics, and the like, each of which can be operatively coupled to one or more associated devices. An ARS module can include a 3-D, geodynamic, environmental modeling system.

It will be appreciated also that "system", when used in the context of a studied system (SS) that can be the object of research of embodiments of the invention, can be intended to refer to any system of any domain, including without limitation complex systems, energetic systems, dynamic systems, real-world systems, natural systems, environmental systems, climate systems, atmospheric systems, biospheric systems, oceanic systems, river systems, biogeochemical system, bioenergetic systems, biological systems, cellular systems, human and non-human systems, social systems, energy resource systems and global energy systems, inter alia.

A system can be a combination of multiple subsystems at varying levels of organization of varying spatial dimension and varying degrees of overlap (or non-overlap) between subsystems. Thus, in one embodiment, for example, a biological system can be a human organism comprised of subsystems such as skeleton and organs, wherein each of these subsystems are further comprised of cells of many different types.

A subsystem can be defined as a component, an object, and/or a module, wherein subsystem, object, module and component can be equivalent (for example, subsystem=module=object=component) and wherein any one of a subsystem, module, object and/or component can be formed, defined and/or constructed as a set of functions or as a set of one or more tangible objects inter-related by a set of functions. Thus, herein a subsystem can be purely a subset of systemic functions without tangible objects of it can be a subset of systemic functions in combination with a subset of tangible object components.

As used herein, the terms "infer" or "inference" refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources.

While certain ways of displaying information to users are shown and described with respect to certain figures, those skilled in the relevant art will recognize that various other alternatives can be employed. The terms "screen," "web page," and "page" are generally used interchangeably herein. The pages or screens are stored and/or transmitted as display descriptions, as graphical user interfaces, or by other methods of depicting information on a screen (whether personal computer, PDA, mobile telephone, or other suitable device, for example) where the layout and information or content to be displayed on the page is stored in memory, database, or another storage facility.

Acronyms and Abbreviations

ABRS—Automated biological research system
AIM3—Automated Integrated Monitoring, Modeling and Management
AIQME—Artificial Intelligence and Query Management Engine
AJAX—Asynchronous Javascript And XML
ARS—Automated Research System
BAC—biomodel assembly component
BIND—Biomolecular Interaction Network Database (http://bind.ca)
BIRN—Biomedical Informatics Research Network
CEO—chosen experiment object
CM—Congruence Module
CompRep—completion report
CORBA—Common Object Request Broker Architecture
CRO—contract research organization
DAE—Data Analysis Engine
DAML—DARPA Agent Markup Language
DB—database
DIP—Database of Interacting Proteins (http://dip.doe-nbi.ucla.edu)
DKB—Domain Knowledge Base
DOM—Document Object Model
DPI—data-processing instruction
EC—Experiment Chamber
ECC—Experiment Control Component
ED—Experiment Director (module)
EDM—Experiment Director Module
EDS—Experimental Design Sequencer
EM—Equipment Module
EO—Experiment Object
EO-Chosen—Experiment object chosen
ESS—Energetic System Simulator
ETF—Energy-Technology Feedback
Exp-CH—Experiment Chamber
Exp-CTRL—Experiment Controller
ExpDir—Experiment Director (module)
FTO—freedom-to-operate
GUI—graphical user interface
HPRD—Human Protein Reference DB (http://hprd.org)
HTP—High-Throughput
HUPO-PSI MI—Human Proteome Org., Prot. Stds Init., Molec. Interact.
IBIS—Integrated Bayesian Inference System
IG—Information Gap
IKF—information-knowledge feedback
IM3—Integrated Monitoring, Modeling and Management
IMS—information management system
INEM—information needed evaluation module
IntAct—IntAct Protein Interaction DB (Eur. Bioinf. Inst.)
IP—intellectual property
ISA—International Standards for Automation
ISD—Inter-Site Distance
KB—Knowledge Base
KBAM—Knowledge Base Assembly Module
KBAC—Knowledge Base Assembly Component
KB-MSM—Knowledge Base for Molecular Systems Model
KL—Knowledge Library
LAN—Local Area Network
LOPE—Library of Possible Experiments
LSID—Life Science Identifier
MAGE—MicroArray and Gene Expression
MIAME—Minimum Information About Micro-array Experiment
MIAPE—Minimum Information About Proteomics Experiment
MINT—Molecular INTeraction database (http://mint.bio.unirona2.it/nirt)
MIPS—Munich Info. Ctr Protein Sequences (http://mips.gsf.de)
MSMs—Molecular Systems Models
NED—Next Experiment Design
NSFO—normal set of functional operations
ODB—object database OIL—Ontology Interchange Language
OOP—object-oriented programming
OSITA—one skilled in the art
OTS—off-the-shelf
OWL—Web Ontology Language
PC—personal computer or parameters codes
PDO—processed data output
PHP—PHP: Hypertext Preprocessor
QA/QC—Quality Assurance/Quality Control
QM—Query Manager
QSAR—quantitative structure-activity relationship
RDBMS—Releational Database Management System
RDF—Resource Description Framework
REAC—Reverse Engineering Assembly Component
REAL—reverse-engineering algorithm linear
RE-MSM—Reverse Engineering-Molecular Systems Model
ROI—Return on Investment
SBML—Systems Biology Markup Language
SIS—Starting Instruction Set
SLAM—Sub-Linear Association Mining
SM—Systems Model
SOAP—Simple Object Access Protocol
SOMs—Self-Organizing Maps
SQL—Structured Query Language
SS—Studied System
SSC—Starting Set Controller
SS-GEC—Studied System-Global Environmental Change
SS-HB—Studied System-Human Biology
SSKM—Studied System Knowledge Model
SSL—Secure Sockets Layer
SSP—System Service Provider
SVG—Scalable Vector Graphics
SVM—Support Vector Machine
UI—user interface
UML—Uniform Modeling Language
UQI—User Query interface
USG—User-Specified Goal
USG—PC-user specified goal parameter codes
USP—United States Patent
VOI—value-of-information
VOIA—value-of-information analysis
WSDL—Web Services Description Language
XCEDE—XML-based Clinical Experiment Data Exchange schema
XML-extensible markup language The present invention is now further described with reference to the drawings, wherein like reference numerals are used to refer to like elements throughout.

Figure 2:
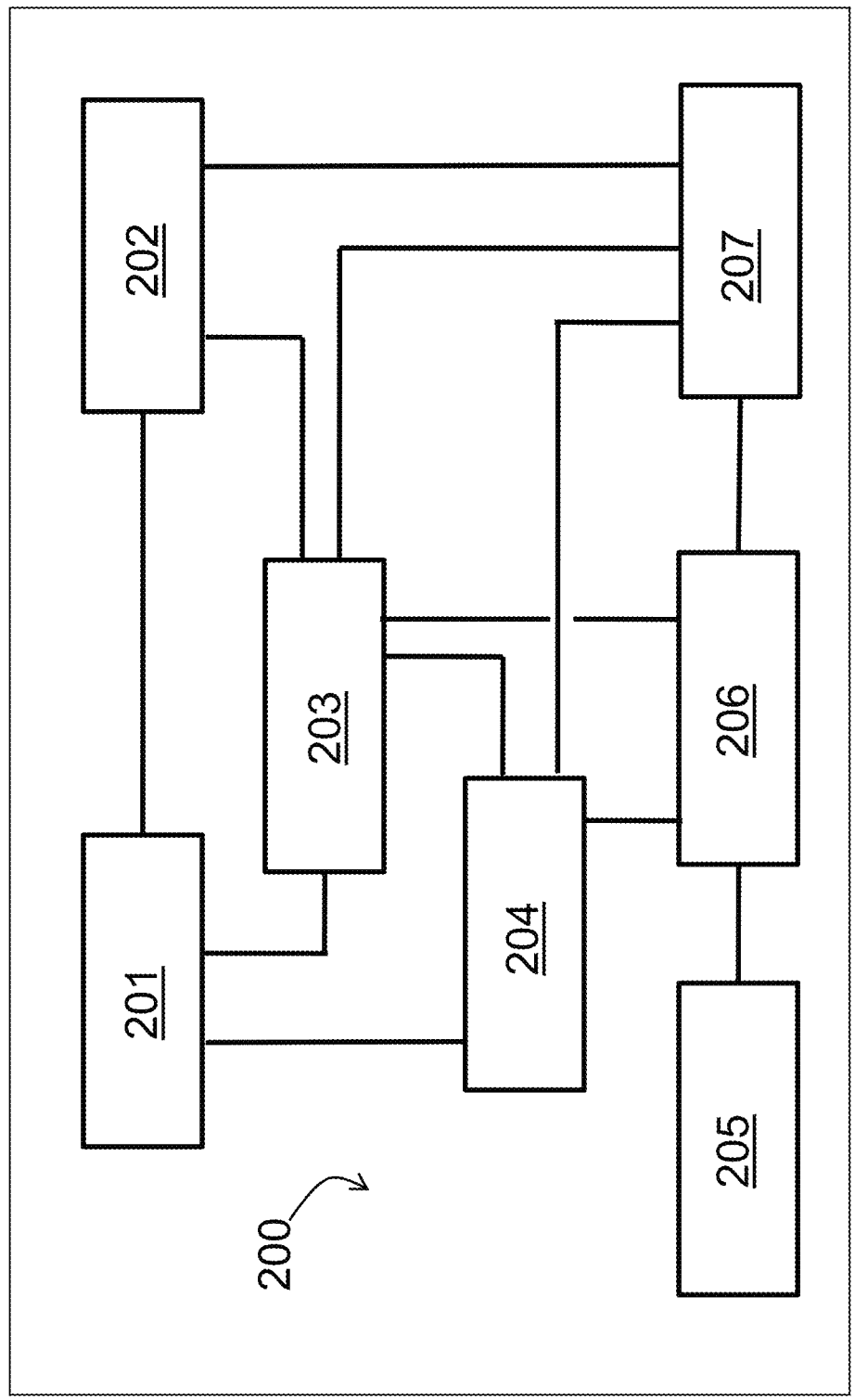
FIG. 2 illustrates an automated research system (ARS) according to an embodiment of the invention.

FIG. 2 illustrates a system 200 that employs a rules-based Experiment Director (ExpDir) engine 204 for automated research in a studied system (which can be a biomedical environment), in accordance with the subject invention. The system 200 can include an Experiment Object (EO) process (not shown) that is being conducted using process equipment 201 (such as high content screening platforms, incubators, aligners, and robot arms to move samples from one station to another, for example). In order to manage the EO process, the system 200 further includes a research Experiment Controller component (here this component is part of the ExpDir module) that interfaces to the process and equipment 201 for monitor and control thereof. The Experiment Director research component 204 includes a process control component that includes software and/or hardware for controlling the automated lab equipment 201 that runs the EO experiment process. For example, one module of the process control component 204 can be a particular model of a hardware device (e.g., rackmount or standalone) that includes processing capability, memory, firmware, and interface hardware/software that facilitates interfacing to the equipment 201 for control thereof. It will be appreciated that the research control component 204 and process control component (not shown) can be distributed in different locations.

The research component 204 can also includes a data acquisition component that can include sensors and hardware/software suitable for instrumenting the process and equipment 201 to take measurements of research subjects, samples or the like before, during, and after performing the EO process. The research component 204 can also include a standards-based code component (e.g., S88) that allows for development and implementation of modularized code for management of the process and associated equipment 201, the process control component, and data acquisition component.

The process control component and data acquisition component both interface to the process and equipment 201 across a communications network, which can be any conventional wired and/or wireless network, including the Internet. It is to be appreciated by one skilled in the art that the network can also be a combination of networks such that communications between the process, equipment 201, process control component and data acquisition component can be via a high speed local bus suitably dedicated for data acquisition and control environments when required, whereas the remaining part of the network is an wired/wireless Ethernet network, the Internet, or the like.

Still referring to FIG. 2, the system 200 can also include a rules engine that processes rules in support of controlling and/or making measurements associated with the EO process and/or research lab equipment 201. The rules are processed in accordance with the standards-based code of the code component. The rules engine and code component can communicate across the network, and with the other entities including, but not limited to the process control component, data acquisition component, process, and process equipment 201. The system 200 according to an embodiment can also include a user interface 205 and Query Manager 206 and database server 203. The server 203 can contain a knowledge-base relevant to the research. A data analysis engine 202 can take results from laboratory equipment 201. A knowledge-base assembly module (KBAM) 207 can here include a Modeling submodule, a Congruence testing submodule and a Simulation module. The KBAM 207 can interface with the Query Manager 206 and with the ExpDir 204 when evaluating continuation of the experimental process into another experimental round.

It is to be appreciated that by way of example, and not by limitation, these are only a few of the entities that can be employed in the system 200. For example, there can be a multiplicity of processes and associated equipment, control, and data acquisition components in the system 200 each or a combination of which are controlled or control related processes. Moreover, the system 200 can be accessed remotely via the Internet or a LAN (Local Area Network), WAN (Wireless Area Network) or the like, by employing secured login procedures to authorized users. Such login can provide read-only access, or even provide full access such that any of the system entities can be manipulated before, during, and/or after performing the process.

Virtual Automated Laboratory

Automated Lab locations can be distributed in different geographic locations and connected by the Internet or other computer network, e.g., located in different "rooms", where each "room" could be a different company connected through a network, or where each "room" could be an actual laboratory room in a different company connected through the Internet.

An information management system (IMS) can be located on a server, or distributed across multiple servers, where each server with IMS components has multiple functionality, including multi-media file services and processing, flash memory storage, hard disk digital memory storage, operating software, software to manage robotics, software to manage network connectivity with other similar servers, software to manage interactions with the system rule engine (or rule engines) and/or the system query engine (or query engines), and, inter alia, software to manage interaction with an RDMS and data mining engine (or module). These servers can be small and portable, being built on technology similar to that manufactured by Omnilala, Inc.; (Newton, Mass.), such as devices employing the VIA Mini-ITX motherboard (computer system circuit board having multiple standard hardware connectivities and onboard processing power). As well, these servers can access multiple system databases, with system ontologies and XML parsers. The system software can include artificial intelligence modules, including inference engines (which can incorporate rules engines that are based on Bayesian probability methods).

Aspects of laboratory automation (including robotics) managed by the automated research system according to an embodiment can include, without limitation:

Liquid Handling
Automated Assay
Microfluidic Workstations
Microplate Detectors
Detectors
Bar Code Readers
Incubators
Storage
Consumables management devices
Robotic Management devices
Robotic Transport devices
Laboratory Automation Workstations
ADME-Tox Workstation
Assay Workstations
Chemistry management devices Example 1

Figure 3:
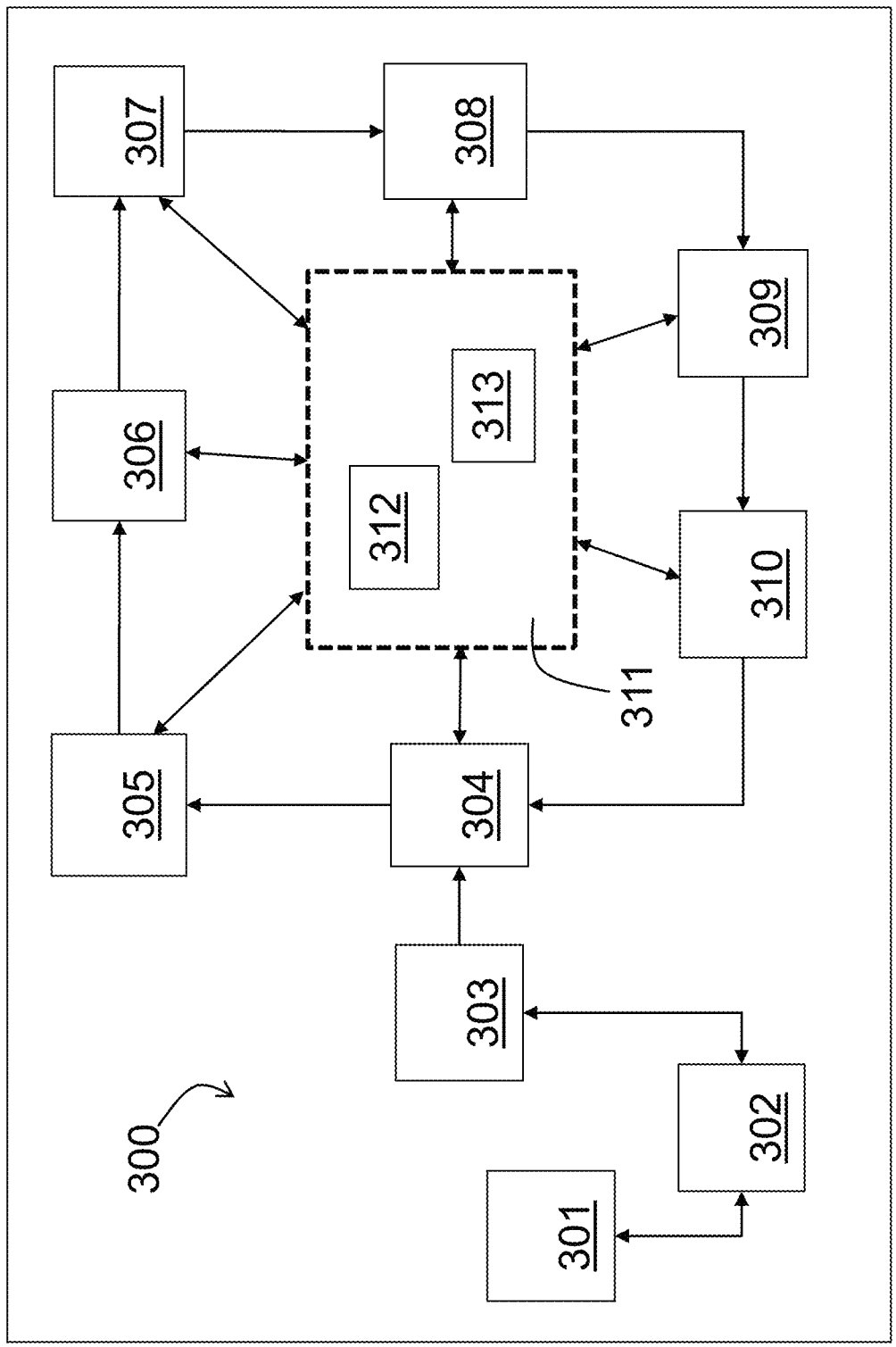
FIG. 3 illustrates an automated research system (ARS) according to an embodiment of the invention.

Referring to FIG. 3, after selection of an EO and execution by the ExpDir module a Knowledge Library (KL) element (which can be an element of a knowledge base (KB)) and starting instruction set (SIS), which can have elements of a User Specified Goal (USG) starting instruction, are used by a Starting Set Controller (SSC) and Experimental Design Sequencer (EDS) to initiate a first Experiment Sequence (#1). Results of the first Experiment #1, after (i) passing into and through the data selection/filtering and data analysis modules of a Data Analysis Engine (DAE), and (ii) passing through the Biomodel Assembly and Simulation steps, are (iii) used together with the KL in the Congruence Module where (iv) an information gap is derived and passed to an Automated Experimental Designer Module (EDM) (that can be the Experiment Chooser module with a random creative design component and/or a decision rule design component (e.g., which builds a new EO from closely associated techniques of previous unsuccessful EOs, based on expected outcomes of many sub-EO technique steps)), in order to (v) produce a design for an automated Experiment #2, where said design is passed to the ExpDir/EDS to initiate Experiment #2 in the automated laboratory. Then, the results of Experiment #1 and Experiment #2 are processed through Data Analysis steps (i.e., the combined results of all experiments from the current and previous cycles) are combined in the Biomodel Assembly steps, new Simulations are run, from which simulation results and the KL are drawn together in the Congruence Module where an information gap is derived and passed as the inputs again to the EDM, which EDM produces a design for automated Experiment #3, and so forth through as many cycles as are needed to meet the goal functions of the Starting Instruction Set. This system is graphically depicted in FIG. 3 wherein a robot-driven laboratory 305 has computer and software control components, including OTS Robot-Driver Components and OTS Experiment-Control Components;

a data processing and filtering module 306 (such as, for example, HTP image analysis and data selection), is comprised of a module wrapper that controls, directs and operates multiple OTS software components;

a Data Analysis Engine (DAE) module 307 is comprised of a module wrapper that in turn controls, directs and operates OTS software components selected from the set of GLP, Spotfire, SAS, Mathworks, and other comparable data-analysis applications, and which operations include hierarchical clustering, association mining, pathway analysis, etc;

a Modeling Module 308 can be or can include a bio-model assembly component (BAC) that can create from prior outputs of the DAE 307 plus the KL or KB a set of nested, hierarchical, node-arc (or object-interaction) causal network models (such as, for example, molecular system models (MSMs) and/or dynamic systems models (such as, for example, dynamic molecular models), which models allow dynamic simulation operations to be applied, wherein said causal modeling module (or BAC) includes a Reverse Engineering Assembly Component (REAC) or module that operates on the outputs of the DAE 307 to form a reverse-engineered molecular systems model (RE-MSM), and where said BAC additionally includes a Knowledge Base (or KL) Assembly Component (KBAC) that operates on inputs from a prior KB to form a knowledge-base molecular systems model (KB-MSM), and where the BAC further can include a Congruence Testing module (or component) that interacts iteratively with both the REAC and KBAC to derive a closest-fit resultant MSM by iteratively comparing the first-generation RE-MSM and KB-MSM for differences in structure (topology, objects, relationships and dynamics), and then adjusting and constraining a second-generation RE-MSM and KB-MSM by using high-probability information (above some uncertainty threshold) from each first generation KB-MSM and RE-MSM, respectively, to constrain the creation of the 2nd-generation RE-MSM and KB-MSM, respectively;

an n-dimensional Energetic (or Dynamic) Systems Simulator (ESS) 309, is capable of instancing systems simulators for any system (such as, for example, for virtual, biological, social or energetic systems) and at multiple levels of biological organization (including a dynamic Biomolecular System Simulator), and can "run" the resultant systems model (SM) (such as, for example, an MSM) passed from step and component 308, where the model "runs" or iterations (a) test the capability of the MSM to predict current experimental results that were not used to build the SM (or MSM), (b) predict signaling cascades and events that may manifest in significant perturbations of certain system objects (such as biological objects) in the SM (or MSM) (such as, e.g., biomarkers), (c) test effects of manipulations of the SM (or MSM) to simulate a system dysfunctional state (such as a disease state in a bio-system), (d) test effects of corrective interventions applied to the SM (or MSM) in dysfunctional (diseased) or healthy mode to predict impacts and results of such interventions, and (e) test the robustness of the resultant SM (or MSM) by variation of parameters and/or Monte Carlo approaches to yield stability, robustness and/or fitness metrics as functions of uncertainties in the SM (or MSM) (e.g., such as by analyzing topology, structure, objects, and/or relationships);

an ExpDir Module 310 (which can include an Experiment-Design Module) can create, access or derive a set of potential experiments constrained by information derived from the USG (or SIS), the KB (or KL), and previous SM (or MSM) analyses, whereby EOs from the LOPE (which can be Template Experiments) are modified by random or guided permutation to create a Potential Experiment Set, and where each Potential Experiment is virtually explored in an experiment-simulation step to produce Simulated Results for each of the Potential Experiment Sets, whereby new information to be probably learned about certain variable objects and interactions can be categorized and distinguished from controlled objects and interactions, and where a value-of-information analysis (VOIA) operation (which analysis establishes value in relation to (i) reducing uncertainty about certain objects and interactions in the MSM from ExpDir 310, (ii) increasing the robustness of MSM simulation results and predictions, and (iii) generating additional, well-defined, testable hypotheses) is applied to those categorized and distinguished objects and interactions, whereby a next experimental sequence can be chosen based on a function that maximizes the expected VOI from the anticipated experiment; whereupon the ExpDir (or EDM) outputs a next EO (or Next Experimental Design (NED)), which is passed to the ExpDir controller (or EDS) 304; a Starting Instruction Set Controller Module 304 can be coupled with an ExpDir 310 (which can have an Experimental Design Sequencer element). For the first experiment of a series of iterative, learning cycles, the ED 310 establishes a first Experiment Object (EO) from the SISC Module 304 (via a USG and the Query Manager module reaching an EO from a LOPE source). For successive experiments in the iterative, learning process, the EDS uses the NED passed from ExpDir 310 as the experiment design to be next sequenced to the Experiment-Control Components in step and laboratory 305;

an Artificial Intelligence and Query Management Engine (AIQME) 303 contains a set of rules, constraints, supervision modules, result-goals, optimization procedures, and fault/error handling supervision components.

a Visualization Engine 301 can be wholly or in part OTS components, (such as OmniViz, etc.); a Graphical User Interface 302 allows interaction with many of the other components, particularly the AIQME 303, laboratory 305, object database 312, systems simulator 309 and ExpDir module 310 [as needed for human learning and monitoring of system operation, and for supervised learning cycles; and a database function 311 contains an Object Database (ODB) 312, such as Oracle®, MS-Access® or another OTS application has program connectivity to all other modules and components, acquiring and storing system information, and holds the Knowledge Base Library (KB/KL), as well as providing storage for the Biomolecular Models and other data and program objects, and contains an Algorithm Library and Subcomponent (subroutine/object-class) Library 313, which is embedded within and/or directly coupled to the ODB 312 and has program connectivity to all other modules and components. The algorithm and subcomponent library 313, may be stored as program objects within the ODB 312.

As shown by the connecting arrows in FIG. 3, the database component 311 is connected (can exchange information with) the SIS Controller 304, laboratory 305, data processing and filtering module 306, DAE 307, MM 308, ESS 309, and ExpDir 310. Visualization Engine 310 and Graphical User Interface 302 can exchange information. Graphical User Interface 302 and AIQME 303 can exchange information. Information can pass from AIQME 303 to SIS Controller 304, from SIS Controller 304 to laboratory 305, from laboratory 305 to data processing and filtering module 306, from data processing and filtering module 306 to DAE 307, from DAE 307 to MM 308, from MM 308 to ESS 309, from ESS 309 to ExpDir 310, and from ExpDir 310 to SIS Controller 304.

Figure 4A:
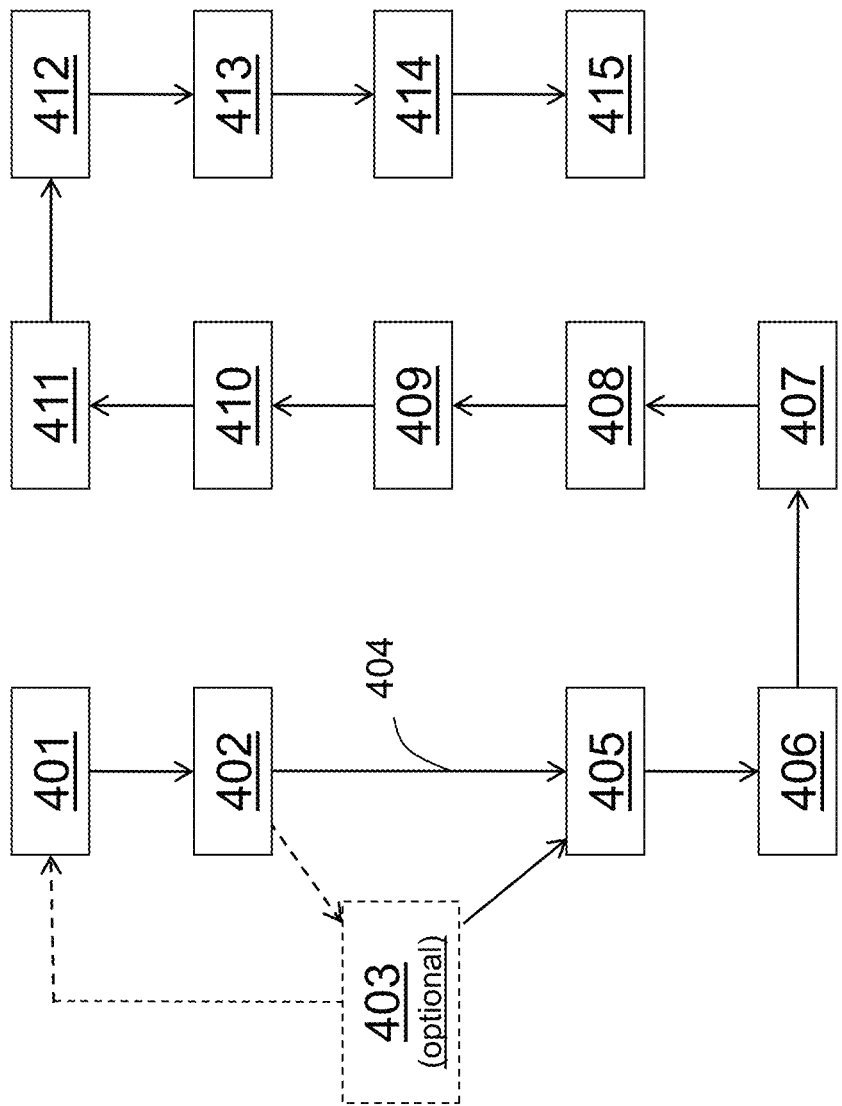
FIGS. 4A and 4B illustrate aspects of an automated research method according to an embodiment of the invention.

FIG. 4A illustrates a method according to at least one embodiment according to the Invention, wherein at step 401 a user chooses a top-level domain from the User Query Interface (UQI) and Goal Library (GL) and develops a user-specified goal (USG), which goal can include, for example, such tasks as 'characterize normal'; 'detect/characterize abnormal'; 'test/find corrective (or adaptive/protective)'; 'optimize corrective (or adaptive/protective)'. At step 402 the user chooses USG parameter codes (USG-PCs) in interaction with the Query Manager (QM) for input to the Experiment Director (ED). At step 403, which is optional, the ARS optionally tests the list of user-specified parameters for completeness against a completeness rule and index associated with the Query Manager (QM), Experiment Director (ED) and the LOPE. If the list is incomplete, the program passes control back to the UQI, prompting the user to correct the goal specification. If step 403 is completed or optionally bypassed, then at step 404 the ARS passes the user specified goal (USG) to an Experiment Director Module (ED). At step 405 the ED accesses the LOPE to extract a subset of EOs that correspond to the USG-PCs and the EOs can contain, without limitation, data related to standard descriptors, ontologies (such as ontologies developed by the Interoperable Informatics Infrastructure Consortium (I3C)), input/output, parameters, cost, time and interoperability certification. At step 406 the Experiment Chooser Module begins processing the USG-PCs and the subset of EOs in order to select a chosen EO (EO-chosen). At step 407 the Exp Chooser module accesses, or runs, the Experiment Usage Engine (EUE) as part of the selection evaluation, where the EUE can use parameters to search the LOPE and can evaluate a subset of the LOPE based on VOI and other selection criteria (from the parameters and/or built into each EO), and with step 408 including the EUE accessing usage data stored in the EOs, and processing this EO usage data together with the USG-PCs, following decision-rule sequences in a Decision Module (Rule Engine) component of the Experiment Chooser Module.

Still referring to FIG. 4A, the ARS chooses an EO at step 409 and at step 410 the ED module passes the choice and the EO data to the Experiment Controller (Exp-CTRL). At step 411, the Exp-CTRL module accesses data about available Experiment Chamber (Exp-CH) resources that can be in-house and/or available through a distributed network, including at step 412 using LOPE protocols and/or protocols within the EO to instruct initiation of the EO-Chosen at some Exp-CH, such as, for example, at a laboratory of a Contract Research Organization (CRO) under an automation contract to the ARS. At step 413 the Exp-CTRL module controls progress of the EO-chosen. It will be understood that step 413, differing embodiments of the invention, can include control of an experiment that is completely automated through a robotic laboratory, or partially automated through a laboratory with combined work of human scientists and robotic research platforms, or control of an experiment that is carried out by one or more human technicians who are following the directives of the EO-chosen experiment specification. In a most preferred embodiment step 413 is fully automated through a fully automated robotic laboratory with access to the complete range of experimental materials and/or material libraries and robotic experimental equipment needed to execute the EO-Chosen. Step 413 includes numerous sub-steps that are detailed within the EO-Chosen software object, including, without limitation, experiment scheduling, experiment sharing, charging, accounting, sequencing, collecting data and storing data to an EO-Chosen.DATA.OUT file.

At step 414 the Experiment Controller passes at least one EO-Chosen.DATA.OUT file to the Data Analysis Engine (DAE). At step 415, the DAE processes the data according to instructions, rules and/or parameter codes (including the USG-PCs) passed from the QM, and/or passed from the EO-Chosen's data-processing-instruction (DPI) data, and/or passed from the Ex-CH in a DPI field of the DATA.OUT transmission, and/or additional data-processing-instructions and/or data-processing-rules held by the DAE's own DPI libraries.

Figure 4B:
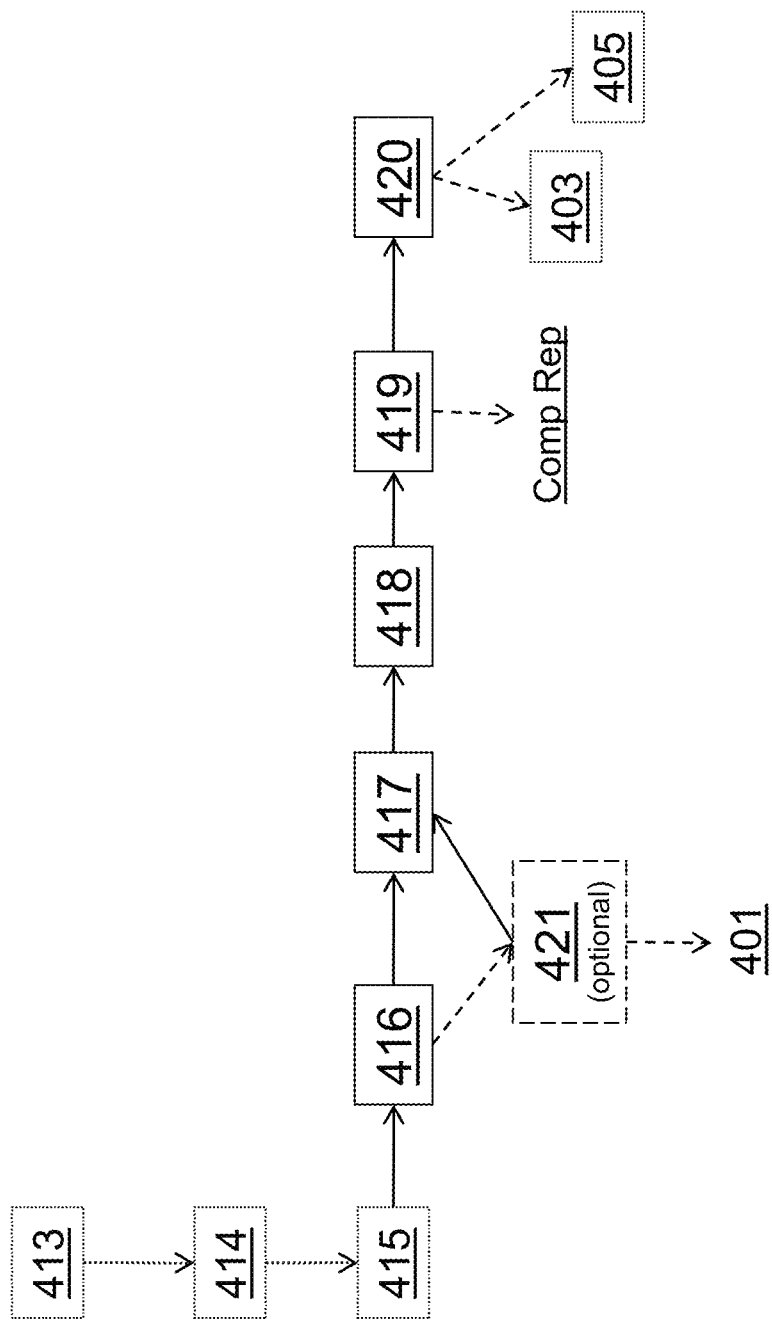
Figure 5B:
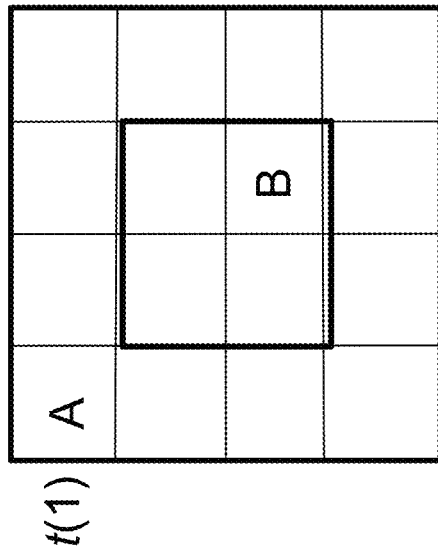
FIGS. 5A-5D illustrate Type-1 experiment outcomes according to the invention.
Figure 5D:
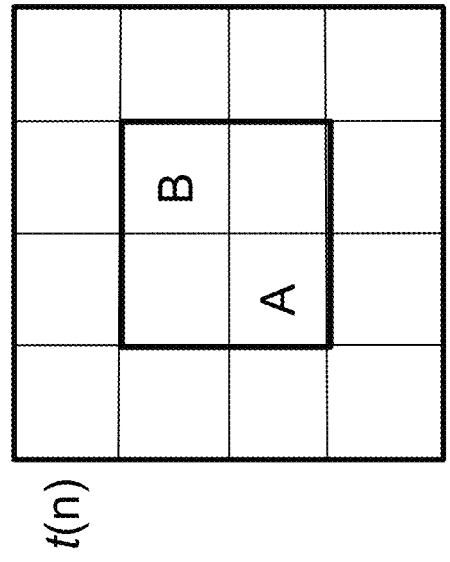
Figure 5A:
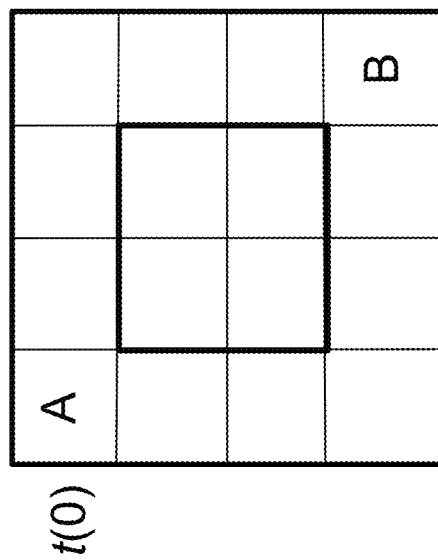
Figure 5C:
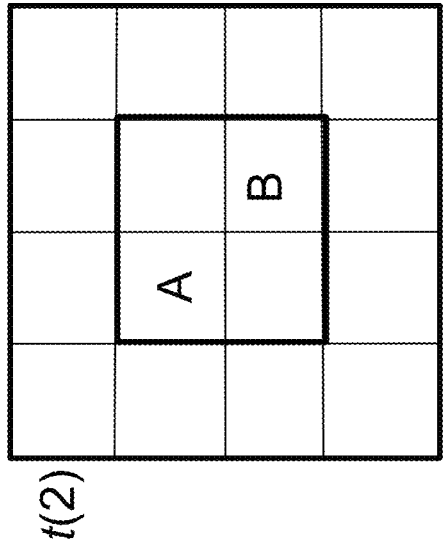
Figure 6A:
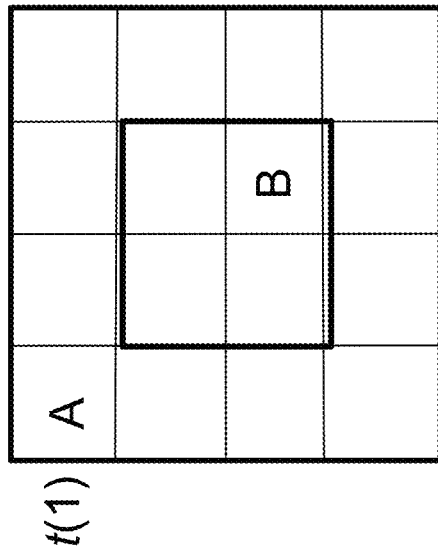
FIGS. 6A-6D illustrate additional Type-1 experiment outcomes according to the invention.
Figure 6B:
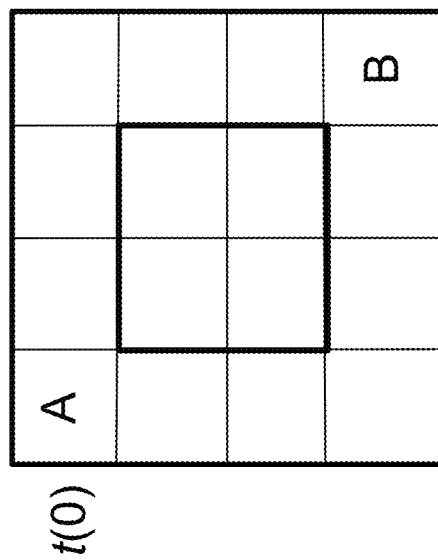
Figure 6C:
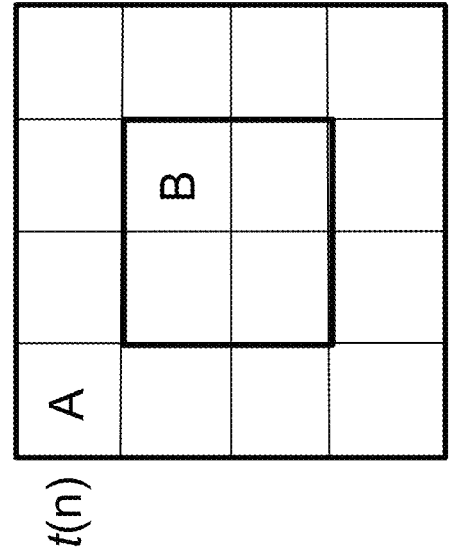
Figure 6D:
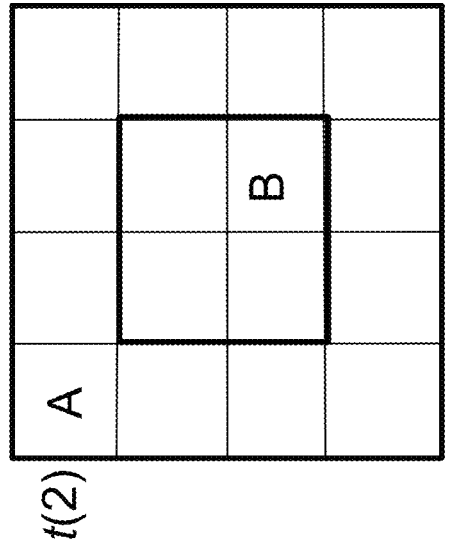
Figure 7B:
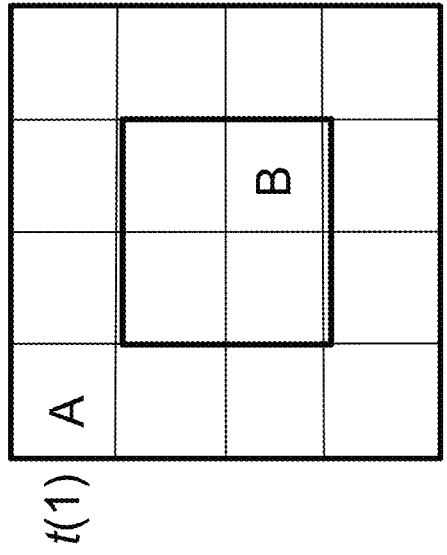
FIGS. 7A-7D illustrate further Type-1 experiment outcomes according to the invention.
Figure 7D:
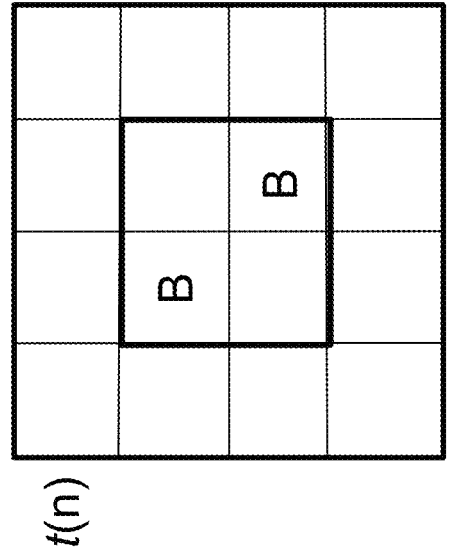
Figure 7A:
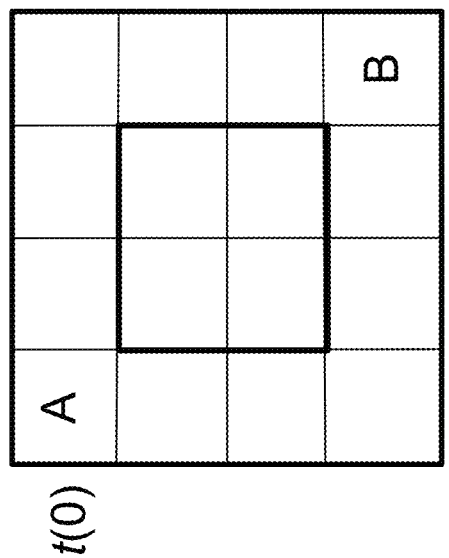
Figure 7C:
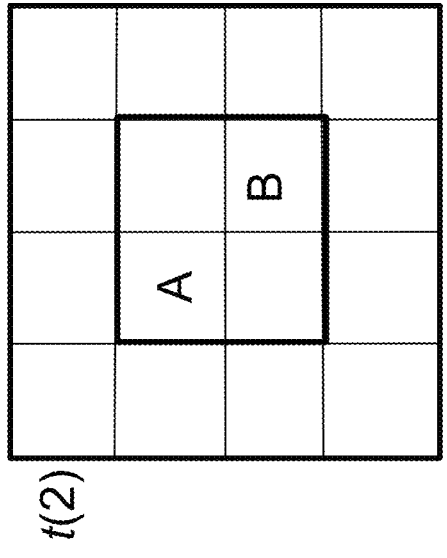

Referring now to FIG. 4B, at step 416, which continues from the progression of steps 413, 414 and 415 described above, the DAE can include substeps of characterizing the studied system using system reverse-engineering analysis steps that find and/or generate behavior rules and define normal relations of parameters based on prior knowledge and the new information in the DAT.OUT file. The USG and QM can include directives that optimize the translation of test results through the data-processing step to provide processed data output (PDO) suitable as input for the Congruence Module (CM). The LOPE (including its EOs) can specific inputs and provide directives for the DAE, including specifying parameters (or variables) that will be processed in a data mining step. Each EO in the LOPE has DAE interoperability parameters. These can be part of any number of standard experiment data processing interoperability parameters, such as are provided by those skilled in the relevant art, for example the MIAME, MAGE, BIRN methods and others, (see above). Similarly, the USG interface and/or the Query Manager can specify inputs and provide directives for the DAE, including specifying parameters (or variables) that will be processed in a data mining step. An optional step 421 can operate to evaluate the data sufficiency for the intended data mining operation within the DAE, where failure at this step can lead to returning program control to the User Interface to adjust the setting of the goal and associated target parameters.

The substeps within the DAE step 416 can include data filtering, data normalization, statistical analyses, hierarchical clustering, principal component analysis, regression analysis, correlation analysis, support vector machines, neural network analysis and any number of a range of data processing techniques called for by the Exp-Chosen object, the Exp-Chamber, the USG, the QM, the Congruence Model, or the DAE itself. Substeps of the DAE step 416 can include fault-tolerant error-checking routines with corrective restart and secondary analysis pathways in the event that a data-processing error is detected. Substeps of the DAE step 416 can include numerous stages of checking for data completeness and data sufficiency in the DATA.OUT file passed from the Ex-Chamber. The DAE substep for reverse-engineering can be sequenced subsequent to various data mining steps or in interactive association with data-mining algorithms.

At step 417, Processed Data Output (PDO), which can include results of the reverse-engineering update of a system causal network, is passed to the Congruence Module (CM). In step 418 the Congruence Module completes updating of the prior knowledge model for the appropriate SS domain (some of which updating may have already occurred in a reverse-engineering DAE step) and in step 419 the CM compares the prior knowledge bases with the updated knowledge base for the current iteration of the ARS. The updating of the knowledge base (or knowledge model, or knowledge assembly) can include accessing additional libraries of information and/or data from distributed data sources that lie outside the ARS that can be related to new information provided through steps 414 and 416, inter alia. As depicted in FIG. 4B, step 419 can include an iterative process of mapping, overlay, testing, matching, solving and otherwise learning with regard to the congruence of new information relative to the prior knowledge model. Here, a number of techniques that are known to those skilled in the art can be applied.

At step 419, the Congruence Module is continuously evaluating the improvement in overall logical strength of the evolving knowledge model, based on metrics that are part of the CM testing library and/or other metrics that can be supplied by the USG and QM, as well as metrics that can be derived from distributed library source. For instance, "richness" and "concordance" are metrics that are used by the library resource of Genstruct Inc. (Cambridge, Mass.), whereas other measures of robustness can be created based on increase in VOI of the knowledge base for answering simulated hypotheses or closing the information gap (IG) with the goals of the USG. An information gap can be measured during the step 419, where certain target information at some degree of certainty is set as one of the goals in the USG. These goals can include reducing uncertainty in a parameter, or detecting a previously unknown relationship association between at least two parameters, or determining a normal range of related parameter behavior through one or more time steps, or measuring any output of one parameter based on changing of certain inputs and/or experimental conditions or procedures. The Congruence Module step 419 can be goal-directed to reduce one or more specified information gaps (IGs).

When at step 419, or upon completion of certain substeps for testing reduction of IGs, the ARS determines that an IG has been reduced beyond a required specification in the USG, then the program produces a completion report (CompRep) that describes the experiment conducted, the DAE steps achieved, the results of the Congruence Module testing, the closure of the IG and any other reporting data called for by the USG, and delivers the CompRep to the user and the program terminates.

If at step 419, the Congruence Module procedures and testing fail to close the IG as specified by the USG and the QM, then the Congruence Module, at step 420, passes an IG report to the Experiment Director, which updates the USG-PC list, updates the ARS loop stage and updates the data for any relevant parameters in the Experiment Chooser Rule Library and/or the Experiment Usage Engine. At this point the ARS begins another cycle of operation corresponding to step 403 and 405 (see FIG. 4A description).

The Congruence Module results can include multiple target unknowns generated by the DAE and additional learning steps of the congruence testing and update of the knowledge base. These multiple new statements of unknown relationship relevant to the closure of an originally specified USG can spawn new sub-goals and USG-PCs, which can be instanced in multiple, parallel processes through subsequent loops of the ARS.

It should be noted that the original USG can be parsed by the Experiment Director into any number of multiple experimental pathways, such that a single user query could spawn dozens or hundreds of experiments at the direction of the Experiment Director, with scheduling and direction toward available resources being constrained by USG-PCs related to time, cost, safety, resources, etc., and with the partitioning of tasks being managed by a Multiple Experiment Manager, Scheduler and Sequencer Module that operates to optimize the rate of increase in useful experimental information within the set constraints.

The ARS of an embodiment of the invention can iteratively study numerous examples of normal and abnormal systems or system behaviors and/or subsystems or subsystem behaviors to build a library of normal function (or behavior, or operations) and/or a library of dysfunctional (abnormal) functions (or behavior, or operations).

User Interface Goal Library

The ARS according to at least one embodiment of the invention can include the capability to address many different system types, where the type or category of studied system (SS) can be selected by the user via the User Interface (UI) that provides the user access to a library of possible studied systems and possible research goals for each of these possible studied systems. For example, without limitation, the Goal Library (GL) could contain the following list of systems for possible study by the ARS:

Studied System Type 1 (SS-1): Virtual System; 2-dimensional grid
    (including, for example an SS subtype of 4×4 grid with 16 locational squares, two components: {A,B})
    Type 1 research goals:
    (a) Test/observe to characterize normal
    (b) Test/observe to detect abnormal (can be same set of experiments as (a), or close)
    (c) test changes to system to correct behavior
    (d) Optimize corrective strategy Studied System Type 2 (SS-2): Environmental System
    (including, for example, the Global Climate System);
    Type 2 research goals:
    (a) Observe to characterize normal
    (b) Detect abnormal
    (c) Test changes to correct system behavior
    (d) Test adaptive strategies
    (e) Optimize corrective and/or adaptive strategies Studied System Type 3 (SS-3): Computer Program/Hardware System
    Type 3 research goals:
    (a) Test to characterize behavior
    (b) Detect bugs
    (c) Test changes to correct bugs
    (d) Optimize Studied System Type 4 (SS-4): Electrical System
    Type 4 research goals:
    (a) Characterize normal
    (b) Detect/characterize abnormal
    (c) Test corrective designs
    (d) Optimize among corrective designs Studied System Type 5 (SS-5): Information System Studied System Type 6 (SS-6): Social Organization or Group:
    (The research goal and EOs in the LOPE for this domain of studied systems (SS) can include an EO that uses an artificial intelligence module in the EO that puts information onto the World Wide Web (such as, for example, through blogs) and measures responses (such as, for example, by page views, view duration, entered responses, inter alia), with the EOs in this SS domain further including instructions for the DAE to data mine and analyze the resulting data to observe, filter, categorize and/or sort instances and parameter responses per each instance and/or to further establish and describe normal and abnormal responses within the studied system to this experiment. These experiments can produce results useful to studies of political constituency attitudes or behavior, consumer product marketing attitudes or behavior, or media marketing effectiveness)

Studied System Type 7 (SS-7): Industrial Sub-sector

Studied System Type 8 (SS-8): Living Organism
    Type 8 research goals:
    (a) Characterize normal function
    (b) Detect/characterize abnormal function
    (c) Test/find corrective strategies
    (d) Optimize among corrective strategies Parameter Codes The series of parameters (codes) that can be used to specify an experiment within the Library of Possible Experiments (LOPE) can include parameters (P-#) for such things as experimental stage (1) (for example, P1:1 can refer to the very first round of learning by the ARS in response to a USG, with no prior knowledge in the knowledge base, only specification of the SS domain; whereas P1:47 might refer to an ARS operation whose stage is currently in loop 47 of an experimental iteration on the path of a particular USG. Similarly, other parameter codes can be utilized, such as, without limitation:

P2—Safety
    P3—resolution
    P4—Subsystem type
    P5—Subsystem scope
    P6—Scope
    P7—Cost/Budget
    P7—Time/Deadline
    P8—Robustness Required
    P9—Regulatory
    P10—Intellectual Property The method and system of at least one preferred embodiment of the invention can be better understood and illustrated by simple examples, following below. It will be understood, however, that the scope of the automated research system provided by the invention reaches to include much more complicated systems and examples of automated research that those skilled in the art can implement by extrapolating from the description and examples of the invention provided herein.

Example 2. Simple 2-D Matrix System

[System SS-1, containing component A and component B]. Take a simple system of at least two interacting subsystems A and B.

Referring to FIG. 5A-5D, corresponding to an experiment measured at three time steps and at an end point, respectively, for a simple system of two components, A and B, an observation of system function may show that the two components migrate into the inner box and remaining within that region in a balanced, ongoing association (which, for example, in the case of a biological cellular system, could correspond to two biological molecular constituents migrating into and remaining within the nucleus of the cell). Repeated observation of system behavior through multiple time points, from initial conditions to an end point, could establish that this migration and continued association within a bounded sub-region of the system is a rule of normal system function for this studied system, SS-AB. A statistical distribution of positions at each time point, t(o)-t(n), may be found to follow a normal Gaussian distribution of configurations for each time point, such that a "normal" behavior of the system over all the time points could be considered a progression through any of a normal set of positions for any time point. Each time point could have a normal distribution of potential configurations, with some configurations more probable than others, with the probable normal behavior defined by marking some degree of deviation (e.g., some degree of sigma) from a center of the normal distribution. Conversely, an abnormal behavior of the system could be observed in an experimental run, with "abnormal" defined as a behavior that at one or more time points displays a configuration that is not within a specified deviation from the center of the normal population of configurations for that time point. For example, for a simple system, SS-AB, having a normal rule of reaching an endpoint with component 'A' and 'B' in balanced association within a sub-region (as shown in FIG. 5A-5D), an experiment could detect a behavior such as shown in FIG. 6A-6D or a behavior such as shown in FIG. 7A-7D. In the experiment having results shown in FIG. 6A-6D, for example, component 'A' never enters the sub-region. In FIG. 7A-7D, both components enter the central sub-region, but component 'B' doubles while component A disappears.

Experiment Director

An ARS according to a preferred embodiment of the invention can have an Experiment Director module (ED), which can interface with and interact with a Library of Possible Experiments (LOPE), wherein the LOPE can be a part of the ARS. For instance, returning to the very simple studied system SS-AB described in FIGS. 5A-5D, a LOPE can include the following three experiments, inter alia:

SS-AB-Exp.#1: Initiate A+B system with A(x,y) and B(x,y) at t(0) specified as A(1,1) and B(4,4). Complete measurements at t(1), t(2) and t(3). Observe positions and record to SS-AB-E1.data.out. FIGS. 5A-5D can be seen to be the observed data that could be the result of one run of this experiment, whereas FIGS. 6A-6D and FIGS. 7A-7D would be additional data for additional runs of this experiment.

SS-AB-Exp.#2: Build the system as in Exp #1, but create a series of Monte Carlo instantiations with twenty random starting positions of A(x,y) and B(x,y). Complete four time steps for each of the twenty runs. Observe each time step and record to SS-AB-E2.data.out.

SS-AB-Exp.#3: Create random experimental start, constrained to 100 instances (runs) and ten time steps per run. Observe each time step and record data to SS-AB-E3.data.out.

A Value of Information (VOI) index can be created for each of the possible experiments in the LOPE, where the values can be compared as a relative percentage (most valuable is 100%), for example:

| Experiment   | VOI |
|--------------|-----|
| SS-AB-Exp.#1 | 5%  |
| SS-AB-Exp.#2 | 40% |
| SS-AB-Exp.#3 | 60% |

An Experiment in the Library of Possible Experiments can be generally termed an Experiment Object (EO). An Experiment Object can be described as a software object and/or as an information object within the ARS generally. The EO can be a technique described in text and/or graphic form, or a series of techniques, methods, operational steps and/or other manipulations that can be understood to comprise an experiment, or that can be characterized as measuring, detecting, studying, observing, perturbing or otherwise sensing state or change in one or more parameters, factors or variables in a studied system. The EO can exist as a software object and/or as a menu in an encyclopedia of experimental techniques.

In one embodiment of the invention the ARS can include a LOPE that contains at least two EOs as software objects, wherein the EOs include information about the conduct of the experiment, the required inputs, the likely data outputs, "private" object data required for successful direction of the experiment procedures when run out through the Exp. Director (such as, for example, when the ED directs a virtual experiment and/or directs a series of robotic experiments), "public" data that can be shared with other components of the system at any time, and other information concerning the experiment, such as the VOI index information (calculated and/or based on prior experimental usage), cost information, location information, intellectual property ownership aspects of the experimental methods or materials used in the experiment, intellectual property claims in the experimental results, experiment sequencing information, information on safety and safety procedures, information on regulatory and compliance requirements and procedural documentation steps, time requirements, allowed experiment variations, preferred SS domains for experiment application, experiment input requirements, experiment prohibitions, uncertainty information as to process and outcome and any other information that can be used to evaluate the suitability of the experiment for progressing toward the user-specified goal.

Thus, in the foregoing example of an ARS according to the invention for studying a simple SS-AB, the LOPE can contain SS-AB-EXP #1-3, and these can be stored as software objects, wherein the software objects can be accessed by the ED to direct any one of the experiments and where each of the EOs contains self-referential descriptive data, such as, for example, VOI data, that can be used to choose which experiment to apply at a given time to make progress toward the user-specified goal (USG). In the above example, for instance, Exp #3, having a higher VOL owing to the greater amount of data that the experiment would acquire, could be evaluated by an Experiment Chooser module as a more preferential experiment to run to gain information.

In one embodiment of the invention, the invention provides for an ARS in which success metrics and/or value of information gained from the results of an experiment that has previously been run by the same ARS (or by a $3^{rd}$ party or $3^{rd}$ party's research system) is summarized at least as to category and success and or VOI scores, with a step included to update the EO in the LOPE using this summary information, with the updated VOI information being aggregated into the VOI metric held by the EO in its self-referential data store.

Experiment Usage Engine (EUE)

In addition, an Experiment Usage Engine (EUE) can be included in the ARS according to at least one embodiment of the invention, wherein the EUE is a software module that interfaces with the Experiment Chooser and the LOPE and can include a set of conditional rules and/or rule evaluation steps that create a ranking of preferential application of one or more experiments to an Information Gap (IG) challenge (or information need, according to the USG). As described above, various rules of application for any experiment can be included as part of the EO itself, specified by the creator of the experimental technique, method or menu, or by the provider of the experimental service (such as, for example, a providing laboratory object) and/or the experiment usage rules can be assembled as an evaluation set within the EUE. An example of an EUE evaluation set can be as follows, in the context of the simple SS-AB research domain:

| Experiment | Usage Rules |
| --- | --- |
| SS-AB-Exp.#1 | If no prior information, then use Exp#1<br>If budget <100, then use Exp#1<br>If research loop iteration >100, then do not use Exp#1<br>If robustness requirement >50, then do not use Exp#1 |
| SS-AB-Exp.#2 | If budget <300 and >100 units, and if robustness required >50 then use Exp#2 |
| SS-AB-Exp.#3 | If budget >300 units, and if robustness required >85 then use Exp#3 |

Investigating Biological Network Dynamics and Automated Experimental Loops: Applying RDF/OWL Embodiments of the invention further provide technology for meeting the challenge in biomedical research to evaluate results of gene expression experiments in the context of prior knowledge. One approach is to (a) analyze gene expression data to a first step of a reduced set of seemingly important genes that exhibit correlated behavior, (b) reverse-engineer from these data a probable network or set of networks without regard to prior knowledge, and then (c) attempt to make sense of the experimental result against a backdrop of pathways maps derived from curation and analysis of the biomedical literature.

Another approach is to utilize the reduced set of correlated genes from the gene expression data as a query to a knowledge base that is formed from the literature utilizing a myriad of bioinformatics tools, extracting a network or set of networks from the knowledge base formed in response to the query set. The first approach above offers the advantage, if done well and based on sufficient experimental design, to shed light on unknown unknowns, but suffers from the weakness of high uncertainty owing to uncontrolled variables. The second approach above is less likely to correct prior ignorance and error, but is more likely to generate a molecular network that sits robustly on an assembly of many prior lab experiments.

A preferred embodiment of the invention provides for combining these two above approaches, leveraging their strengths and minimizing their weaknesses. In addition, the invention provides for automating the generation of hypotheses and the design of iterative gene expression experiments that can benefit the pace of discovery.

Forward simulation is used in both the above approaches as part of deriving best fits between early guesses at a network and a conclusion about which derived network deserves to be considered more probable. Simulation of discrete logical cascading steps without concern for time sequence can provide some information about causation sufficient to generate hypotheses, but may provide little information about mechanism details. Modeling continuous signal changes in expression levels, with explicit treatment of time dynamics, can have a chance of allowing distinction between specific mechanistic pathways, including nonlinear responses and feedbacks.

To utilize RDF/OWL features in the effort to merge the above approaches to discover biological function the invention addresses a number of technical problems, including:

1. Time: The invention provides for creating standard approaches for modeling dynamics and time-based functions and coping with curated pathways (and/or causal networks) that have little or no dynamic information;

2. Spatial context: An embodiment provides for modeling spatial and system context, in the sense that there are numerous levels of self-organization requiring nested dynamic modeling in the forward simulation of molecular assemblages, cells, tissues, and metabolic systems, among others;

3. Fluid interactions: Given that mammalian biology proceeds to a large extent as a function of aqueous chemistry, an embodiment of the invention provides for modeling concentration, diffusion, pH, redox potential, ionic dissociation, and bulk transport in the modeling module;

4. Energetics: Energy parameters (as well as material balances) can provide important parameters for constraining a dynamic simulation model, including temperature, Gibbs free energy, enthalpy, entropy and other thermodynamics variables as well as energy represented in electrical potential and phosphate exchanges. Embodiments provide for developing ontologies for one or more of these thermodynamic functions and interrelationships;

5. Topology and Congruence testing: An embodiment provides for comparing causal networks topologically as an important method for rapidly bringing experiment-derived networks and literature-derived pathways into focus, highlighting match-ups and inconsistencies and determining information gaps that must be filled to meet a user-specified research goal. The invention provides useful standards for carrying topological descriptors forward with reporting of pathway relationships; and 6. Scenarios and Experimental Templates: An embodiment of the invention provides for an intelligent system that can propose an experimental design based on a generated hypothesis, a library of possible experimental approaches and/or scenarios must be available, with a logical structure that has sufficient flexibility for working between genes, proteins and metabolites, yet enough exact specificity to direct a robotic process.

Specific features can be included in the invention that take advantage of the Internet standard (Semantic Web) methods called RDF/OWIJLSID. Other features can be integrated with SBML, UML and other dynamic modeling standards known to programmers having ordinary skill in the art.

Example 3. Toxicity

Embodiments of the invention can provide a method to gain insight about molecular network interactions and metabolic response patterns associated with a toxic dose of Compound X to a biological sample. Data mining (such as with the SLAM algorithm in the GeneLinker Platinum™ software, Improved Outcome Software Inc., Kingston, Ontario, Canada) can be used to detect biomarkers and reverse engineering methodologies (such as the Integrated Bayesian inference System (IBIS) and reverse-engineering algorithm-linear (REAL) methods developed by Biosystemix, Kingston, Ontario) are used to gain insight into biological network interactions. The method then provides for:
1. Building further insight on potential toxicity by uncovering hidden relationships in "pan-omic" data sets and unique responses that correlate with treatment;
2. Identifying biomarkers of key outcomes from treatment of Compound X; and
3. Inferring the gene regulatory network imputed in and allowing prediction about dose-response outcomes of the particular compound.

These steps can be accomplished by utilizing databases of curated biomedical literature, such as those compiled by GeneGo, Inc. (St. Joseph, Mich.), Ingenuity, Inc. (Redwood City, Calif.) and/or Genstruct, Inc. (Cambridge, Mass.), inter alia, including data sets comprising:
Rat RNA samples
Response to Compound X:
  i. 1 drug treatments—high dose (toxic)
  ii. 1 drug treatments—low dose (non-toxic)
  iii. 1 vehicle treatment
3-4 post treatment time points
5-10 replicates per treatment group
8,000 gene Affy rat array (U34A); 75% known and 25% ESTs
Proteomics on Serum (2D Gel and SELDI)
Metabolomic data on urine (spectral)
Pathology and histopathology scoring (0-3)

The analysis method can then comprise the further steps of classification and identification of biomarkers, such as, for example, the following steps and substeps:
1. Identify sets of genes, proteins and metabolomic variables that accurately and robustly classify specific compound response, phases of the response, and outcomes in terms of histological and pathological data:
   a. Solve classification problems to assure comprehensive coverage of predictive genes, proteins and metabolomic variables.
   b. Consider associations between genes, proteins and metabolomic variables and outcomes within the same measurement time point, and across time points, to capture potential inductive effects.
   c. Identify distinct gene and protein expression and metabolomic variable profiles (markers) for adverse effects and for efficacy.
   d. Investigate associations between compound response, phases of response, and phenotypic outcomes.
   e. Statistically validate the classification results.
2. Integrate biomarker genes and/or proteins identified in current experimental results using nonlinear and combinatorial methods with biomarkers, such as, for example, those known or found earlier by GeneGo Inc. or Genstruct Inc. (or other knowledge assembly analysts, or known in the KBs or in the medical research literature).

The analysis method can then comprise the additional steps of reverse engineering and mapping causal network Interactions. In order to determine regulatory relationships that control key biomarkers, as identified in Stage 1(A), above, the method according to an embodiment of the invention can include the steps of:
1. Applying linear and nonlinear gene network reverse engineering methods to identify key influence genes, proteins and metabolomic variables; and
2. Reverse engineering a sufficient number of connections to allow reasonably robust simulations to probe hypotheses on therapeutic intervention effects.

Wherein, the output from the above steps in a preferred embodiment can include:
1. A listed subset of biologically relevant genes, proteins and metabolomic variables based on uncovering hidden relationships and unique and/or differential responses; and/or
2. Network and pathway interactions that regulate those genes, proteins and metabolomic variables with key influence on biological response.

Example 4. Knowledge-Base Assembly Function in Biomedical Research

Referring to FIG. 8A-8E, in an automated research system according to an embodiment of the invention, a knowledge base assembly function can include a combination of functions and interactive steps between a data-driven, reverse engineering module 800, a $3^{rd}$-party, literature-based, pathway assembly module 801, a congruence module 803 and a simulation module 802.

Figure 8A:
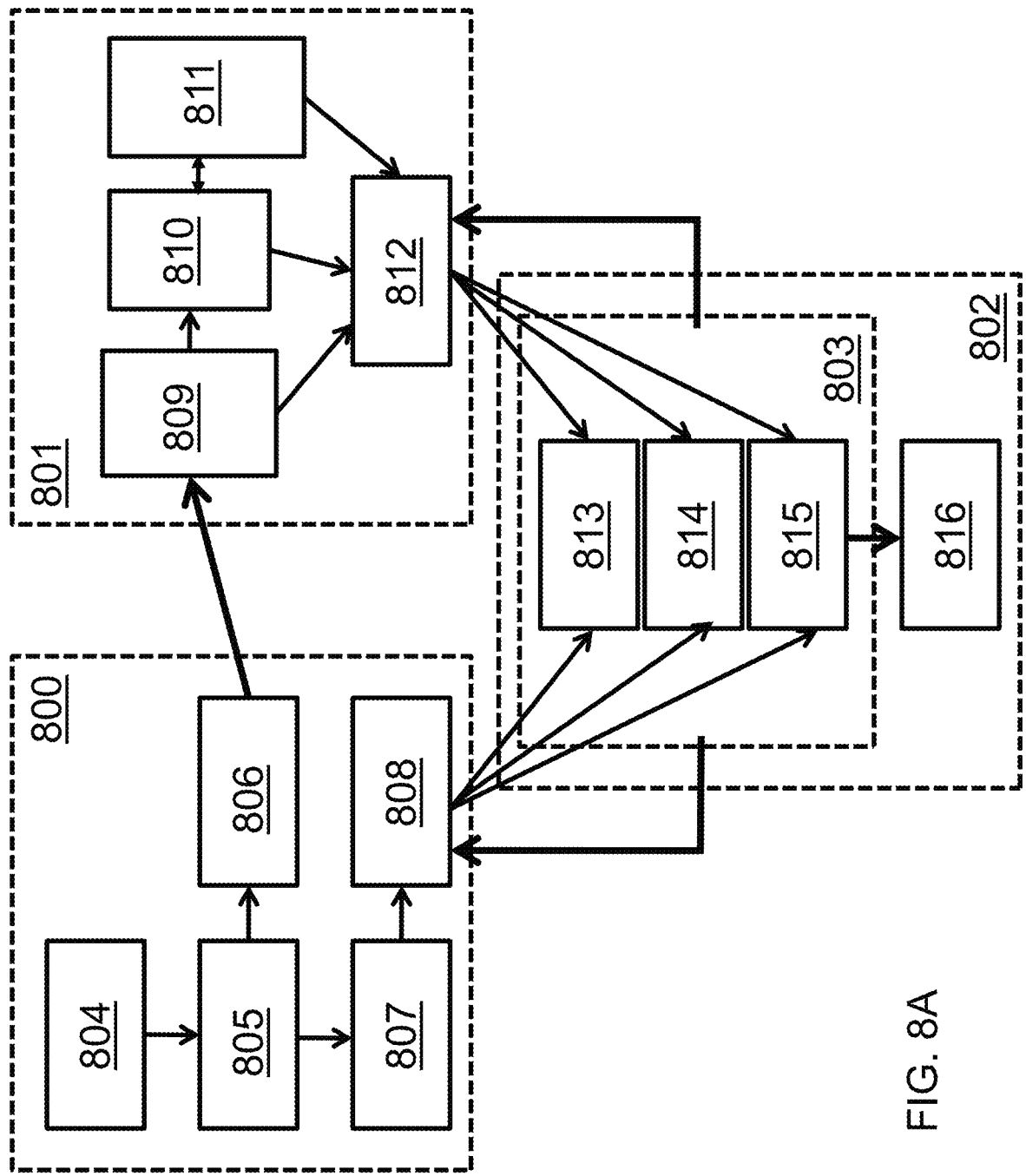
FIGS. 8A-8E illustrate additional details of knowledge-base-assembly functions in an automated research system according to an embodiment of the invention.

As seen in FIG. 8A, the reverse-engineering module function 800 applied to time series measurements of system variables includes completing statistical analysis steps 804 and then completing association-mining steps 805, to produce predictor-set output 806 for use in causal network analysis. Continuing from the association mining into further network reverse engineering analysis 807 can produce a reverse-engineered pathway network (REPN) model 808 that is based solely on probable causality based on associations between a set of variables, i.e, independent of prior knowledge from a knowledge base. A pathway assembly function 801 can proceed from a domain knowledge base developed from 3'-party literature sources, such as biomedical research publications representing millions of prior experiments conducted over many decades. The assembly of causal network within the knowledge base can include a text-mining step 809, development of one or more ontologies in step 810 and pathway mapping steps 811 which steps can combine to form a pathway database and network (PD&N) map 812 based on the prior knowledge in the knowledge base.

In the congruence module 803 a series of comparisons between the pathway database and network map 812 and the reverse-engineered pathway network model 808 can be conducted to determine whether or not the reverse-engineering of the experimental result reproduces the prior knowledge of the network, or whether there is a gap. The comparison can also reveal whether or not the experiment produced new information the fills in an unknown area of the prior network map. An in silico simulation step 816 can be conducted in conjunction with the converging of the pathway database and network (PD&N) map 812 and reverse-engineered pathway network (REPN) model 808 to detect improvements in how well the system is understood, on the assumption that improvements in understanding the system will lead to simulations that more closely approximate the outcomes of actual experiments. In FIG. 8A, a first comparison step at 813 can be tested for congruency between the PD&N map 812 and REPN model 808, where increase in congruency corresponds to increasing the matching overlap of the two pathway networks. Learning from a simulation step and degree of mismatch seen in congruence-test 813 between the PD&N map 812 and REPN model 808 can cause an updating from the Congruence Module 803 to both the knowledge base network map 812 and to the reverse-engineered network model 808. Following these updates, a second congruence test 814 is conducted, again exploring the converging of the PD&N map 812 and REPN model 808, with again the converged pathway model being tested in a simulation 816. As seen in FIG. 8E the simulation 816 can include dynamics and flux analysis 847, exploration of robustness and noise sensitivity 848, in silico knockout and constitutive overexpression testing (in gene expression networks) 849, and/or combinatorial perturbation analysis 850. Further updates can occur and further iterations of fitting reverse-engineered model to the knowledge-base map can be conducted 815.

Figure 8B:
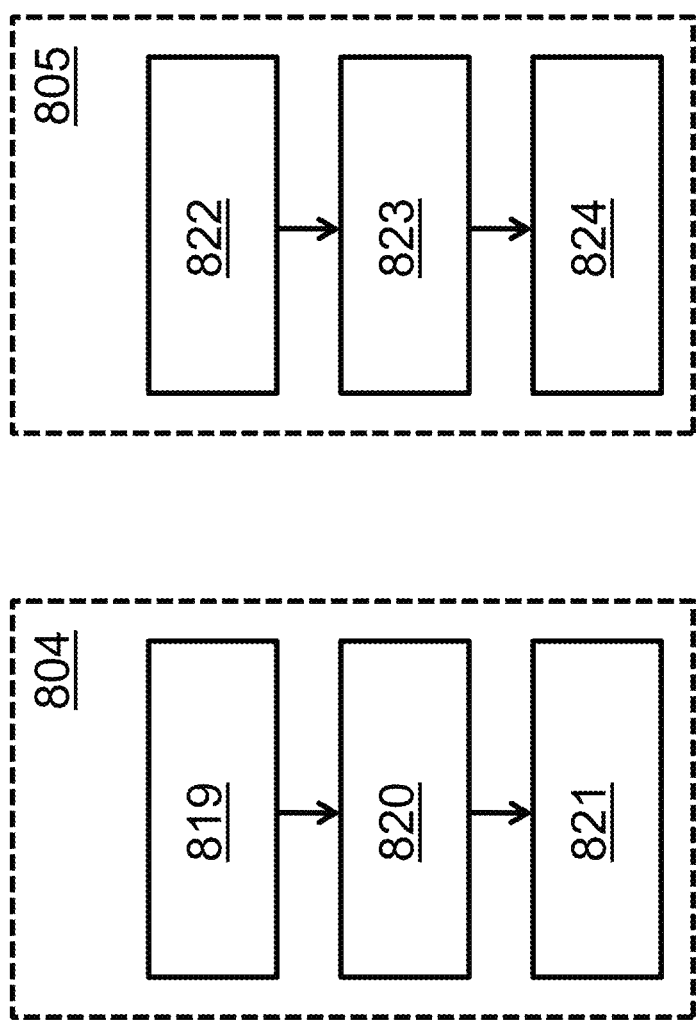

FIG. 8B illustrates that statistical analyses 804 can comprise examining replicates 819, selecting gene and protein sets 829 and statistical filtering 821, and that the association mining function can include applying sub-linear association mining (SLAM) 822 to select highly informative patterns (association sets), applying Bayesian inference 823 to select outcome predictive genes and markers, and assembling outcome-predictor sets of variables 824.

Figure 8C:
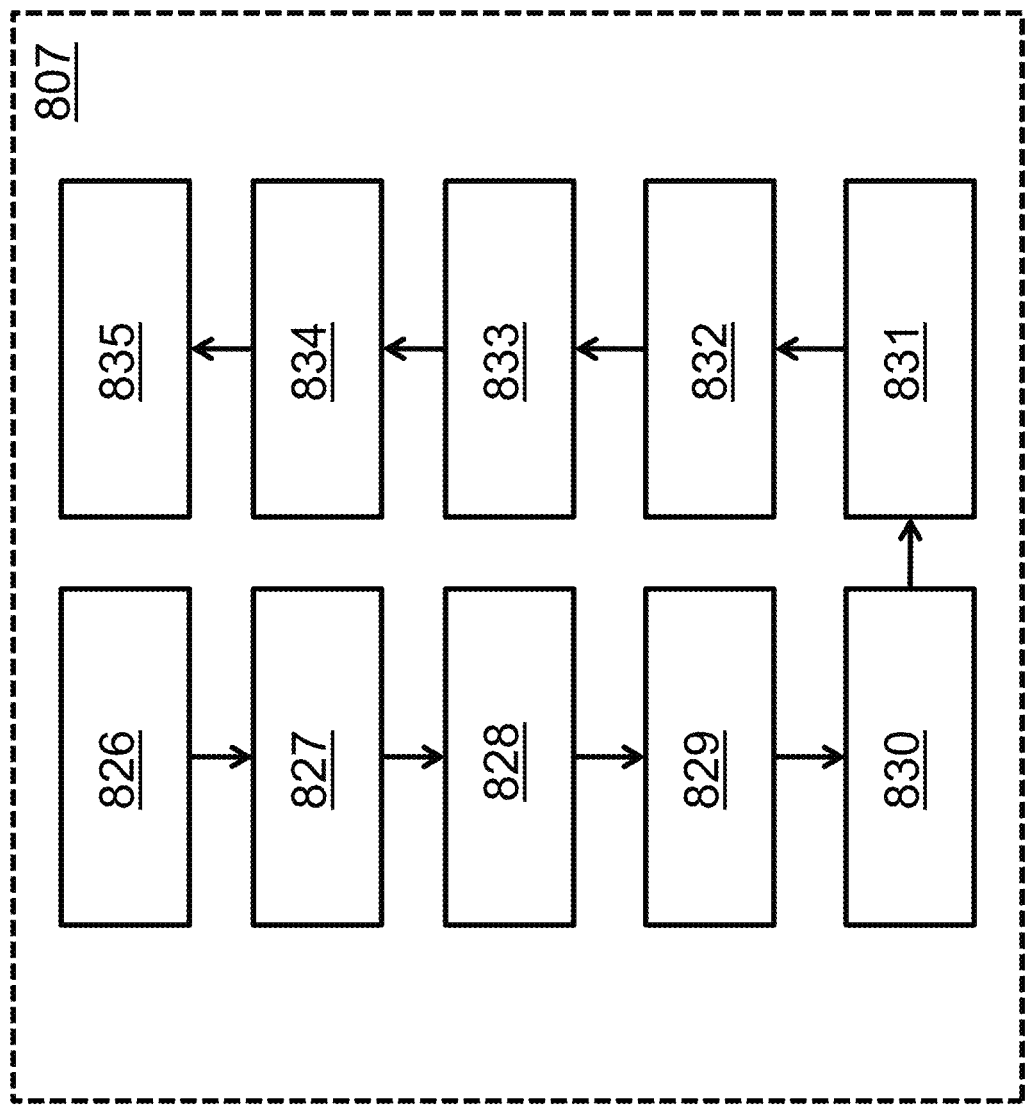

FIG. 8C illustrates that network reverse engineering functions 807 can include steps of initial exploration with a reverse-engineering linear algorithm (REAL™, as described by Biosystemix Ltd., Kingston, Ontario) 826, identifying novel pathway candidates 827, graphing and reviewing the imputed control/causal structure 828, constructing a network graph 829, graphing major regulatory nodes 830, estimating functional inferences of pathways 831, exploring dynamic pathway/network control through flux analysis 832, highlighting specific gene or protein contributions per experiment dose treatment 833, analyzing for non-linear dynamic networks 834 and applying further Bayesian approaches 835 to merge the previous analyses and estimations in a pathway network model.

Figure 8D:
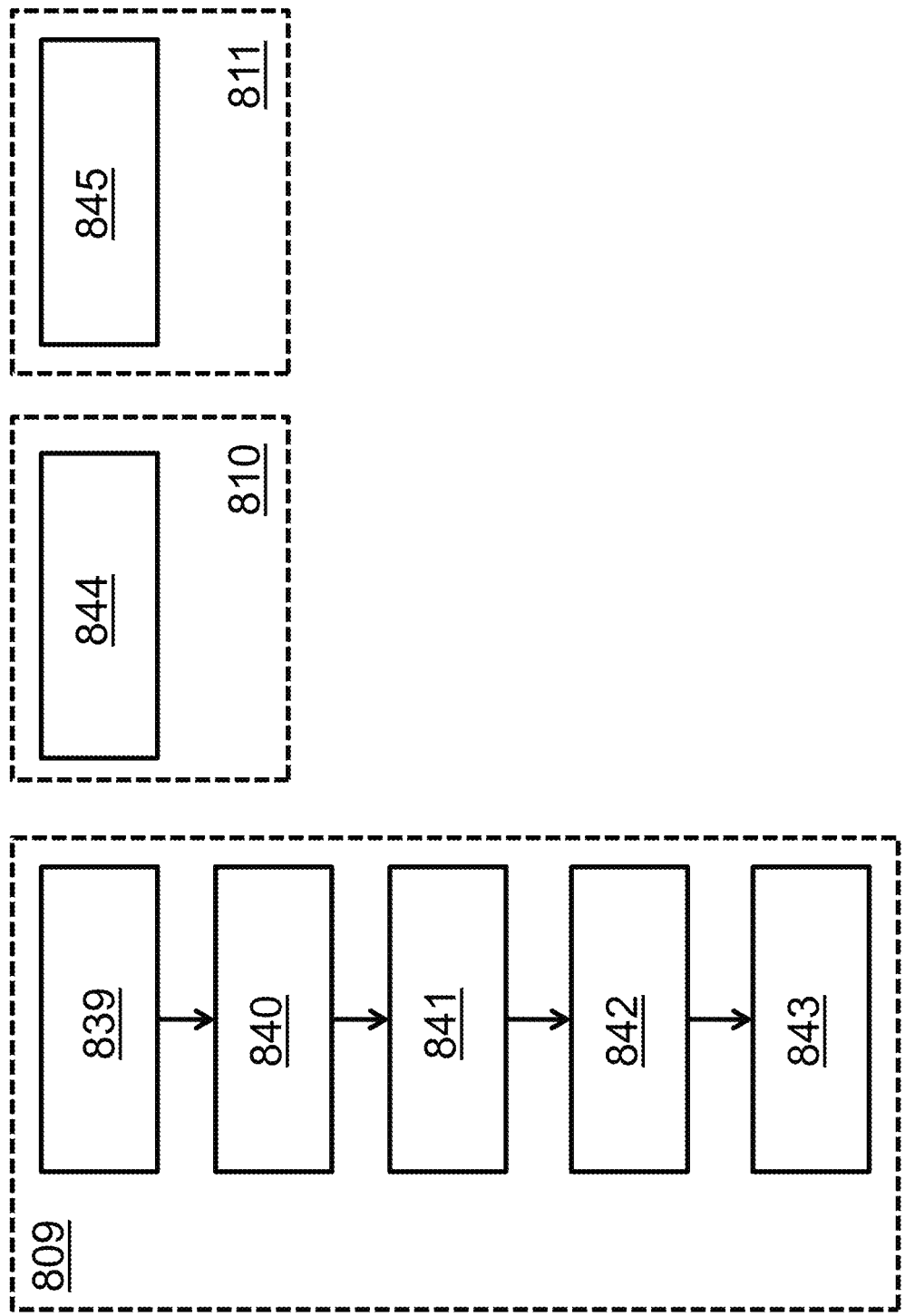
Figure 8E:
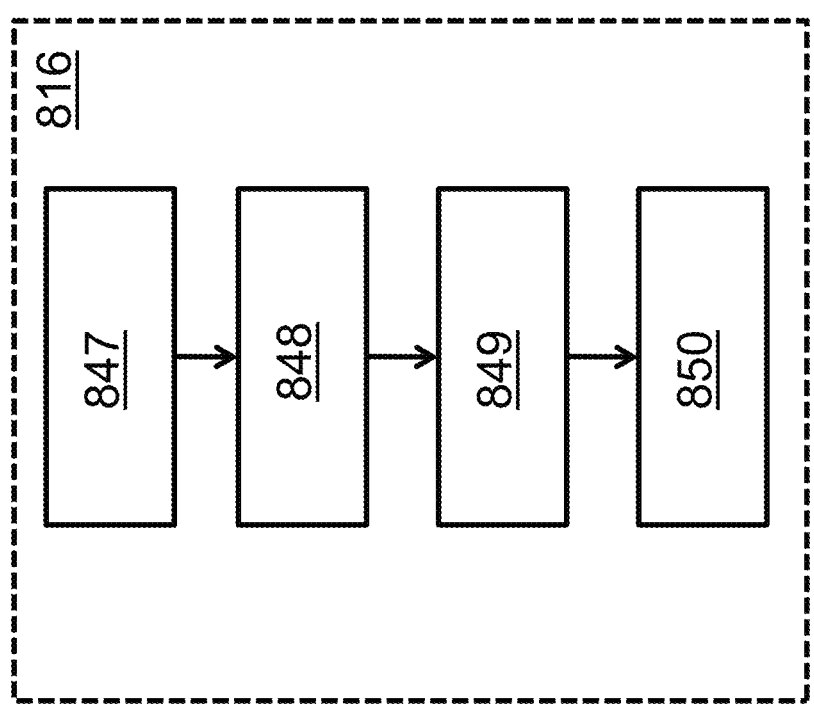

FIG. 8D illustrates that the text-mining step 809 can include aggregation 839, reading in the text of an article 840, parsing the read text 841, auto-assembling an XML version 842 and loading into a database 843. The ontology development 810 can include a Sort/Sift step 844 whereby objects (nouns), interactions (verbs) are sorted based on context with meta-data updated and synonyms analyzed to resolve conflicts. The pathway mapping step 811 can include an auto-assembly step 845 wherein the object/nouns are mapped as graphic nodes, the interaction/verbs are mapped as graphic arcs, and system and subsystem scaling is adjusted based on context.

Example 5. Automated Biomedical Research System

An embodiment provides for an Automated Biomedical Research System (ABRS) that can include a commercial module that can incorporate market economic analyses and approaches that can be combined into the research system to enhance the KB as well as the UI, QM and ExpDir functionality. Commercial and/or market inputs to the system can include market data on diseases, incidence, cost of disease, cost of treatment, duration of disease, duration of treatment, mortality, market positioning, FTO and IP positions, royalty requirements, competition, potential customers, customer budgets, sales cycles, phases costs, delay costs, budgeting per schedule considerations, cross-investment, ROI, contract requirements and other legal issues, risk factors, and other commercial and/or marketing factors.

Additional components of the ABRS system can include one or more of the following system elements:
(1) Computer System, with software operating system component
(2) User interface (UI) module and visualization component
(3) Query Manager module (with the UI generates user-specified goal (USG) instruction or directive)
(4) Database and Knowledge Base (KB) module
  (a) Domain literature Pathways component
  (b) Domain Manual Ontology component
(5) Experiment Director module
  (a) Experiment Chooser component
  (b) Sourcing decision component
  (c) Experiment Controller component
(6) Data Processing Module
  (a) Filtering component
  (b) Image processing component
(7) Data Analysis Engine
  (a) Data Mining component
(8) Modeling module
  (a) Knowledge Base Assembly Core Component
  (b) Simulation Component
  (c) Reverse-engineering component
(9) Congruence Module
(10) Simulation Module
(11) Commercial module
  (a) Business development transaction component (templates, forms, contact management, account management, RFPs, proposals, etc.)
  (b) Market analysis component
  (c) Sales/Marketing component (e.g., targets, quantities, timing, price points, etc., interfacing with commercial and Query Manager modules)
  (d) Legal component (IP, royalties, contracts, licensing, etc.)
  (e) Financial component (budgeting, risk analysis, cost analysis, etc.)
(12) Quality-control (fault tolerance) module Experiment Usage Rule Engine and Ontology Methods Inputs to the Experiment Usage Rule Engine can be stored using methods of building ontologies, such as XML, OWL, CORBA and other methods of software object and information object creation for use across distributed networks and/or within relational database structures. For instance, a general experimental procedure can be described in any number of approaches that are known to those skilled in the art of common ontologies and controlled vocabularies to enable data exchange for experiments, such as, for example, ontologies in the biosciences, which can be found by investigating:

Human Proteome Organization Proteome Standards Initiative standards for data transfer and deposition. These standards utilize ontologies and controlled vocabularies to describe experimental procedures and common processes such as sample preparation, such as the GO ontology and including nomenclature of the world's leading protein sequence database, UniProt, while incorporating and adding to the GO annotation of molecules described within UniProt-Swiss-Prot and UniProt-TrEMBL, also has its own defined keyword section that allows users to perform searches across the database using a standard nomenclature consistent to all entries;

A number of both commercial and academic molecular interaction databases that exist (IntAct, BIND, DIP, MINT, Hybrigenics, HPRD, MIPS) wholly or partially in the public domain; and The HUPO-PSI MI format that has been developed using a multi-level approach similar to that used by the Systems Biology Markup Language (SBML). Level 1, published early in 2004.

Ontologies can be integrated with the knowledge-base components of the invention by one having ordinary skill in the art, with guidance from the methods disclosed by "The Use of Common Ontologies and Controlled Vocabularies to Enable Data Exchange and Deposition for Complex Proteomic Experiments S. Orchard, L. Montecchi-Palazzi, H. Hermjakob, and R. Apweiler; Pacific Symposium on Biocomputing 10:186-196 (2005), hereby incorporated by reference herein in its entirety; http://helix-web.stanford.edu/psb05/orchard.pdf.

Several controlled vocabularies have been developed, including interaction type, feature type, feature detection method, participant detection method, and interaction detection method to describe specific aspects of both an interaction and the experimental methodology used to determine these, such as, for example:

"Minimum Information About a Proteomics Experiment (MIAPE)" document analogous to the MIAME requirements for a micro-array experiment, and both an object model (PSI-OM) and XML format (PSI-ML) to fully represent a proteomics experiment. PSI-GPS uses the modules such as the more specific mzDataformat as components of a full experiment description, comprising sample preparation, analysis technologies, and results. To delineate these processes, controlled vocabularies are written and appropriate terms contributed to the MGED Extended ontology under the "PSI" namespace. The MGED ontology is written to support the micro-array object model, MAGE. The extended version adds further associations and classes to the core ontology which is intended to be stable and fully in synch with MAGE.

National Center for Biomedical Ontology's BioPortal. BioPortal is a Web-based application for accessing and sharing biomedical ontologies.

Biomedical Informatics Research Network (BIRN) is a geographically distributed virtual community of shared resources offering tremendous potential to advance the diagnosis and treatment of disease. BIRN enhances the scientific discoveries of biomedical scientists and clinical researchers across research disciplines.

Features in BioPortal 2.0 include the XCEDE schema, which provides an extensive metadata hierarchy for describing and documenting research and clinical studies. The schema organizes information into five general hierarchical levels:
1. a complete project;
2. studies within a project;
3. subjects involved in the studies;
4. visits for each of the subjects; and
5. the full description of the subject's participation during each visit.

Each of these sub-schemas is composed of information relevant to that aspect of an experiment and can be stored in separate XML files or spliced into one large file allowing for the XML data to be stored in a hierarchical directory structure along with the primary data. Each sub-schema also allows for the storage of data provenance information allowing for a traceable record of processing and/or changes to the underlying data. Additionally, the sub-schemas contain support for derived statistical data in the form of human imaging activation maps and simple statistical value lists.

XCEDE was originally designed in the context of neuro-imaging studies and complements the Biomedical Informatics Research Network (BIRN) Human Imaging Database, an extensible database and intuitive web-based user interface for the management, discovery, retrieval, and analysis of clinical and brain imaging data. This close coupling allows for an interchangeable source-sink relationship between the database and the XML files, which can be used for the import/export of data to/from the database, the standardized transport and interchange of experimental data, the local storage of experimental information within data collections, and human and machine readable description of the actual data.

To facilitate the use of the XCEDE schema, a toolbox has also been developed based on XCEDE for the storage of neuro-imaging activation maps and anatomical labels. Also see: Astakhov V, A Gupta, J Grethe, E Ross, D Little, A Yilmaz, M Martone, X Qian, S Santini, M Ellisman (in press) Semantically Based Data Integration Environment for Biomedical Research. Proceedings of the 19th IEEE International Symposium on Computer-Based Medical Systems, in press. incorporated by reference herein in its entirety; Astakhov, V, A Gupta, S Santini and J S Grethe (2005) Data Integration in the Biomedical Informatics Research Network (BIRN), In: (B. Ludäscher, and L Raschid eds.) Second International Workshop, Data Integration in Life Sciences, San Diego, Calif., USA, Jul. 20-22, 2005. Proceedings. Lecture Notes in Computer Science: 3615:317; incorporated by reference herein in its entirety; and Grethe J S, Baru C, Gupta A, James M, Ludaescher B, Martone M E, Papadopoulos P M, Peltier S T, Tajasekar A, Santini S, Zaslavsky I N, and Ellisman M H (2005) Biomedical Informatics Research Network: Building a National Collaboratory to Hasten the Derivation of New Understanding and Treatment of Disease, Stud Health Technol Inform. 2005; 112:100-9; incorporated by reference herein in its entirety.

Example 6. 2-D Matrix—Type-1 Domain

User starts ARS program by turning on computer and opening the User Interface:
"Run ARS User Interface"

User chooses a Studied System Type from a standard pull-down menu displayed by the UI. In this example:
"Choose Studied System: Type 1, (ST-1)"
"If SS Type=ST-1, then load ontology 'ST-1: Virtual System; 2-dimensional grid', including terminology, rules and/or guidelines file or files for this SS domain (or software objects, which can include dynamic software sub-routines)"
(Here the domain ontology, rules and guidelines can be loaded into memory to provide the necessary terminology and a number of rules, principles, parameters, guidelines and/or other information to be drawn upon by the User Interface module, the Query Manager module, the Experiment Director module (including the Experiment Chooser module when choosing the preferred initial experiment), the Experiment Chamber, the DAE and the Congruence and Goal Completion testing modules in subsequent stages of the research process. In addition, or alternatively, the domain information that is loaded can include software objects that can have additional dynamic program capability to interact with the Query manager of the ARS and/or the User Interface and/or other modules of the ARS).

Figure 9A:
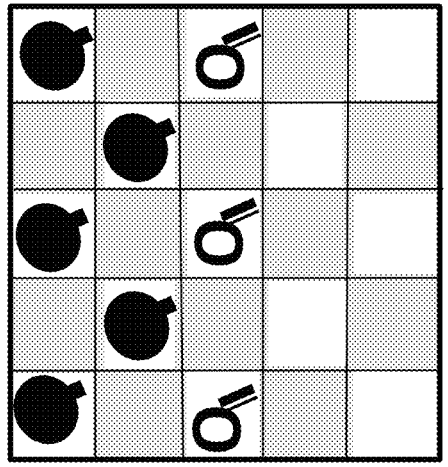
FIGS. 9A-9H illustrate further Type-1 experiment outcomes according to the invention.
Figure 9B:
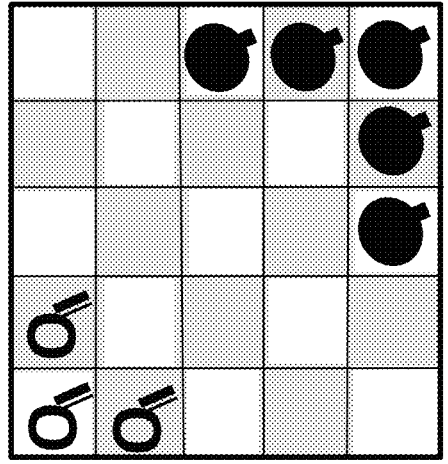
Figure 9C:
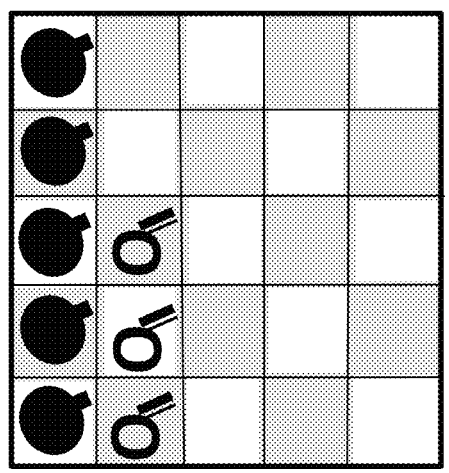
Figure 9D:
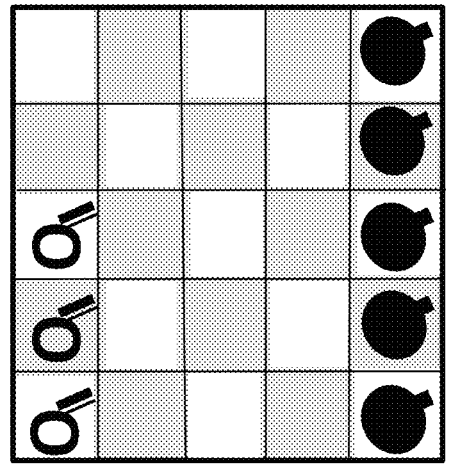
Figure 9F:
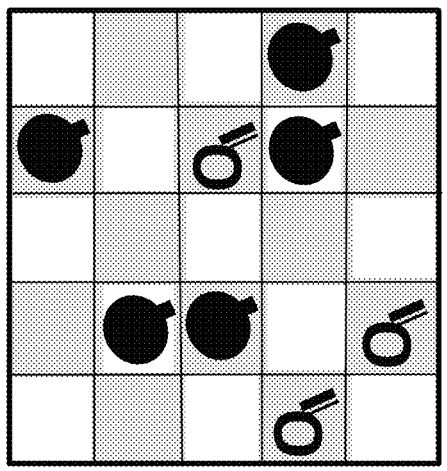
Figure 9H:
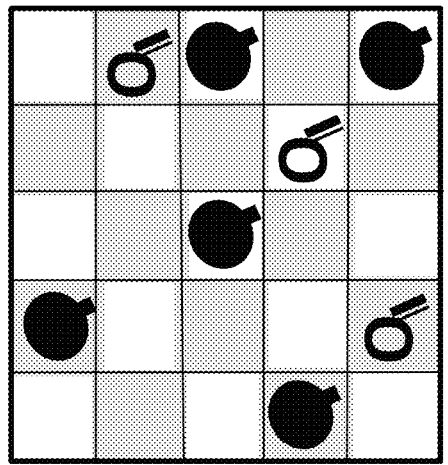
Figure 9E:
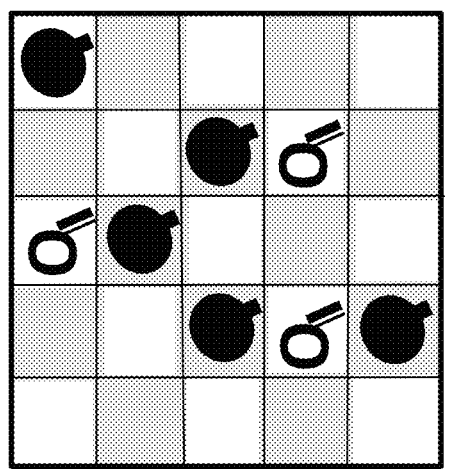
Figure 9G:
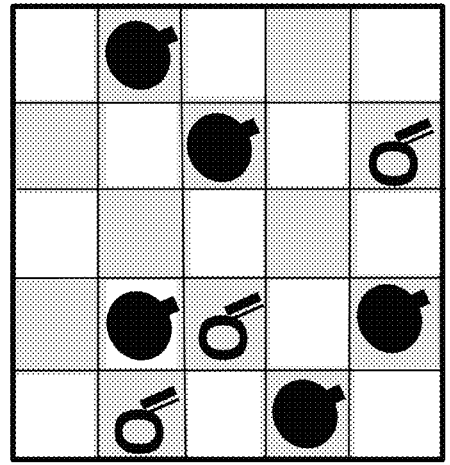

"Choose Studied System SubType=Chess"
(Here the User Interface can have subtypes in its datastore or can access a list of subtypes from the domain ontology accessed in the previous step).
"If SS Type=CHESS, then load 'Chess Manual' ontology, rules and/or guidelines file or files (or software objects, which can include dynamic software sub-routines)"
(Here further aspects of the domain ontology, rules and guidelines as may be more appropriate to the chosen sub-type can be loaded into memory to provide the necessary terminology and a number of rules, principles, parameters, guidelines and/or other information to be drawn upon by the User Interface module, the Query manager, the Experiment Director module (including the Experiment Chooser module when choosing the preferred initial experiment), the Experiment Chamber, the DAE and the Congruence and Goal Completion testing modules in subsequent stages of the research process).
"Set Scope/Size: 5×5 board
"Set Starting setup or constraints: 5 Black Queens and 3 White Queens
"Set Research Goal Type(s): (a) test/find corrective and (b) optimize
"Set Goal-Subtype '(a) test/fin corrective': Defensive Position Test/Find
"Set '(b) optimization level': 100% optimization
"Set Optimization definition or parameters: No threats"
(Here the User Interface can be using goal-setting guidelines from a portion of the "Chess Manual" domain manual, such that the manual can pass to the User Interface module the required scoping queries for the user's responsive entry to create the USG directive).
It will be appreciated that a User Interface module can be written to retrieve directly domain ontology information from anywhere on the Internet (or other network or electronic data pathway) and/or a Query Manager module can be provided that interfaces with the User Interface and other of the ARS modules and $3^{rd}$-party information sources and that assists in handling input-output queries and responses between the User Interface and the one or more libraries of domain information (such as, for example, domain libraries distributed on the Internet, that may utilize XML, CORBA, OWL, DAML+OIL, RDF schema and/or other information technologies).
These additional query formulations retrieved from the ontology and/or guideline files can be provided to the user through pull-down menus in the User Interface. For example, the Chess Manual ontology can provide information that Test/Find experiments can include 'Defensive Position' tests for which an optimization pathway can be selected as "No threats" between the black and white chess pieces.
The above goal specification now comprises the user-specified goal (USG) for one or more iterations of the ARS in this embodiment, where the SS type (and/or subtype) is the domain of chess (or, even more specifically, the domain of a subset of a chess-board space, i.e., the regular 8×8 square board reduced to a 5×5 square board).
"Run Experiment Director," which reads the USG file directive.
(Upon initiation, the ARS will pass the USG information to the Experiment Director (either directly or via the Query Manager module), which has methods and modules that can be further illustrated here in pseudo-code, below, from which one skilled in the art can program in a number of possible computer languages and implement in a number of alternate combinations of computer system and software that can be connected to an experiment chamber by electronic communications, e.g., by the Internet, LAN, WAN or other well-known means):
"USG passed to the Experiment Chooser module of the Experiment Director module:
"Experiment Chooser analysis:
"If SS subtype=5×5 board, then include constraints of the 5×5-board subset of the 'Chess Manual' rule and guideline file"
(Here a sub-domain of the Studied System can be matched to include specific additional constraints, rules or principles from subsections of the domain manual, or subsections of the domain knowledge base)
"If Exp. Stage/Goal in the USG=Protective, 100% optimize, then load Position and Threat Analysis subset of EOs in the LOPE that pertain to this SS-1-Chess subdomain."
(Here, in this example, based on the USG directive, which can include parameter codes declaring the goal of protective (no threats) at 100% optimization, the Experiment Chooser leads to selection of at least one Experiment Object from the LOPE for this SS chess domain, as described below).
"If Start Constraint=Queen components, then load Queen behaviors"
(For this example, the starting constraint has been to load 5 Black Queens (BQ) and 3 White Queens (WQ), or to conduct experiments with these components, which then leads to an instruction to load from the knowledge base the known behaviors and rules associated with these components, i.e., a Queen can move or threaten any square in view along a column or a rank or along a diagonal.)
"SELECT LIST and DESCRIPTION of POSSIBLE EXPERIMENTS from the LOPE and LOAD to Experiment Director/Experiment Chooser"
In this example, for illustration, the Experiment Chooser module loads descriptive information for three Experiment Objects categorized under "SS-1:Chess: 5×5 board-Queens-No-threat goal" that show in their data and procedural description the ability to search for no-threat protection:
"→SS-1:Chess: 5×5 board-Queens-No-threat goal: Exp.#1: 5 BQ, 3WQ . . . initial condition load components B1, B2, B3, B4, B5, W1, W2, W3 into board positions a5, b5, c5, d5, e5, a4, b4, c4, respectively. Evaluate, testing for threats"
(i.e., testing if any BQ and WQ component exist on same file (column), same rank (row) or same diagonal).
"If TEST=YES, then modify positions by RULE 1.1, RULE 1.2 or RULE 1.3. If TEST=NO, then STOP and REPORT SUCCESS; VOI=Low; Time requirement=High"
(See FIG. 9A as illustration of the starting position of Experiment #1, where RULE 1.1 can be to increase spacing between each component sequentially along the rows, which would produce the pattern in FIG. 9B, or RULE 1.2 could specify changing positions until maximum separation by rows between black and white components, leading to FIG. 9C, or maximum separation by diagonals, leading to FIG. 9D).
"→SS-1:Chess: 5×5 board-Queens-No-threat goal: Exp #2: 5BQ, 3WQ . . . initial condition set as random placement of all components. Test for threats. IF TEST=YES, then modify positions by RULE 2.1 (restart). If TEST=NO, then STOP and REPORT SUCCESS. VOI=Low; Time requirement=High (See FIG. 9E-9H for illustrations of the progress of Experiment #2, where RULE 2.1 is simply to reset the position by random placement).

"→SS-1:Chess: 5×5 board-Queens-No-threat goal: Exp #3: Use knowledge base of chess guidelines and principles to initiate placement. Start with RULE 3.1—choose smaller of component sets, {WQ} versus {BQ}, resulting in choice of {w}, and place WQ1 on weakest of queen positions to yield maximum number of unthreatened squares"

Figure 10A:
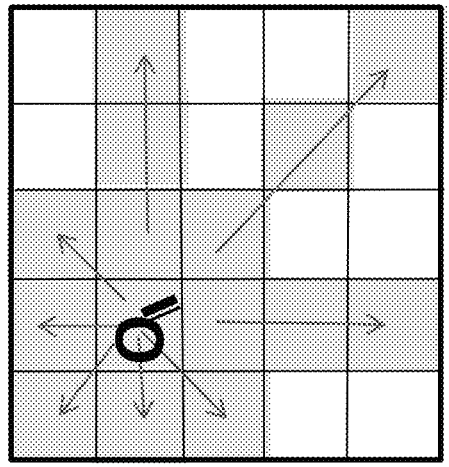
FIGS. 10A-10F illustrates additional Type-1 experiment outcomes according to the invention.
Figure 10B:
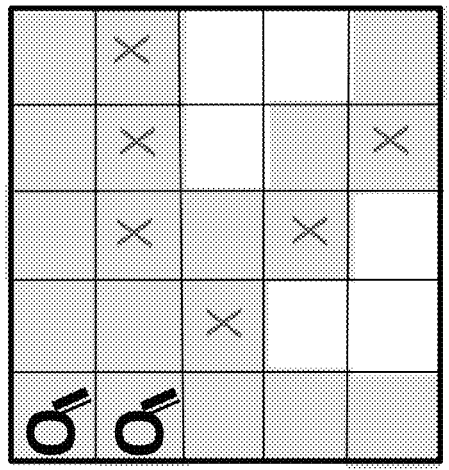
Figure 10C:
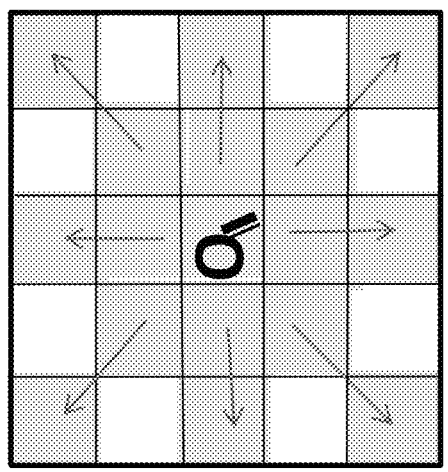

(Chess manual shows FIG. 10A-10C, which results in choice of FIG. 10C initial position, yielding 12 unthreatened squares.)

"CONTINUE. Place WQ2 on remaining weakest position, using chess manual principle that REDUNDANCY with coverage of WQ1 should be maximum and to maximize remaining unthreatened squares at greater than or equal to 6 unthreatened squares,"

Figure 10D:
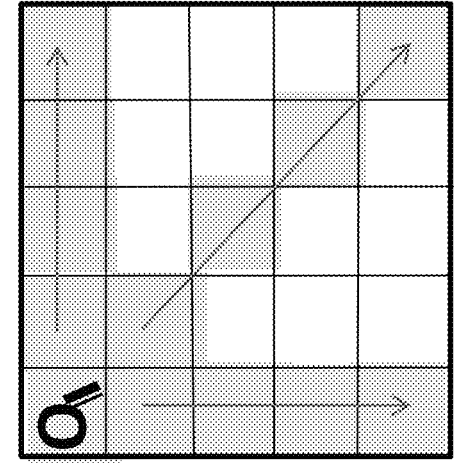

(which can result in position of FIG. 10D).

Figure 10F:
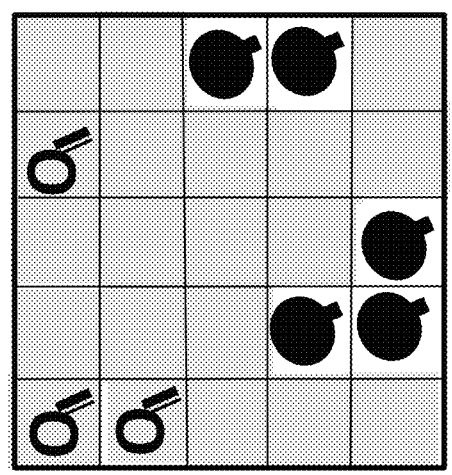
Figure 10E:
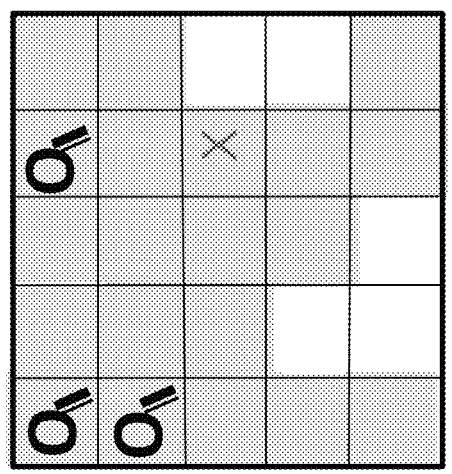

"CONTINUE. Place WQ3 on remaining weakest position (which can result in position of FIG. 10E), using chess manual principle that REDUNDANCY with coverage of WQ1 should be maximum and to maximize remaining unthreatened squares at greater than or equal to 5 unthreatened squares. TEST for threats. If TEST=YES, then report NO SOLUTION. IF TEST=NO, then STOP and REPORT SUCCESS (such as position of FIG. 10F).

(Note that FIGS. 10C-10F represent progress of Experiment #3. It can be seen that the steps of RULE 3.1 can be programmed rather easily by testing for unthreatened squares. In the final step the routine need only search for the column and/or file having only one open (unthreatened) square and test these two possibilities (positions c1 and d3) for solution. Thus, this Experimental Object converges very rapidly to a solution (i.e., toward meeting the USG).

"VOI=High; Time requirement=Low"

"(OPTIONAL) Evaluate VOI for each OE extracted from the LOPE"

"(OPTIONAL) Evaluate Cost, safety and time requirements for various OEs extracted from the LOPE"

"CHOOSE EXPERIMENT OBJECT (Rule-based procedure in the Experiment Chooser module)

"if single result produced from LOPE, then choose that OE

"if multiple possible OEs, then choose highest VOI; if equal VOI then select at random "if ZERO possible OE choices, then automatically loosen Chooser constraints (e.g., loosen VOI constraints, time, safety) and search again for a possible OE (Report to USER)

"if still ZERO possible OE, then return to USER, report and stop." "LOAD OE-Chosen"

(Based on the above criteria, because it has the highest VOI score, the Experiment Chooser will load Exp #3).

"RUN EXPERIMENT OE-Chosen

Running the OE-Chosen activates other program modules in the Experiment Director module, which can include, inter alia, passing control to the Experiment Director Run Module that will direct the initiation of the experiment based on the data in the EO-Chosen.

In at least one embodiment of the invention the Exp Director first checks to see it the EO-Chosen is a 'self-running' experiment type that can substantially direct its own initiation and progress (such as, for example, a software program contained in the EO-Chosen software object that knows the location of its intended Experiment Chamber, contains all necessary instructions for initiation and will itself direct the progress of the experiment).

In other embodiments, the Experiment Director can gain information from the EO, then based on that information seek an Experiment Chamber appropriate for executing the EO from a number of Experiment Chamber providers (such as available labs within one company, or from multiple CROs available at differing geographic locations), and then the Experiment director remains in control as to initiation and procedure of the experiment, taking from the EO-Chosen only static data as required by programs running in the Experiment Chamber.

"After each experiment step, evaluate progress and loop to next experiment stage"

(Here the Experiment Director may have interim progress-checking steps in the procedure of the experiment, which may or may not include accessing the DAE for interim evaluation).

Preferably, the Experiment Object that is chosen to run will have as much of the programmatic control of the experiment built in as practicable (described as "process and chamber complete"). An EO that is process-complete and chamber-complete will only require the Experiment Director to pass to the EO the USG directives and other information from the domain ontology manuals that may be held by the Query Manager and the Experiment Director modules. Preferably the EOs will have their own capability to access their full domain knowledge bases directly.

In building efficiency into the ARS, it will be advantageous to minimize the amount of information that must be stored within the Experiment Director module, allowing as much of the procedural information and experiment-control routines as practicable to be maintained within the EOs themselves.

"Create Data and pass data to the Data Analysis Engine (DAE)"

In the current example, the EO is a virtual experiment that can be implemented in an automated computer program that runs the instructions of the experiment. It is a straightforward for a software program to carry out the simulation of setting piece positions in a 5×5 matrix and testing alignment of B versus W pieces along rows, columns and diagonals, with each test producing a data result that is reported to the data analysis engine (DAE). Alternatively, the Experiment Director could send the directions of the experiment to an Experiment Chamber in which robots or human technicians manipulate the pieces on an actual chess board and detect the presence or absence of threats, reporting these results to the data analysis engine (DAE).

In this example, running experiment #3, the domain guidelines (Chess Manual) instruct a first positioning of first white queen on an edge square. With 16 different possibilities, there can be 16 iterations of placing the first piece and measuring a data result of the location and total number of non-threatened squares. The DAE can return through the Experiment Director an evaluation that every position yields coverage of the square upon which the piece sits plus 4 diagonal squares, 4 row squares and 4 column squares, for a total of 13 covered squares, always yielding 12 non-threatened squares. Thus, the DAE program can choose any one of these positions as being fairly equal; however, here the domain manual guidelines may influence this choice by pointing to an edge square that cannot reach the center square in a single move as being a weaker placement, such that the Experiment Director can instruct the placement of the next piece. Note however, that here the Experiment Object can be using the domain manual guidance and it will be appreciated here that an EO that is a stronger software object itself may contain within its EO programs the capability to perform the interim positional analysis and guided placement of the subsequent pieces, so that the DAE and Experiment Director may be bypassed during these experiment steps).

"ANALYZE RESULT and test against GOAL

"Pass result/evaluation to Data Analysis Engine (DAE) and then to Congruence Module to evaluate results progress against goal.

"If GOAL not reached, then ITERATE

"If GOAL reached, then STOP"

(In the case of the current example of "SS-1:Chess: 5×5 board-Queens-No-threat goal: Exp #3", the result at each step is evaluated for completion against the goal. The experiment procedure calls for continuing until the three white queens are placed, and the test results at this stage must show 5 non-threatened squares to provide a successful 100% optimization).

At the end of the placement of the $3^{rd}$ white queen, the DAE passes the outcome solution to the Congruence Module, which compares the USG to the experiment result. If no gap exists between the result and the goal, then the ARS sends a completion report to the user and the program stops.

With multiple pathways possible in the experimental procedure of Exp #3, an unsuccessful result of one experimental cycle can lead to the Congruence Module passing the control back to the Experiment Director with an instruction to restart, whereupon the Experiment Director can add as a constraint the rule to exclude any exact repetition of the prior experimental pathway. This 'variation of parameters' approach can include many appropriate methods from Monte Carlo research approaches as well as from many approaches to finding mathematical solutions to problems by iteratively varying parameters in certain equations and testing for solutions.

Experiment Object Description

Each Experimental Object will have Value-of-Information properties, related to the set of experimental outcomes of that experiment, the probability associated with each of those potential outcomes and an expected value associated with each particular outcome.

Example 7. Experiment Objects—Type-1 Domain

In this Type-1 domain example, each experiment object is constructed for a particular Experiment Template, and supports the following operations:

Set parameter values. (Each Experiment Template defines a set of parameters which distinguish one Experiment Object instance from another.

Calculate Expected Outcome Set, given upper bound on number of outcomes desired.

Execute experiment and produce an Experiment Outcome.

An Experiment Outcome has the following operations:

Update Knowledge Base with results of experiment

General Framework for Experiment-Related Object(s)

Experiment:
A System State Specification (such as an initial condition, or starting state)
A System Modification Specification
Expected Outcome of experimental procedure
Experiment Outcome Object:
Experiment Result.
Progress Measure.

Expected Outcome Set:
List of Experiment Outcome Objects $O_i$
Estimated probability $P(O_i)$ that each particular outcome will occur.
VOI score $V(O_i)$ associated with each particular outcome=$P(O_i)\times$the Progress Measure of $O_i$.
VOI (Exp)=SUM over all outcomes of Product of Probability of an outcome occurring, Pr (Outcome i) and the VOI (outcome i)

Experiment-Related Object Framework for Chess Problem Example

Experiment Object Properties:
A Board State Object.
Specification of the move: $(x_1, y_1) \rightarrow (x_2, y_2)$.
Board State Object Properties:
List of board positions (x, y) for each queen.
Experiment Outcome Object Properties:
Board State Object represented.
Progress Measure: the number of unthreatened queens.
Expected Outcome Set Properties:
List of Experiment Outcome Objects $O_i$, sorted by decreasing total number of threats $T(O_i)$.
VOI associated with each Experiment Outcome Object (this will be set to the total number of threats $T(O_i)$ for each Experiment Outcome Object $O_i$.
Knowledge Base Object:
Map from Board State Objects to number of unthreatened queens.
List of Board State Objects, sorted by decreasing number of unthreatened queens.

Algorithm for calculating expected outcome set for a given Experiment Object E:

1. Read upper bound on number of outcomes desired as N.
2. Create an empty list L of N/8 Board State Objects.
3. For all moves $(x_1, y_1) \rightarrow (x_2, y_2)$ which are valid for E's Board State Object:
4. Apply the move to get resulting Board State B.
5. If B is not already in the Knowledge Base, then
6. Calculate T(B) as the number of threats in B.
7. If there is a Board State C in L such that T(B)<T(C), then:
8. Add B to L, replacing C if L is already full.
9. Loop back to step 3.
10. Create an empty list R of N Experiment Outcome Objects.
11. For all Board States B in L:
12. For all integers i from 0 up to 8:
13. Add an Experiment Outcome Object consisting of B as the Board State and i as the number of unthreatened queens to R.
14. Loop back to step 12.
15. Loop back to step 11.

Example 8. Application Example for Business Method and ABRS Use in Drug Screening An embodiment of the invention further provides for a user to interact with a Query Manager module, as illustrated by the following 'pseudocode' examples of partial scoping selections (where user response choices are indicated inside "quotation marks"):

Set Goal: "Select and prioritize lead compounds through an efficacy screening assay"
Set Sub-Goal: "Use gene and protein expression profiles to screen for efficacious compounds"

Set Domain "Biomedical—Drug Discovery and Development Pipeline"
Set Research Phase: "Late Discovery/Lead Prioritization"
Set KeyWords and Phrases: "Lead Selection, Lead Compound Screen"
Set Research Participants:
  "Scientists involved in high-throughput screens (HTS)"
  "Drug discovery scientists"
  "ADME scientists"
Set EO Choice Parameters:
  "Compounds from purchased combinatorial libraries"
  "FTO eligible composition-of-matter"
  "efficacy"
  "patent rights"
  "one organ system"
  "liver"
  "in vitro assay"
Set Budget parameters: "$ XXX dollars"
Set Deadline: "6 weeks"
Set Database: "Biomedical Ontology KB-01"
Set KB Integration "Genomics, Proteomics, Metabolomics, Pharmacogenetics"
Set dimensionality: "6-D parameters; 10,000 limit each"
Set EO Type: "HTS assay"
Set ExpChamber Type: "Robotic"
Set DAE parameter: "[Autoselect]"

The above example of Query Manager settings chosen by the user (which can comprise the User-Specified Goal (USG) directive to the Query Manager and the ExpDir Modules) are meant to be illustrative only and are not meant to limit in any way the number, type, extent, form or format of the range of potential user-interface interactions that could occur between the user and the Query Manager in various embodiments of the invention. For example, one preferred embodiment can provide further interaction in the form of feedback from the Query Manager to the user that extracts from experiment and/or research guidelines and/or tutorials that are stored in the system's knowledge base (KB) and/or on other distributed KBs within the research potential of the studied system domain. Furthermore, the Query Manager in various embodiments can provide functional interaction with the data residing in various Experiment Objects as they rise toward selection by the Experiment Chooser component. For instance, information about potential assay CROs or collaborative laboratories could be returned to the user:

QM/ED RESPONSE: "Companies that have some assays in place:"
  "Avalon (Taqman screen)"
  "Pfizer/Pharmacia (P450 metabolism assay)"
QM/ED RESPONSE: "SNPs screening solutions off-the-shelf OTS:"
  "Orchid"
  "Luminex"
  "Sequenom"

Such feedback to the user can be drawn from data resident within the EOs within the LOPE (which can be distributed on the network) or can be derived by a sophisticated version of the Query Manager itself by accessing network information based on parameter selection in the USG and information developed from the EOs through the Experiment Chooser component.

Figure 11:
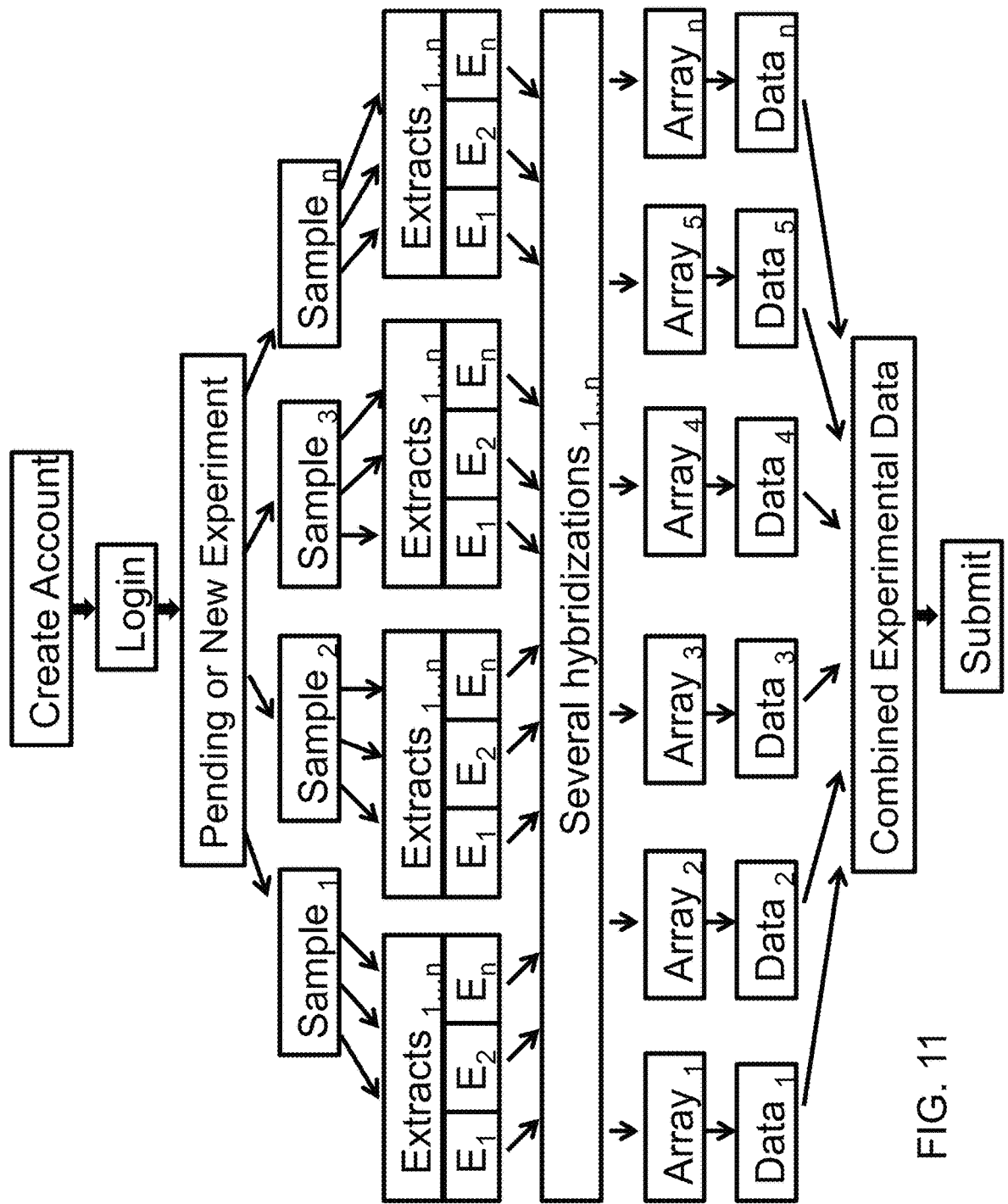
FIG. 11 illustrates aspects of a business method for automated research system services according to an embodiment of the invention.

Example 9. ExpDir and Exp-CTRL Controlling ExpCH, Receiving Data and/or Passing Data to DAE FIG. 11 illustrates a series of steps in how the Experiment Director of an ARS such as provided by an embodiment can access a control account for an automated research laboratory, where the laboratory can offer high-throughput microarray experiment services and can employ the industry standard 'Minimum Information About a Microarray Experiment (MIAME)' data/service interoperability protocol. Beginning at the top of the graphic and moving down by rows, the Experiment Controller can create an account with the automated laboratory, login, enter a description of a pending or new experiment, enter descriptions for sample (1), sample(2) through sample(n) with treatment protocols for each sample, declare the extraction protocols, which can be multiple for each sample, declare labeling and hybridization protocols for several different hybridizations, which then flow into potentially numerous different array designs, then each array can output data according to a specific image analysis protocol, combining experimental data using a transformation protocol and finally submitting the data back to the ARS Experiment Controller and/or to the ARS data-analysis engine.

Example 10. Use of DAE with SLAM for QSAR Screening Analysis

Modeling the Descriptor/Activity Relationships in their Full Complexity

Typical QSAR applications use standard linear or near-linear correlation analysis methods to predict activity from compound descriptors. Owing to real biochemical/biological complexity, QSAR relationships can be reasonably expected to be nonlinear with respect to compound descriptors. One ABRS method according to an embodiment of the invention includes a number of components to perform nonlinear modeling of predictive tasks. Combined with the identification of key descriptors, these nonlinear methods can provide a substantial improvement in screening accuracy.

Greedy regression approaches are based on additive or linear relationships between the individual predictors, i.e., relationships that require the predictive descriptor sets be decomposed into separate partial predictors. One ABRS according to a preferred embodiment of the invention provides methods that are universally combinatorial, and therefore do not require that the predictive sets be decomposed into individual components that are partial predictors separately. Such an ABRS according to an embodiment of the invention can also deliver small sets of descriptors that have the same or greater predictive power as much larger sets. Furthermore, focusing on a small set of combinatorial descriptors facilitates rational chemical interpretation and enables the downstream, more traditional QSAR computations to run faster and with better predictive performance.

Statistical Validation of Predicted Patterns

Valuable predictive patterns should be indicative of chemical/biochemical/biological relationships, and should not be the result of chance juxtapositions of values. The ABRS system includes numerical approaches based on cross-validation and permutation computational studies on real data to measure the degree of chance generation of patterns as a means of providing statistical validation.

In addition to pattern recognition methods, one embodiment of the invention provides a combination of sublinear association mining (SLAM) data mining methods (such as can be found and provided through the GeneLinker™ Platinum data analysis package, sold through Improved Outcomes Software, Kingston, Ontario, CA) with compute-intensive cross-validation for multivariate, multiclass Bayesian inference of outcome probabilities, such as is found in the Integrated Bayesian Inference System (IBIS™, available through Biosystemix, Ltd., Kingston, Ontario, Canada), allowing the DAE to distinguish chance occurrences from predictive effects rooted in biology.

Additional data analysis methods and algorithms that can be incorporated in the Data Analysis Engine according to one or more embodiments of the invention include: LDA and QDA-based, univariate and multivariate PIA (Predictive Interaction Analysis—inferring interactions through outcome discrimination and prediction), pair-wise gene-gene (variable-variable), combinations predictive of outcome, prioritized according to comprehensive statistical scoring, CPIA (Competitive Predictive Interaction Analysis), SPIA (Synergistic Predictive Interaction Analysis); TEA (Theme Enhancement Analysis—linking data-supported biological functional themes to outcome discrimination and prediction), statistically-supported enhancements of informative gene groups; P12 (Pathway Interaction Inference) through combined PIA and TEA, inference of competitive and synergistic pathway interactions, associations of pathway interactions with clinical and biological outcomes; Gene Network Reverse Engineering, cofluctuation analysis (associations across time, or condition, or assay, etc), continuous analysis, discrete analysis, linear and nonlinear analysis, multivariate analysis, cluster analysis, graph analysis, clique (identity cluster) extraction, multi-input graphs; ANOVA, F-test, multi-class tests, T-test, 2-class tests; MANOVA (multivariate ANOVA), 2-class tests, multi-class tests; Chip and class similarity analysis, Pearson correlation, Euclidean, other similarity measures as needed, Concordance, means of class-distances, distances of class-means; Discriminant Analysis, LDA (linear discriminant analysis), QDA (quadratic discriminant analysis), 2-class analysis, multi-class analysis, univariate, multivariate, all of which can be found through Biosystemix Ltd., Kingston, Ontario, Canada; http://www.biosystemix.com/pioneering %20applications %20and %20technology.html Reverse Engineering methods can be included by a programmer skilled in the relevant art utilizing the methods available above, as well as following the methods in D'haeseleer et al. (See "First data-driven, reverse-engineered model of gene interaction networks derived from measured, high-fidelity gene expression data: D'haeseleer P., Wen X., Fuhrman S., and Somogyi R., (1999) Linear Modeling of mRNA Expression Levels During CNS Development and Injury. Pacific Symposium on Biocomputing 4:41-52, the teachings of which are incorporated herein by reference in their entirety.

Example 11. Experimental Domains for Studied Systems—Biology Domain Manual and Knowledge Base Content A preferred embodiment of one Automated Research System according to the invention provides for a Biological Annotation and Pathway Modeling Library having domain Knowledge Bases for at least a set of model organisms commonly used for research in biology, such as the following listed in Table 1.

TABLE 1

Model Organisms for which Annotation and Pathway Modeling Knowledge Bases are included in a Domain Manual Knowledge Base in a preferred embodiment and which can be part of the available experimental resources of a participating automated laboratory.

| | | |
|---|---|---|
| E. COLI | Escherichia coli | common intestinal bacterium that can cause diarrhea disease |
| S. CEREVISIAE | Saccharomyces cerevisiae | single-cell eukaryote, yeast known for role in bread and beer production |
| S.S. POMBE | Schizosaccharomyces pombe | single-cell eukaryote, yeast known for role in bread and beer production |
| C. ELEGANS | Caenorhabditis elegans | tiny, soil-dwelling worm |
| D. MELANOGASTER | Drosophila melanogaster | ubiquitous fruit fly; |
| D. RERIO | Danio rerio | zebra fish |
| A. THALIANA | Arabidopsis thaliana | small weed that models for the plant kingdom |
| M. MUSCULUS | Mus musculus | house mouse |

It will be appreciated that the above Table 1 is illustrative rather than limiting, such that much longer lists of potential experimental organisms could be part of the available resources for an automated experimental laboratory process and, similarly, extensive lists of additional strains, plasmid, compound, materials and/or other bio-component libraries suitable for use in laboratories can be included.

Example 12. Method for Automated Design of HTP Experiments in Connection with a Computational Biology Learning System In this example, a preferred embodiment of the invention further provides for an automated laboratory (or an automated experimental chamber, or a research robot), with certain experimental resource libraries accessible (such as model organism, strain, plasmid, compound, materials and/or other bio-component libraries), into which are connected directives from automated experimental design components parsing Chosen Experimental Objects (CEOs) and from which automated laboratories' results are passed to data analysis, modeling and simulation components.

In this preferred embodiment, the invention further provides for an integrated experimental, modeling and management optimization system, with automated and goal-seeking feedbacks between experiment control, experimental results, modeling control, modeling results, query control and query results, connecting to libraries of available resources and constrained by self-knowledge (the automated research system itself knowing) of available resources.

The invention further provides for integrating scientific observations (or monitoring) with modeling and with artificial intelligence assisted management and/or decision-making methodology. This methodology can include adjusting data-gathering in response to output from modeling modules (modeling layer) and a manager's queries (e.g., the user's USG submitted through the Query Manager module).

The Integrated Management, Modeling and Measurement (IM3) methodology according to an embodiment of the invention (a) translates into computer form the mental models of managers, (b) merges the formalized mental models with prior and currently generated scientific models for explaining relationships and dynamics in gathered and/or measured data, (c) makes the merged modeling layer transparent and accessible to managers and adjustably and robustly responsive to their queries, and (d) designs the data-gathering (automated experimental sampling and/or observation) to be flexibly and rapidly adjustable to the data needs of the modeling layer as determined by the Congruence Module and Modeling Module in juxtaposition with the User-Specified Goal statement and the Query manager and thus to the manager's queries as the manager anticipates a decision.

Example 13. AIM3 Research and Management in Area of Environmental Change

An Automated, Integrated Monitoring, Modeling and Management (AIM3) methodology according to the invention can be applied to interdisciplinary study of and assessment of the potential impacts of environmental change on society at varying scales in service to decision-making. As shown in FIG. 1, two dimensions of an integrated assessment in the context of climate change can be visualized. One dimension can be thought of as a "vertical integration" that rises from studying causes and impacts through estimating risk and potential responses and then through decision-making to arrive at actual responses. Another dimension can be illustrated here as a "horizontal integration" of submodels for geospatial dimensions, resource sectors and impact types that can be related to each level of the vertical integration. This horizontal integration combines many physical and socio-economic aspects of a regional case study that can be seen to interact on a geographical scale. Regional, econometric input-output models, for example can be built for each economic sector and their interactions with each other and with environmental changes mapped through a geographic information system (GIS).

Referring again to FIG. 1, an AIM3 assessment approach for examining Climate Change Impacts according to an embodiment can include an integration along one dimension, from observing causes and gathering data, through modeling risk and potential response analysis, to making decisions and actual responses, while an integration along another dimension (depicted as horizontal) combines research on physical and socio-economic aspects as they compound and interact on various geographical scales.

Adjustable Data-Gathering Responsive to Modeling Layer and Manager's Queries

As a manager anticipates a decision, he or she is motivated to gather useful information upon which to predicate that decision. This information can be made part of the manager's mental model or set of mental models, a process that may be assisted by incorporating the information into computer models (which may be expert systems) to derive secondary information that will guide and/or alter the manager's mental model(s). It is useful to design the data-gathering process to be flexibly and rapidly adjustable to the data needs of the modeling layer. Further, the data-gathering step can be made adjustable in response to a manager's queries: the ARS environmental modeling module can include a 3-dimensional, geodynamic, environmental modeling system in its modeling layer, which can respond to a manager's query (for example, from user-specified goal (USG) directives), with the system able to recognize its data needs relative to the USG objective function and to adjustably instruct the data-gathering process via the Query Manager and the Experiment Director in at least one embodiment.

Figure 12:
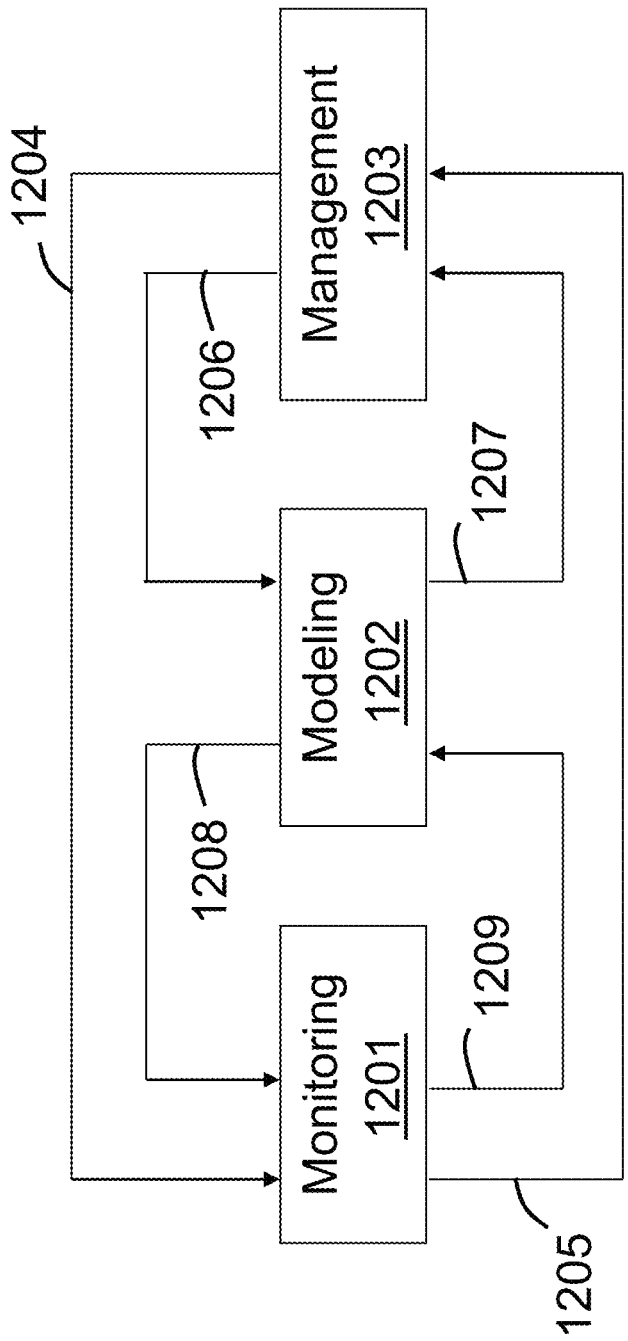
FIG. 12 illustrates aspects of a general integrated monitoring, modeling and management (IM3) methodology that can be automated according to an embodiment of the invention.

Referring to FIG. 12, in a traditional method of decision-making, managers direct an information-gathering step 1204, which may include monitoring or measuring, whereupon the information is returned to the managers in step 1205. With the advent of numerical modeling, management began to pass the information to a modeling group, as in step 1206, and the results of the modeling would be returned to managers in step 1207. Integrating the monitoring, modeling and management methodology gives the modeling division and/or the modeling objects various degrees of control over the monitoring process in step 1208, and brings the data back to the modeling process in step 1209. Then, automating the research system with software objects that enable almost any user to have rapid access to a wide variety of experimental techniques and automated laboratories provides a further efficiency and acceleration to the methodology, such that automated, integrated monitoring, modeling and management (AIM3) methods according to an embodiment of the invention, can provide a dramatically improved and powerful manner of conducting research on a wide variety of systems.

In an iterative learning model according to an embodiment of the invention, an automated modeling-monitoring control linkage can be connected to a rules-based, guidance module, such that the data-gathering (which can be lab or field experimental, or ongoing monitoring) can be automatically redirected by the guidance module based upon the robustness of the result being created with the modeling routine. This can be related to a Monte Carlo, iterative modeling exercise, where a series of parameter inputs are altered during a series of model runs to test sensitivity and robustness, except that in the AIM3 approach, instead of artificial inputs the model is receiving a variation of measured and/or gathered data. In fact, the two approaches can be used together effectively, where variation of parameters to yield a range of results can, through the rules-based guidance module that evaluates value of information related to the expected value of potential experiment outcomes, determine the next-desired set of actual measurements to be obtained. In this fashion, the value of data gathered is maximized and the modeling effort is able to focus more rapidly on a particular response to a particular query.

Example 14. Environmental: AIM3 Research and Management in River Systems

Figure 13:
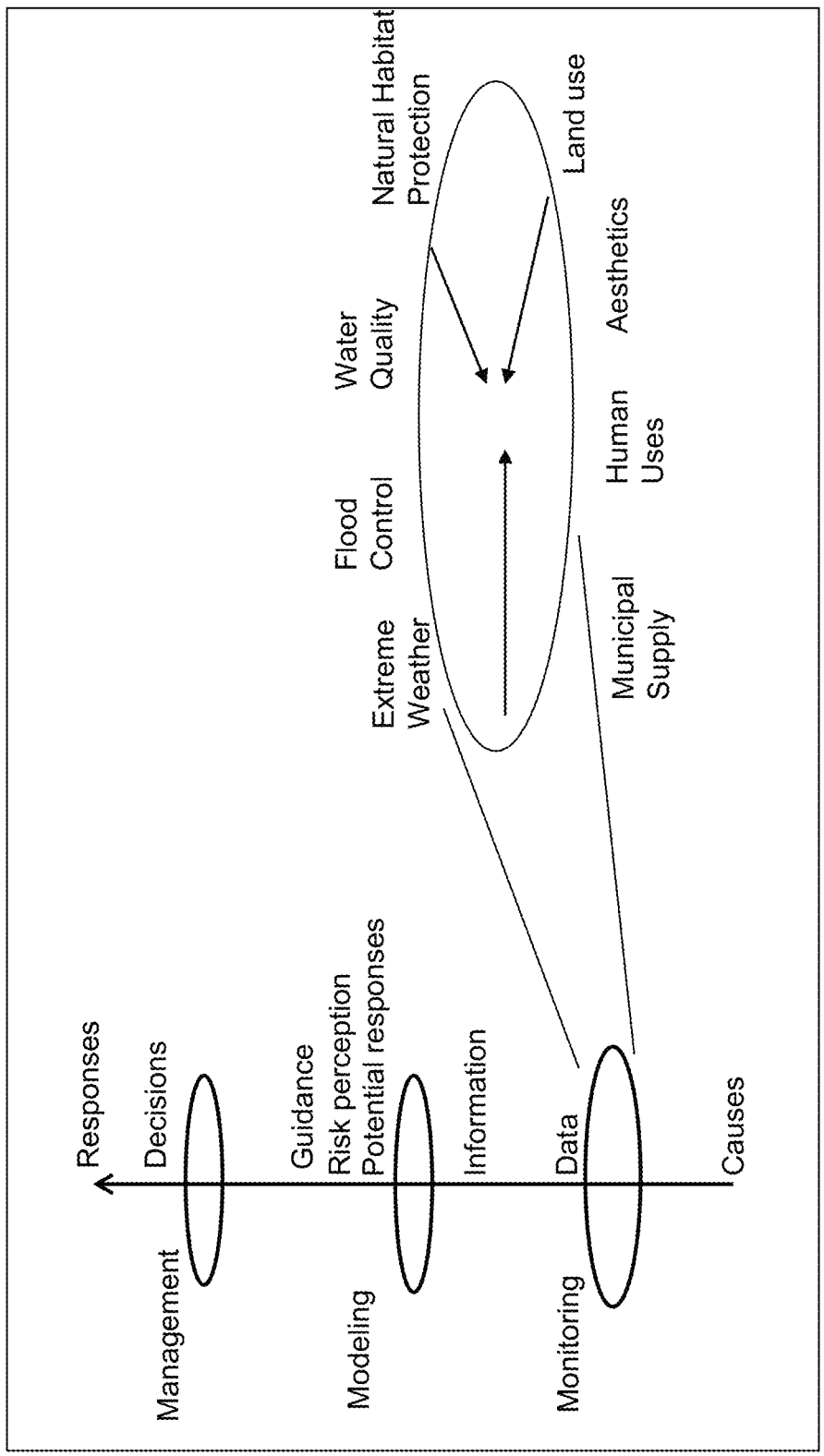
FIG. 13 illustrates dimensions of an automated, integrated monitoring, modeling and management (AIM3) methodology addressing water-resource management, according to an embodiment of the invention.

FIG. 13 illustrates an Integrated Monitoring, Modeling and Management (IM3) methodology according to an embodiment of the invention, as applied to water-resource management, which illustration follows in parallel fashion from the earlier description of an automated IM3 assessment approach for examining climate change impacts in FIG. 1. Referring now to FIG. 13, according to an embodiment of the invention, an automated IM3 assessment approach for examining water-resource management issues can include an integration depicted along a 'vertical' dimension that rises from monitoring (observing causes and gathering data), through modeling (including estimating risk and potential responses) in order to formulate guidance for decisions about responses, and can include along another dimension of integrated assessment (depicted as circles in a horizontal plane) combining research on many physical and socio-economic aspects of water-resource management that can be seen to interact on a geographical scale, including water quality, municipal supply, human uses, flood control, land use, natural habitat protection, extreme weather and aesthetics.

Example 15. Environmental: Research and Management in Social Energy Systems

Global Environmental Change and Energy Resource Use

The invention provides further for applying an ARS together with IM3 methodology for automated-IM3 (AIM3) learning in the domain of global governance of energy resources, including assessing potential integrated assessment of global warming impacts, assessing global warming as a symptom of natural energy-technology feedbacks (ETF), building a modeling framework, and building an AIM3 global energy resource learning model.

The invention further provides for incorporating an analysis component termed "utilergy" with a specific definition, wherein 'utility' is defined in terms of system service and is a scalable parameter for modeling and calculating "usefulness of energy". The invention further provides for defining one "util-erg" and a quantity, 'utilergy', as mathematical product of usefulness and energy.

Example 16. USG—Research Questions for an AIM3 Global Energy Resource Learning Model A user of an AIM3 learning model for studying global energy resource use can set a user-specified goal (USG) directive to address the following hypotheses and/or research questions:
(1) What are the changing patterns over time of energy flow through various societal subsystems, both in terms of (a) graphed node-arc subsystemic networks and (b) geographically mapped storage, dynamic transport, through-flow and use?
(2) Are there patterns of growth, stability or a combination of growth and stability that can be seen in an analysis of multiple energetic subsystems within human society?
(3) How do patterns of growth, stability or a combination thereof vary in causal networks and/or dynamic simulations when analyzing the system in terms of a varying objective function wherein each subsystem follows goal-directed rules to increase useful energy density within the subsystem to a greater or lesser degree?

Research Agenda (Relating to Research Objects in a Library of Possible Experiments)

To achieve answers to the above research questions, an AIM3 energy-resource learning model can choose Experiment Objects (EOs) that monitor energy 'through-flow' through various subsystems of the human social system and that analyze (and/or model) the impact of increases in energy density in various subsystems. These approaches can include at least the following EO categories, without limitation:
EO category 1—Tracking and mapping a set of parameters for each subsystem, including reserves, extraction, transport, storage, processing, consumption, conversion, price and growth, among others (see FIG. 14, described below);
EO category 2—Deriving, through modeling, measures of "energy intensity", "energy density", "useful energy" and/or "energy usefulness" (or "utilergy") in each subsystem and the extent of feedback relationship between technology and energy through-flow and/or useful energy in each subsystem (see FIG. 14);
EO category 3—Exploring multiple dynamic structures for an average subsystem using constraint-based optimization, wherein growth and stability are optimized within a set of constraints and/or objective functions for each subsystem;
EO category 4—Modeling the management component of various subsystems as a goal-directed function, where the goal is to maximize growth, stability, and/or a combination of growth and stability.

Figure 14:
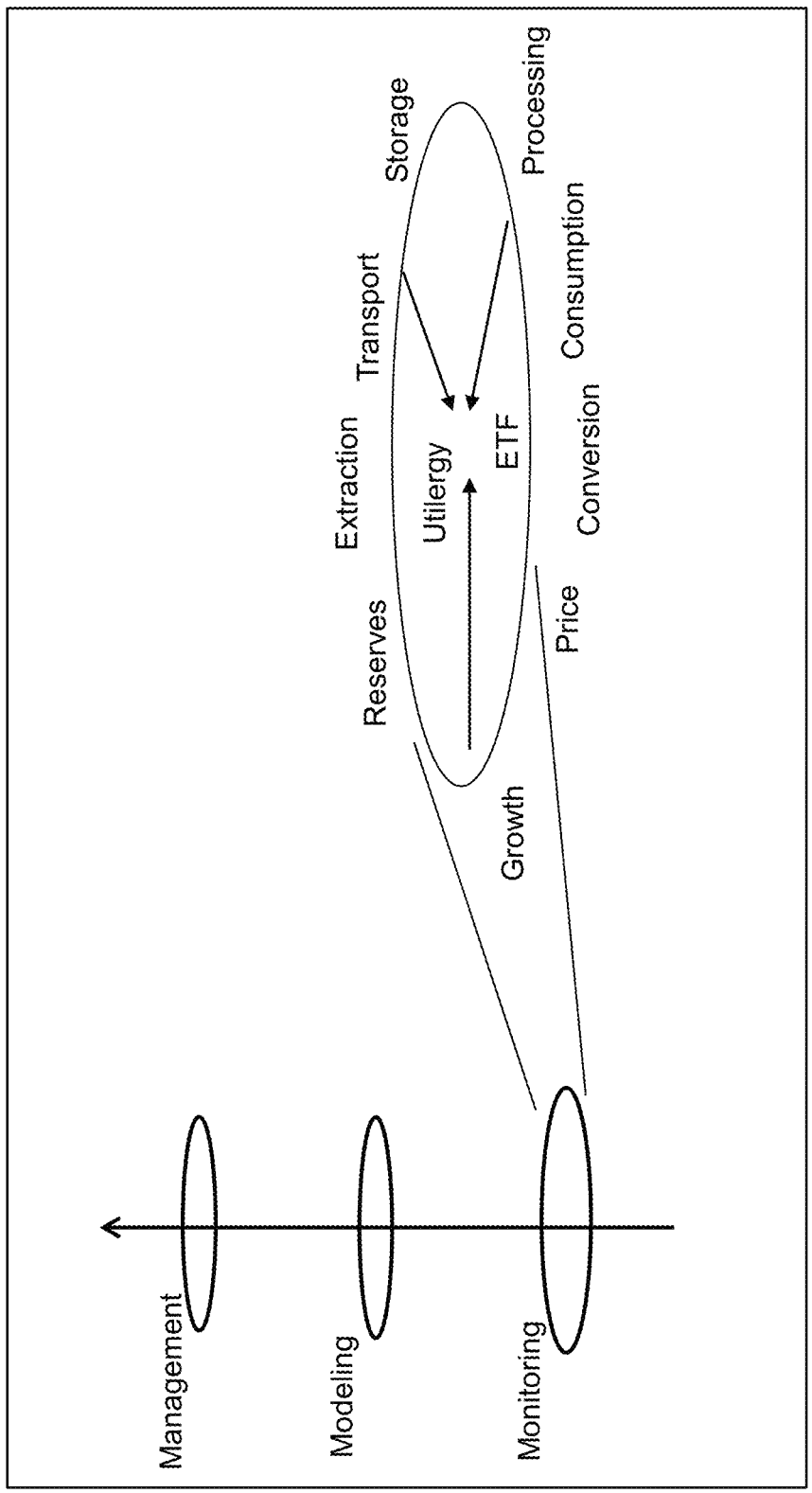
FIG. 14 illustrates dimensions of an automated integrated monitoring, modeling and management (AIM3) methodology addressing use of global energy resources, according to an embodiment of the invention.

FIG. 14. illustrates an automated Integrated Monitoring, Modeling and Management (AIM3) approach for studying human use of global energy resources, whereby utilergy and ETF are core variables among parameters such as reserves, extraction, transport, storage, processing, consumption, conversion, price and growth.

Figure 15:
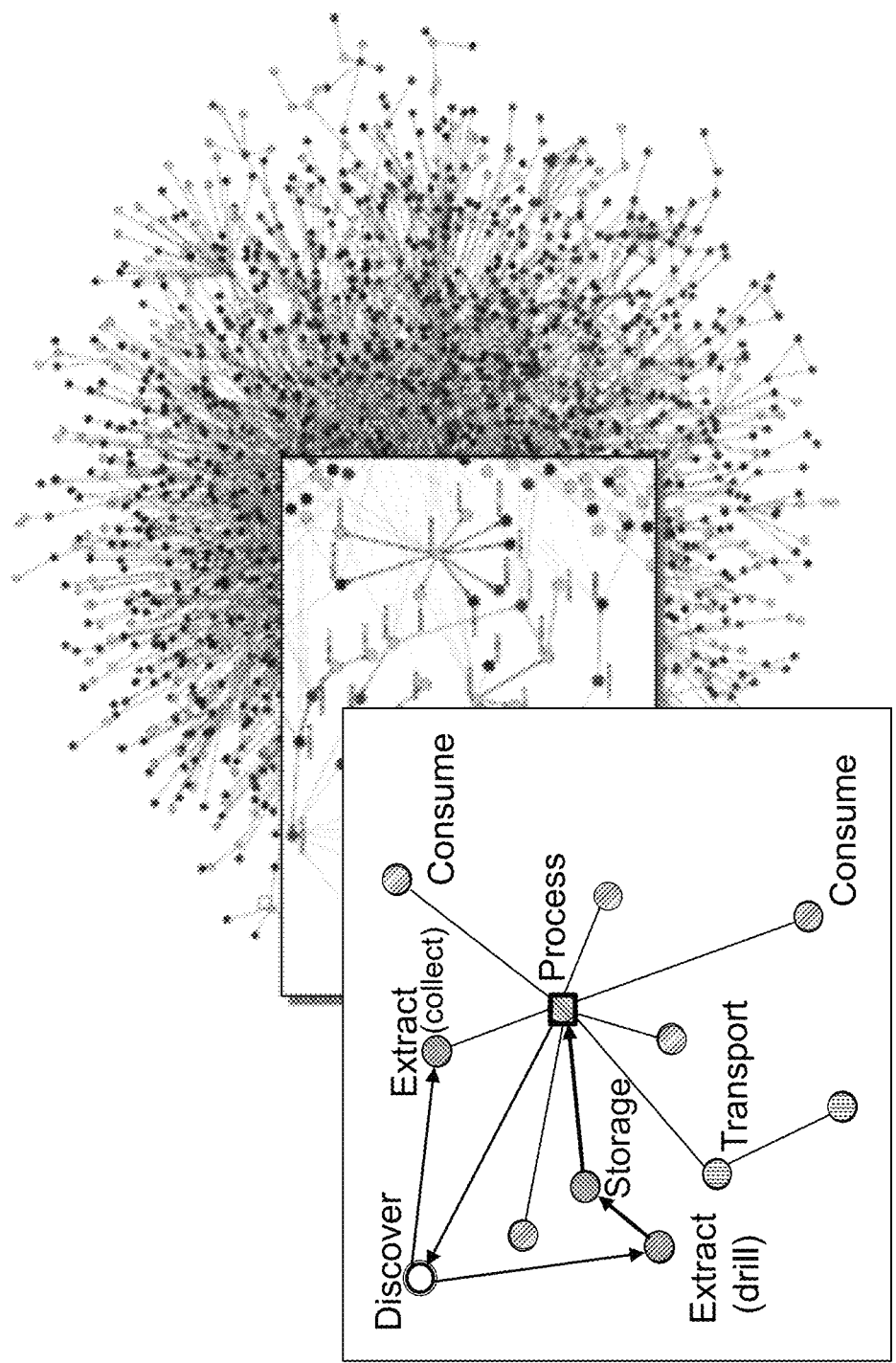
FIG. 15 illustrates construction of a knowledge-base-assembly causal network for energy resource systems in an automated research system according to an embodiment of the invention.

FIG. 15 illustrates a knowledge-base-assembly causal network for energy resource systems in an automated research system according to an embodiment of the invention, where "discover", "extract (collect)", "extract (drill)", "transport", "process", "storage", and "consume" are illustrative modeling parameters in the causal network, and where a sub-network can be seen to be nested into multiple subsystems formed at differing levels of organization.

'Utilergy' as a Modeling Variable for AIM3 Studies of the Human Energy Resource System The invention provides for improved definitions of "incorporated energy", "usefulness", "useful energy", "usefulness of energy" and "useful energy density." An embodiment provides for a novel modeling variable, "util-erg", which can be formed from a multiplication of dimensional units of energy and redefined dimensional units of 'utility', wherein 'utilergy' is characterized as having the dimension of "usefulness of energy" in an energetic system.

Example 17. Modeling Framework: Growth Modeling Module for an Energetic System An ARS can provide for integrating a model of growth in any system as an inherent property of the energy within that system, as follows:
An Energetic Structure is an organizational process, $O_{r_i}$, for which there exists an organizational radius, $r_i$. An energetic structure may be an energetic system.
An Energetic System is characterized by an organizational radius, $r_{(j=n)}$, and is an assemblage of energetic structures within an observed boundary, which structures are characterized by organizational radii $r_{(i<n)}$.
The Observed Boundary is the minimum spatial boundary that will circumscribe all the components of the energetic system, as defined by inter-relationships between the energetic subsystems comprising the system and by energy and material responsive to those subsystems, as determined by an observer.
Dynamic Coordination is a process whereby kinetic energies become stored through harmonization, or non-interference.
A Subsystem is a subset of energetic structures within an energetic system that share a common functional relationship to the system, which relationship differs from relationship of other subsets to the system.

One embodiment of the invention further provides a "utilergy" hypothesis that can be used in modeling experiments, the hypothesis being that a positive feedback occurs in an energetic system as increasing energy consumption amplifies techniques for extracting useful energy from the environment (i.e., amplifies the energy-technology feedback, or ETF). For instance, an amount of energy (or a form of energy, or a particular flow-path through the subsystem) that cannot increase the ETF can be defined for the purposes of this embodiment as having little or no usefulness, thus essentially zero utilergy. A form of energy that can increase the ETF can be said to have a higher usefulness, and consequently may have 'x' units of utilergy if the ETF is enhanced by some 'y' percentage.

AIM3 Utilergy-Related Research

Figure 16:
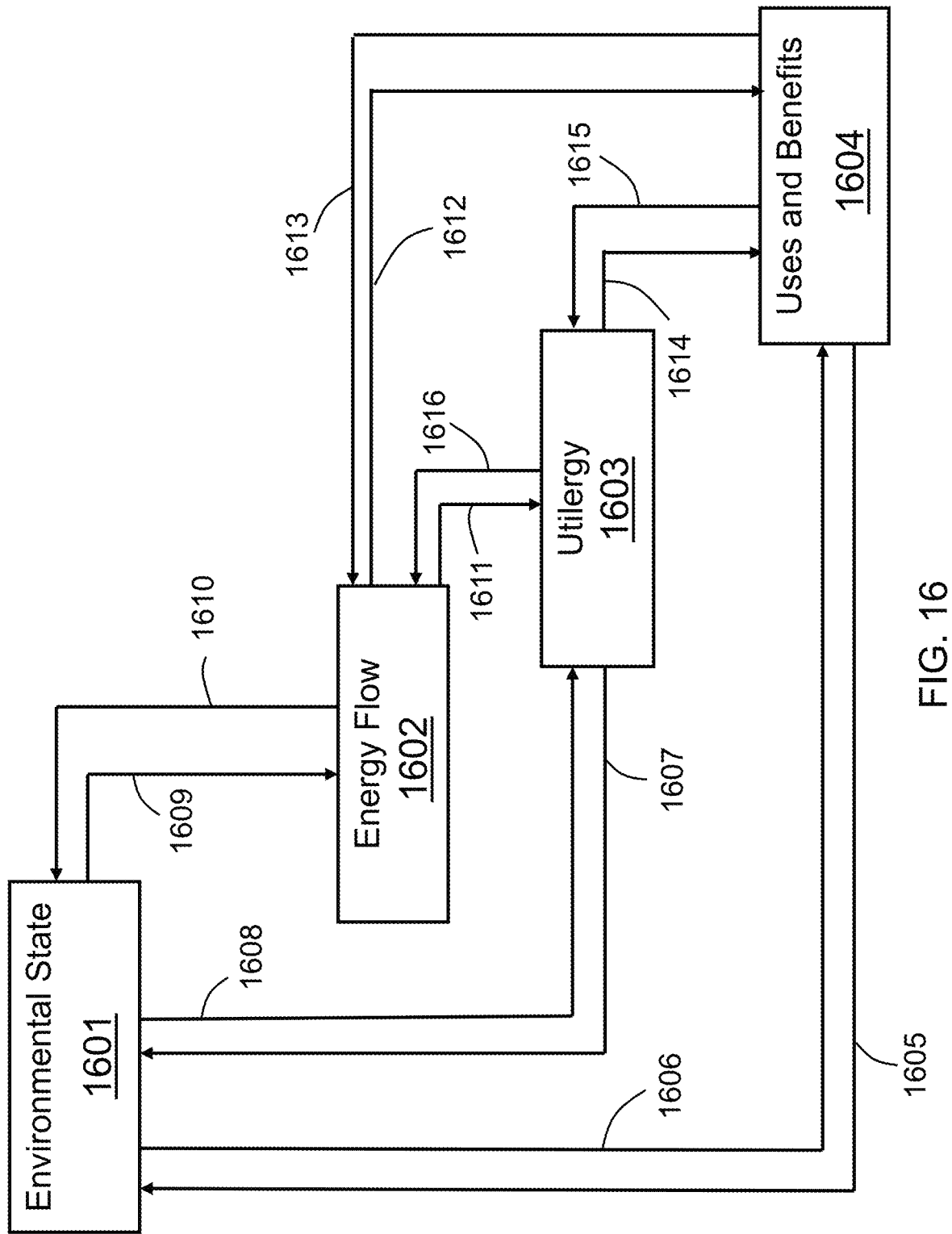
FIG. 16 illustrates aspects of an automated research methodology applied to modeling and analysis of global energy resources according to an embodiment of the invention.

FIG. 16 illustrates a reduced-form modeling framework for describing relations between environmental state 1601, energy-flow 1602, utilergy 1603 and uses/benefits 1604, according to an embodiment of the invention. Many relations will have a dependence on geographically referenced energy-region attributes, such as topography, stratigraphy, land use or soil type, so that integrated modeling designed to interface with GIS tools will be advantageous. The modeling framework can be transferred and utilized by researchers in neighboring energy resource regions, either directly or by adjustment from look-up tables based on a menu of regional characteristics commonly available. To build the relationships the research can be guided by field investigations and/or by previous studies of energy regions. FIG. 16 illustrates developing a combined factor of utility and energy (i.e., utilergy 1603) in a reduced form modeling exercise based on environmental state 1601, energy flow 1602, and uses and benefits 1604.

Building an integrated model in a GIS-based framework that is able to calculate and simulate the relationships shown in FIG. 16 can be implemented by wrapping submodels (or component software objects) with an interface and coordinating the modeling routine with a controller object). FORTRAN, C, and Visual Basic modeling objects, for example, can be controlled by C++ and/or Java routines. An embodiment provides for the relationships to be described and assembled in a comprehensive matrix, or set of relational databases, as illustrated in the following modeling and/or analysis steps:

Modeling/Analysis Step 1605: Relations of Human Uses 1604 to Environmental State 1601.

Various uses that directly affect subsystem (urban, transport, infrastructure) condition, energy storage levels, infrastructure and surfaces (transport) can be described in these relationships. For instance, building a settlement or a city may cause an energy-resource region to become reduced in some measure of quality. Or pumping oil may reduce a reserve by some measure of usefulness. Environmental impacts of economic decisions can be included. These relations are likely to vary geographically and can be specified as a function dependent on a GIS theme.

Modeling/Analysis Step 1606: Relation of Environmental State 1601 to Human Uses and Benefit 1604

Ecosystem diversity and wildlife abundance of some measurable degree leads to an environmental use at some measurable rate, which may vary from zero to some maximum rate. Energy-resource condition in a region, specified by utilergy 1603 (as related to energy "quality") or energy abundance metrics for cities, energy and transport can lead to environmental use at some rate. Energy resource/reserve condition allows a certain degree of human use. Benefits 1604 of these uses may be specified by market and/or non-market valuations. Some of these relations may be specified independent of geographical location Modeling/Analysis Step 1607: Relation of Utilergy 1603 (Usefulness of Energy) to Environmental State 1601

Human habitat degradation or enhancement can be made a function of utilergy 1603 at the entry point of energy flow into the subsystem and/or region of interest. These relations are specified per utilergy constituent (e.g., subsystem growth, economic value, accessibility, etc.) and may be geographically specific. Relation of utility (as relating to available energy quality) to local energy reserve condition (resource utilergy) may be described as a function of mining or pumping (exploitation) operations (geographically specified). Relationships of utilergy 1603 to ecosystem species, health and abundance, and human environment, may be based on observations and/or literature descriptions; e.g., energy flows causing high carbon emissions that lead to global warming and potential negative ETF consequences in some subsystems can be docked with negative utilergy points. Feedbacks may need to be described here as environmental impacts degrade social conditions, which in turn alters the ETF (and hence utilergy 1603) further. Some of these relations may be specified independent of geographical location, but others may depend on mappings of cities and other energetic subsystems.

Modeling/Analysis Step 1608: Relation of Environmental State 1601 to Utilergy 1603 (Usefulness of Energy)

Utilergy 1603 may be modified by retention or movement of energy through a subsystem or multiple subsystems by measurable degree, per constituent of energy flow 1602 and per residence time. Presence of human infrastructure may degrade (lower) utilergy 1603 by some degree per population density if it impedes the ETF, whereas presence of other subsystem processes may increase the usefulness of energy if they enhance the ETF. Climate state, for instance, can be directly related to fossil fuel use, with fossil fuel use having a demonstrably positive effect on ETF in most subsystems. At a global level, many of these relations do not need geographic specificity to be usefully studied in a learning model.

Modeling/Analysis Step 1609: Relation of Environmental State 1601 to Energy Flow 1602

The condition of the resource region affects energy flow 1602. Stratigraphy and resource/reserve levels affect flow. Climate state affects flow through feedbacks that affect solar, wind and tidal energy production, as well as through weather events that affect transportation. These relations are likely to be geographically sensitive.

Further field observations are useful for calibrating parameters in the models that encompass numerous interactions in the natural system that are difficult to observe directly, either because we are ignorant of their mechanism or because they are too expensive to measure in detail. For instance, a single parameter for energy production in one aspect of supply may be derived, even though it is likely that field investigation in elaborate detail could discover differing rates of production depending on subtle characteristics within a single energy-production region.

To help explore and describe this relation, an AIM3 system can include a GIS-based energy production/supply model (i.e., production, transport, storage and losses), which can be linked to additional modules from various "off-the-shelf" models. Examples of various such models can be found, such as models that develop linkages between ecological modeling and economic modeling in terms of equilibrium models, scaling and externalities.

Modeling/Analysis Step 1610: Relation of Energy Flow 1602 to Environmental State 1601

Environmental state 1601 includes the condition of physical and biological resources and standing cycles or patterns in those resources, including aspects of ecological stability and/or resiliency owing to diversity and multiple interrelationships between species. Reduced energy flow 1602 through a subsystem can impact the natural and human environment in some describable measure. One of the chief concerns about future climate change, for instance, is how resilient is the environmental state 1601 to fluctuations in flow 1602 that could accompany fluctuations in raw energy supply and/or supply disturbance. Research in this area conducted through an AIM3 research system according to an embodiment of the invention can include measuring, cataloging and describing these relationships.

Modeling/Analysis Step 1611: Relation of Energy Flow 1602 to Utilergy 1603 (Usefulness of Energy)

This is a key relation to be derived from field observations in local energy supply and use regions (or relevant subsystems), where possible, and from literature values where flow impact coupled to resource use contribution can be extrapolated from other studies. These relations may also be model-derived, e.g., for those constituents of utilergy 1603 that are related to rate-changes in subsystem characteristics only detectable through modeling. These relations are likely to be highly geographically specific (e.g., doubling energy flow 1602 through a specific urban subsystem can yield a different impact than doubling flow through a non-human subsystem. Examples include low-flow stagnation leading to loss of vitality in a region, or excessive overbuilding and activity that can become counterproductive in terms of human health and social benefit.

Modeling/Analysis Step 1612: Relation of Energy Flow 1602 to Human Uses and Benefits 1604

Energy flow 1602 allows multiple uses to occur at some rate dependent upon amount or delivery rate, e.g., electrical production, industrial manufacturing, mineral conversion and refining, up to some maximum per use type. Some of these relations are geographically dependent, some independent. These are direct relations, whereas indirect relations through energy quality follow the functional path 1611 and 1614. Benefits are based on market and non-market valuations. A preliminary survey of energy use and users can serve as a starting point for developing a comprehensive survey of energy resource users. Following this step, an energy allocation model can serve as a submodule to integrate these relationships with other aspects of the integrated assessment model.

Observed physical impacts on energy usefulness (utilergy 1603, and/or energy quality), on energy resource regions, cities and society will be translated into economic impacts in an analysis that can build upon new observation and historical data. Costs and benefits relating to energy resource use can be evaluated for relevant economic sectors and indexed to geographical location in the subsystem region of interest. Economic impacts can be weighed against costs of differing strategies to protect energy flow 1602 and reduce negative impacts at key sites, with conclusions drawn about which institutional strategies would best protect natural and human communities and the value of human uses. The research must aggregate results at various scales, from very local to regional, utilizing GIS tools to contrast the environmental and economic effects of centralized versus distributed institutional strategies.

Modeling/Analysis Step 1613: Relation of Human Uses 1604 to Energy Flow 1602

Energy uses (withdrawals) impact energy flow 1602 directly through demand functions. Energy extraction, storage and transport regulations affect flow rates. Changing political control and exploitation patterns in a resource region can affect flow. Human energy use may also indirectly affect energy flow 1602 patterns through the complex mechanism of $CO_2$ increase, global warming and consequent environmental changes (or events) that then impact energy flow rates (e.g., increased storm force and frequency affecting oil platforms in the Gulf of Mexico). Some of these relations are location-dependent and some too diffuse for specific regional modeling. Researchers can utilize an AIM3 system to explore to what degree information from specific, local studies can be extrapolated to anticipate broader impacts.

Modeling/Analysis Step 1614: Relation of utilergy 1603 to human uses and benefits 1604

This set of relationships, which are important to many of the potential Experiment Objects (EOs) applicable to research in the domain of human energy use, comprise a matrix, with utilergy parameters 1603 as one dimension and a series of potential uses and benefits 1604 as another dimension. Lowering utilergy 1603 will limit the use of that energy flow 1602 by some measure, to be determined by observation or by extrapolation from other studies (e.g., switching from high-grade oil to biomass in some locations could increase cost of transportation and hence reduce use of transportation. Form of energy relates to its use. Again, benefit functions can be built on market and non-market valuations.

Modeling/Analysis Step 1615: Relation of Human Uses 1604 to Utilergy 1603

Processing, conversion and transport functions can impact energy usefulness within a subsystem. Human-induced atmospheric cloudiness, for instance, can reduce available solar energy in a region. Increasing water use upstream can reduce hydroelectric production downstream. Distilling, concentrating and refining, on the other hand, can increase energy quality, making energy more useful for more and/or different applications. Increasing flexibility of use can allow innovation and movement. Liquid fuels, for instance, are more portable and more easily injected into engines, and can have higher BTU/gram ratios and higher combustion rates, thus enabling airplane and jet transportation.

Modeling/Analysis Step 1616: Relation of Utilergy 1603 to Energy Flow 1602

Liquid fuels can be transported more easily through pipelines. Electricity can be transported even more easily along wires suspended above the ground. The increase in energy usefulness represented by conversion of oil to electrical energy can be modeled by seeing its relation to increasing the ETF (e.g., by counting the reduced costs of implementing the transport of so many ergs from one location to another, or by counting the added benefits of having the more flexible, electrical energy source to build and maintain new energy-acquiring technologies, such as computers being useful for controlling nuclear reactions or enabling deep-sea drilling operations).

Developing an AIM3 Learning Model and the Process of Knowledge Base Assembly

Figure 17:
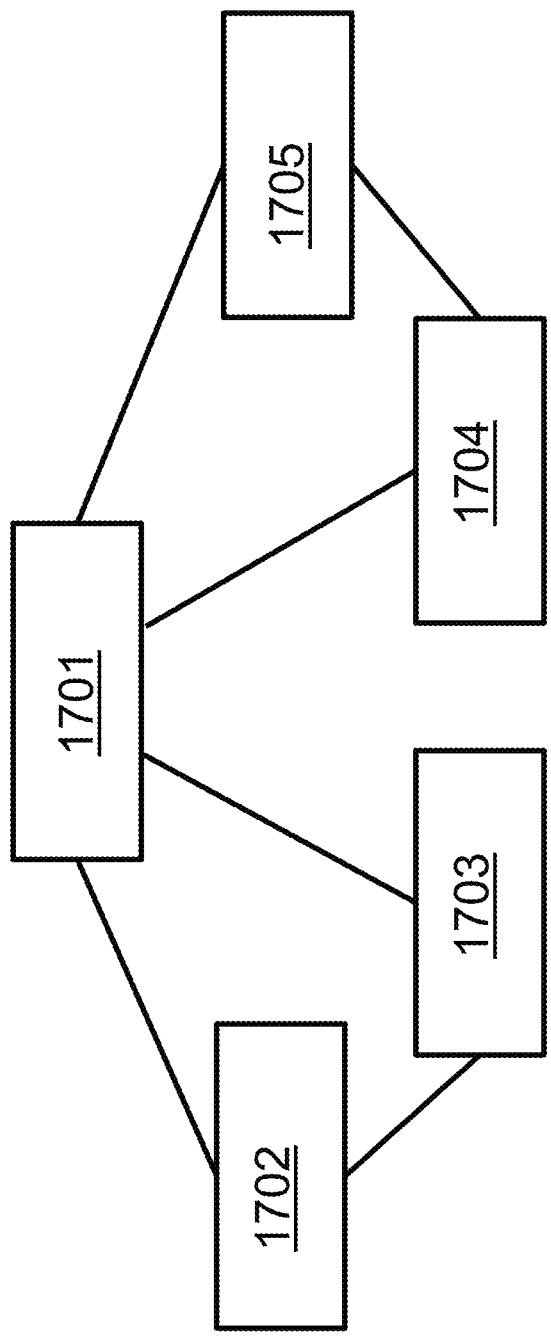
FIG. 17 illustrates functional partitions of the method of building a domain Knowledge-Base-Assembly according to an embodiment.

Building an automated learning interaction between data-gathering and the modeling process can be characterized as growing a knowledge-base assembly. This can be an iterative, growing process, where information fed into the process can be more or less useful depending on the ability of the results (or know-how) developed from that information (a) to generate new, useful hypotheses and (b) to accelerate data-gathering. FIG. 17 illustrates research modeling components for an AIM3 energy resources learning model according to an embodiment of the invention. The knowledge-base-assembly engine 1701 can include data about the energy resource network stored in a library database or knowledge base (KB) 1705. Associations among data parameters can be data-mined by association mining engine 1702 and reverse-engineering modeling components 1703 (Bayesian classifiers and inverse modeling components) can interoperate with a simulation engine 1704 that is capable of forward simulation of system dynamics based on network parameters in the library.

FIG. 17 further illustrates functional partitions of building a domain Knowledge-Base-Assembly 1701 for human energy resources and energy use platform, wherein an association mining engine 1702 connects to reverse-engineering components 1703 and functions to create a causal network model that can be based on AIM3 research experiments, while an Energy Resource Causal Network Knowledge-Base (or Library) 1705 can be used to generate a causal network map that can be iteratively tested for congruence with the experiment derived network mapping, and the converged model can be tested using the Simulation Engine 1704. Greater details are directly analogous to those shown in FIGS. 8A-8E above.

A knowledge-base-assembly cascade can be described that brings together (a) a reverse-engineered, energy-resource network model and (b) a literature-based, energy resource system model/map (see FIG. 18, described below). The reverse-engineered model is derived solely from data, and is essentially a set of hypothetical models of varying likelihoods to explain the data. This data-derived model set is likely to contain "unknown unknowns", i.e., novel causative structures not previously discerned.

Figure 18:
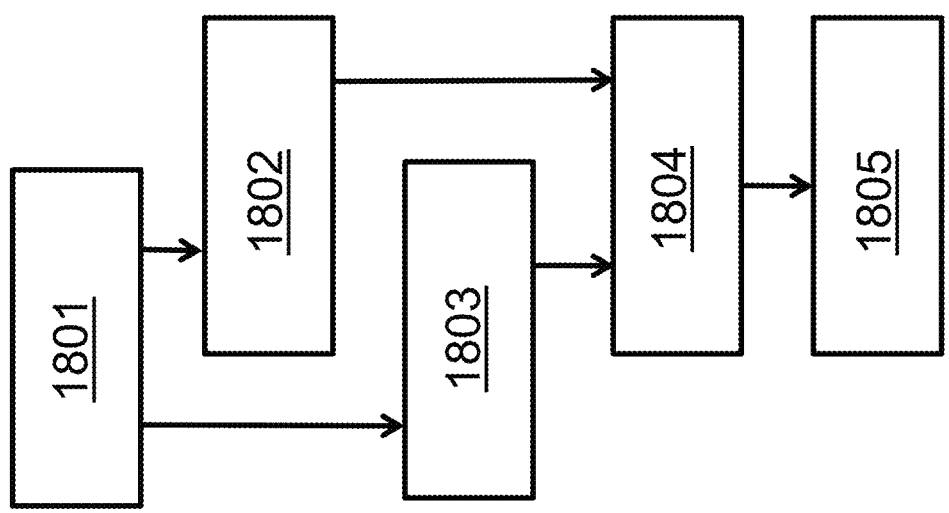
FIG. 18 illustrates knowledge-base-assembly functions in an automated research system according to an embodiment of the invention.

Referring to FIG. 18, in the context of research on human energy resources, a statistical analysis and association-mining step 1801 identifies predictor sets for network modeling, which predictor sets can be used at step 1802 to construct energy resource networks from time course information, identifying valuable (or strong) nodes in the network, and detecting statistically exceptional inputs and outputs at some nodes. At step 1803 a literature-based Energy System map can be developed from the domain knowledge base, which can include interactive visualization. At step 1804 a knowledge base assembly module compares the reverse-engineered and literature-based networks, testing for congruence, and the process can be iterated to create an integrated model. At a step 1805, the system simulates perturbation effects useful for designing the next round of data gathering; VOI metrics can be developed based on the simulation showing potential positive or negative gains in correspondence to known dynamics (based on random or progressive variation of variables, which variables, if found influential upon outcome and not currently mapped into the network causal dynamics with high certainty, can be made the subject of a next experimental goal (i.e., information gap to be closed) and therefore exploratory experiments in a next round of experimentation.

For an AIM3 energy resources research system, an initial domain knowledge base can be developed from a literature-based mapping and can be related to a set of models based on the existing collective wisdom of prior research on energy metabolism in human society and dynamic modeling of energy flow in the economy, topics which have been addressed in numerous studies (see for example: Worrell E, 1994. "Potentials for Improved Use of Industrial Energy and Materials." Ph.D. Thesis: University of Utrecht; Wilting H C, 1996. "An energy perspective on economic activities." Ph.D. Thesis: University of Groningen; Fischer-Kowalski M, 1998. Society's metabolism—the intellectual history of materials flow analysis, part I, 1860-1970. Journal of Industrial Ecology, 2, (1), 61-78. Fischer-Kowalski M, and Hüttler W, 1998. Society's metabolism—the intellectual history of materials flow analysis, part II, 1970-1998. Journal of Industrial Ecology, 2, (4), 107-136; Battjes J. J., 1999. "Dynamic Modelling of Energy Stocks and Flows in the Economy: An Energy Accounting Approach." Ph.D. Thesis: Center for Energy and Environmental Studies (IVEM), University of Groningen; Haberl H., 2001a. The energetic metabolism of societies, part I: Accounting concepts. Journal of Industrial Ecology, 5 (1), 11-33; Worrell E, Ramesohl S, and Boyd G, 2004. Advances In Energy Forecasting Models Based On Engineering Economics. Annual Review of Environment and Resources 29 (1) 345-381; Schenk, N.J., 2006. "Modelling energy systems: a methodological exploration of integrated resource management." Ph.D. Thesis. University of Groningen, Groningen; de Vries H. J. M., van Vuuren D. P., den Elzen M. G. J., and Janssen M. A., 2001. 'TheTimer IMage Energy Regional (TIMER) model'. Technical Documentation, No. 461502024/2001, RIVM, Bilthoven; van Asseldonk M, 2004. "Modelling Power Exchange Between Norway And The Netherlands Through The Norned Cable." M.Sc. Thesis: University of Twente/Norwegian University of Science and Technology; Jensen, J. and B. Sorenson, 1984. Fundamentals of Energy Storage. Wiley-Interscience, New York. Messner S. and Schrattenholzer L., 2000. MESSAGE-MACRO: linking an energy supply model with a macroeconomic module and solving it iteratively. Energy, 25 (3), 267-282; McFarland J. R., Reilly J. M., and Herzog H. J., 2004. Representing energy technologies intop-down economic models using bottom-up information. Energy Economics 26 (4) 685-707; all of the foregoing the teachings of which are hereby incorporated herein by reference in their entirety.

The collective wisdom may explicitly describe unknown areas and connections, as well as characterizing uncertainties in these and other areas; but, the literature-based models, and thus the knowledge-bases that are assembled from them can be blind to the unknown unknowns in the system.

The knowledge-assembly module involves iterative fitting of the two input model sets, using congruence-testing and parameter variation. Many possible causative relationships inferred in the reverse-engineering will fall away when merged with very certain known models, but in more uncertain areas the reverse engineering will fill in gaps and enlarge the current view. A resultant best-fit model is then passed into a simulation module where perturbations to the system can be simulated to test effects on internal subsystem dynamics and dynamics between subsystems nested within an overarching system. The perturbation-testing creates new hypotheses that direct another round of data-gathering. Referring to FIG. 18, a knowledge-base assembly cascade brings a reverse-engineered energy-resource network model and a literature-based energy resource system model/map into the knowledge-base assembly model.

More details of the AIM3 Learning and Knowledge-Base-Assembly layer are shown in FIGS. 8A-8E (described in more detail above). Statistical analysis, association mining steps, and network reverse engineering steps are shown on the left (collectively 800) in FIG. 8A, while the literature-based model assembly is described on the right (collectively 801). The existing literature can be text-mined and parsed and auto-assembled into XML database structures. Ontologies allow sorting and sifting of the input text based on objects (nouns), interactions (verbs) and context, as well as resolution of ambiguous terms. The acquired information is assembled into a set of energy flow-paths for multiple subsystems, where these pathways are structured into networks having nodes (objects/nouns) and arcs (interactions/verbs). Systems and subsystems are formed at differing levels of organization, with the sets of nodes and arcs being mapped in the particular context of a particular level system. For example, a movement of oil may be mapped as shipping transport from one port in one country to another port in another country. At another level of organization, a movement of oil may be mapped as a piped transport from a corporation's underground tank to an electrical generator. a reverse-engineered energy-resource network model and a literature-based energy resource system model/map into the knowledge-assembly model.

Parameters for each subsystem can include energy reserves, extraction modes, extraction rates, transport modes and rates, storage mode and volumes, processing steps and rates, uses, consumption rates, conversion efficiencies, switching/conversion pathways, price and growth (in each of many of the parameters), as well as other parameters. In both modeling approaches, deriving and mapping measures of "energy intensity", "energy density", "useful energy" and/or "usefulness of energy (utilergy)" for each subsystem and geographically is an important and useful step. Deriving through the modeling the extent of feedback relationship between technology and energy through-flow and/or energy usefulness in each subsystem is another important step.

In the simulation module, dynamics and flux analysis can be tested to explore robustness and noise sensitivity in the network model. Policy adjustment scenarios can be tested for effect on multiple parameters and particularly the model-derived parameters, such as the ETF, utility and utilergy. Previous work on scenario formulation and models (Gritsevskyi A, 1998. "The Scenario Generator: a tool for scenario formulation and model linkages." International Institute for Applied System Analysis (IIASA), Laxenburg; hereby incorporated herein by reference in its entirety) and energy policy models (Frei C. W., Haldi P. A., and Sarlos G., 2003. Dynamic formulation of a top-down and bottom-up merging energy policy model. Energy Policy, 31, 1017-1031; hereby incorporated herein by reference in its entirety) can be compared with the updated data from monitoring and subsequent simulations.

Query Manager Connecting Knowledge Base-Assembly and Automated Experimental Design To automate the growth of an AIM3 knowledge-base assembly in one embodiment, linkage is made to a Query Manager module that manages queries (which can be programmed to include rule-based routines) and optimizes the research progression by mapping particular classes of queries to experimental programs needed to gather data for the continued modeling and iterative fitting of the integrated energy use and resource model. In the AIM3 methodology, this interface can be connected with visualization for supervised learning in the hands of the modelers, and/or the interface can allow managers to access and modify the query process directly.

A knowledge-base assembly engine according to one embodiment can interface with a Congruence Module and pass further data needs (information gaps) to the Query Manager and a Research Optimization Interface object in the Experiment Director to generate further experimental design and data-gathering, and can further include an information management system (IMS) with a database component and automated data-processing that can feed back into the knowledge-base assembly functions.

A research optimization component built into the ExpDir module of an ARS can explicitly treat the question of value of information and usefulness of a potential data-gathering step to the desired modeling goal and/or the likelihood of gaining a robust answer to a query. As will be discussed below, defining a "util-bit" can be applied in the context of an information-knowledge feedback (IKF) process, where information-flow into the knowledge assembly module can enhance and accelerate the gathering of more useful information, and where usefulness of information can be defined as a function of the acceleration of the knowledge assembly. As the AIM3 system learns more about growth of energetic systems generally, the tight relationship of energy and information can guide the AIM3 system toward goal-directed rules that optimize information acquisition and knowledge assembly in a growing AIM3 Energy Use and Resource Model (which can directly provide regular and iterative growth to an Energy Use and Energy Resource domain Knowledge Base).

Parallel Between an AIM3 Learning/Research Model and Growth in Energetic Systems A preferred embodiment provides for a parallel function to exist between the energy-acquisition process of an energetic system and the information-acquisition process of an AIM3 method utilized in automated research. In modeling a living system, an energy-gathering step can be made adjustable in response to a demand function and a dynamic organization function (which may respond to the demand function) can recognize its systems energy needs and adjustably instruct the energy-gathering step. Here the demand function is parallel to a management function in the AIM3 structure according to an embodiment, while the dynamic organization function is parallel to the modeling (including the congruence testing and simulation) functions. As shown in Table 2, below, the three-component model can be generalized, a step C is adjustable in response to a function A, while a function B, in response to the function A, can recognize its resource needs and adjustably instruct the step C. The generalization can align information acquisition in an AIM3 model and energy acquisition in energy-resource network modeling. Management and Demand are related to end-user of the resource. Modeling and Dynamic organization are related to structuring of the resource into something that makes the raw resource more useful. Monitoring is related to acquiring information about the system, which is parallel to an energetic system acquiring energy.

TABLE 2

Three component model generalized showing parallels between an automated learning/research model (AIM3) and growth in an energetic system., aligning information acquisition (Monitoring) in AIM3 model and energy acquisition in energy-resource causal network.

| General | A | B | C |
| --- | --- | --- | --- |
| AIM3 method/ system | Management | Modeling (structuring, usefulness) | Monitoring (acquire information) |
| Energy Resource Network | Demand | Dynamic organization | Acquire energy |

One embodiment of the invention provides for optimization and/or efficiency functions discerned and learned in the progress of AIM3-based research on energetic systems (either from new experiments and/or from an Energy Use and Resource Knowledge Assembly (EUR-KA) to directly instruct optimization and efficiency functions in the AIM3 research and learning method and system itself, with a preferred embodiment allowing a version of the AIM3 system to automatically generate new module structures and adopt such growth functions as the AIM3 system learns from the EUR-KA.

Goal-creation objects, for example, can be programmed to include various learning goals, such as, e.g., a goal to reduce uncertainty in known parameters; explore unknown unknowns (ascribe new parameters, for example, as in creating and fitting an unknown data structure); solve specific pathway in causal networks; complete causal network mappings, etc. It will be appreciated that numerous examples are available to one skilled in the relevant art to generate and program goal-creation objects.

The invention provides for goal-seeking routines to be built into one or more of the Query Manager, the Experiment Chooser and the Congruence Module, without limitation, where numerous parameter dimensions can be combined as n-dimensional 'surfaces' or vectors and the routine provides an optimization objective function to maximize this function in local data space (i.e., to 'climb' the optimization surface). Methods to implement such optimized goal-seeking through rules-engines are well-known to one having ordinary skill in the art relating to optimization.

It is instructive to consider analogous goal-setting components that are used in a simple positional component 'virtual' or 'model' system, such as, for example, a chess program—where one primary objective function for a normal chess 'experiment' (or game) is to capture the opposing king, but the overall task involves numerous positional and tactical sub-goals.

Example 18. Business Method—Illustrating Agreement Between a COMPANY Implementing the Invention According to this Example and a PHARMA CUSTOMER for Implementation and Use of an Automated Biological Research System (ABRS) (and/or Automated Cure-Finding Method and System (ACFMAS))

According to a preferred embodiment, a COMPANY that has implemented an Automated Research Service as a business method can engage in one or more of the following steps:

a) Providing access to the ARS service for a fee to a customer, such as, for example, a pharmaceutical customer ('PHARM-A');

b) Enabling and allowing PHARM-A to operate the user interface and Query Manager of the ARS to create a User-Specified Goal (USG), including accessing the Experiment Director module (ExpDir) to choose an Experiment Object from among a set of EOs in a Library of Possible Experiments (LOPE), which LOPE can be distributed over the Internet among many companies and/or distributed LOPE databases. Preferably, the EOs share a common interoperability software object format, more preferably the EOs and the ExpDir and the automated laboratory software objects (many of which are described above) are based on object-oriented programming (OOP) design and further share the ANSI/ISA-S88 (Parts 1-3) International Batch Control standard (S88);

c) Enabling and allowing PHARM-A to execute the chosen Experiment Object automatically by so instructing the ARS;

d) Optionally brokering an automated Agreement based on a Template Contract provided by the ARS to PHARM-A, which proposed contract can be of a format pre-approved by the automated laboratory CRO, or by COMPANY in the event that COMPANY is also the direct provider of the automated laboratory services;

e) Executing the contract with the parties, and PHARM-A directing the EO to be run;

f) Running the experiment and looping the ARS process as many iterations as required to close the gap on the USG and then the ARS automatically delivering results to PHARM-A.

At step (e) above the COMPANY and PHARM-A preferably execute the contract automatically, with the final brokered contract form and terms resulting from a rule-engine optimization based on business object parameters set in the ARS by COMPANY (using business method software object components of the ARS for information entry) and by the user PHARM-A (entering necessary information through the UI interaction with the Query Engine and set into the User Specified Goal transaction).

A contractual agreement auto-generated from template forms within the automated research system, according to one embodiment, can be illustrated by the following example and paragraphs:

"Research Service Agreement Company and PHARM-A

"PHARM-A Inc with an address at [STREET], [CITY], [STATE] [ZIP] and its Affiliates (hereinafer "PHARMA") and COMPANY, with an address at [STREET], [CITY], [STATE] [ZIP] (hereinafter "COMPANY") enter into this Research Service Agreement (the "Agreement").

"Whereas, PHARMA has generated preclinical and clinical experimental data in the area of inflammation, oncology, diabetes, MS and cystic fibrosis, regarding the pharmacological activities of PHARMA compounds; and "Whereas, PHARMA has approached COMPANY and COMPANY has certain skills and platform technologies to generate and experimentally develop learning pertaining to PHARMA's Experiment Query Information and Experiment Data and PHARMA Confidential Information (PCI) (as defined below); and "Whereas, COMPANY will use, among other tools and databases, COMPANY's Automated Biomedical Research Technology (as defined below) to execute PHARMA's chosen Experiment Object and subsequently evaluate PHARMA's Chosen Experiment Data together with PHARMA's Confidential Information to perform Services (as defined below).

"Now, therefore the parties agree on the following:

"1. Definitions 1.1 "Affiliates" means with respect to a party, any corporation, firm, partnership or other entity, which directly or indirectly controls, is controlled by, or is under common control with such party.

1.2 "Domain Specific Goal Solution" is a subset of the Domain Knowledge Base (as defined below) and shall mean COMPANY and Service-Specific Knowledge Base Assemblies that are comprised of causal network statements in specific therapeutic or disease areas, together with rule bases, the analysis and experimental design components, and other automated reasoning technologies specifically generated by the ABRS for PHARMA's use and designed to act on PHARMA Experiment Query Information.

1.3 "Modeling Module" shall mean the portion of the ABRS technology platform, including software tools, rule bases, statistical computation, and know-how, that performs logical reasoning over a domain represented in a causal network and knowledge base to generate reasoned proposals predicting possible causal correlations among multiple nodes and interrelationships.

1.4 "Domain Knowledge Base" shall mean the structured information in the ABRS databases and in distributed accessible databases.

1.5 "ABRS Technology" means collectively the Domain Knowledge Base (DKB), which includes Domain-Specific Goal Solutions, Experiment Director Module, Data Analysis Engine, Congruence Module, Knowledge Base Assembly and Modeling Module objects.

1.6 "ABRS Biomedical Model" means those causal statements created solely by the ABRS in the course of conducting Services which may incorporate information from publicly available sources and does not include any PHARMA Confidential Information and PHARMA Experiment Query Information.

1.7 "PHARMA Confidential Information" means all information on therapeutic or disease areas, relevant literature not in the public domain and all information about compounds as PHARMA may disclose to COMPANY under this Agreement that is marked Confidential, and if disclosed orally is reduced to writing and marked Confidential within thirty (30) days of such disclosure.

1.8 "PHARMA Experimental Data" means experimental data generated by PHARMA in both preclinical and clinical therapeutic areas, submitted to COMPANY under a User-Specified Goal Service Request. All PHARMA Experimental Data are also PHARMA Confidential Information, whether or not marked as such, and are exclusively owned and controlled by PHARMA with respect to COMPANY.

1.9 "Service Specific ABRS Biomedical Model (ABRS-BM)" means those causal network statements created by the ABRS in the course of conducting Services, that are used to analyze PHARMA Experimental Data and/ or PHARMA Confidential Information and that incorporate information from PHARMA Experimental Data and or PHARMA Confidential Information. All assertions within ABRS-BM shall be associated with their source attributions.

2.0 "Results" means all data, reports and deliverables, hypotheses, and identified biomarkers generated by COMPANY under this Agreement, as specified in each Service Request.

2.1 "Services" shall mean work by COMPANY employing ABRS Technology pursuant to this Agreement. Services to be performed are based on COMPANY'S written proposals (each a "Proposal") in response to electronically submitted User-Specified Goal directives comprising one or more research service requests for a PHARMA project from PHARMA (each a "Service Request") as provided below.

2.2 "Term" means twelve (12) months from the date of execution of this Agreement by COMPANY or completion of the Services, whichever is earlier, or unless earlier terminated pursuant to this Agreement." [etc., followed by other contract terms].

Figure 19:
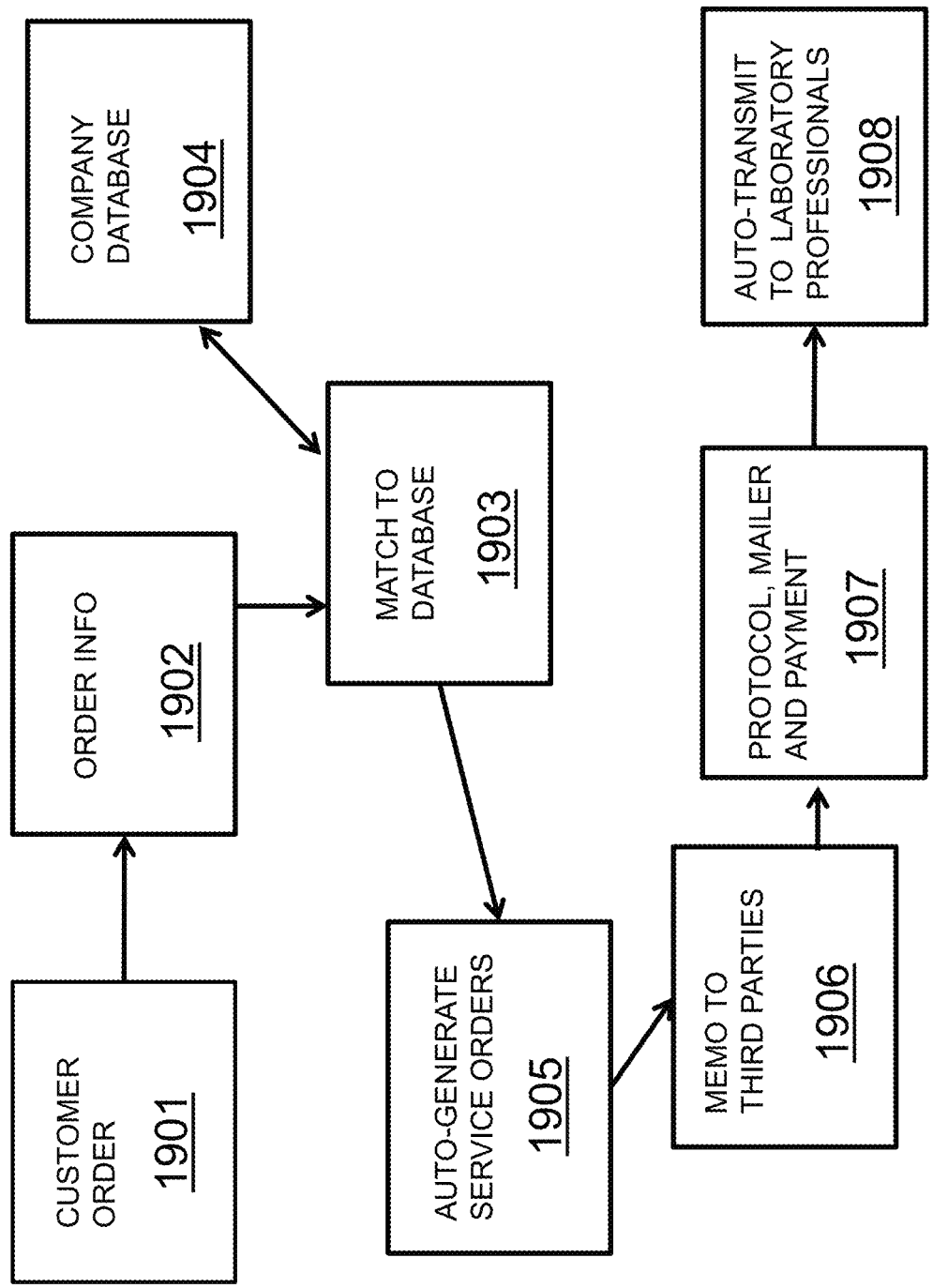
FIG. 19 illustrates aspects of a business method for automated research system services according to an embodiment of the invention.

FIG. 19 illustrated series of Business Method steps according to an embodiment, and illustrates semi-supervised business steps according to a further embodiment, wherein: at step 1901 a customer places an order; at step 1902 the order information is received and/or registered and/or recorded; at step 1903 the order information is matched against a database listing 1904; at step 1905 a service order is generated, which can be an automated step; at step 1906 a service order memo is created in email and or printed (in which fields are automatically filled in from the order information and/or the database information extracted in correspondence to the order information. The memo can read as follows, or in similar fashion:

"Dear <<AUTOMATIC LAB SERVICE PROVIDER>> Please carry out standard procedure <<EO I>> for customer <<XYZ>>. Attached are EO procedure protocols, Agreement terms and payment details. Sincerely, <<SSP Company>>"

At step 1907 the Experimental procedure is specified from a rule-based software engine that links the customer information and desired location for the procedure to appropriate and available protocols that are stored and indexed in the ARS Company database (which can include specific protocols for the Experiment Object, a mailer specification and label are generated, and payment to the automated lab service provider is detailed and scheduled; and step 1908 is transmission of the completed service order to the lab. Steps 1906, 1907 and 1908 can be automated.

Figure 20:
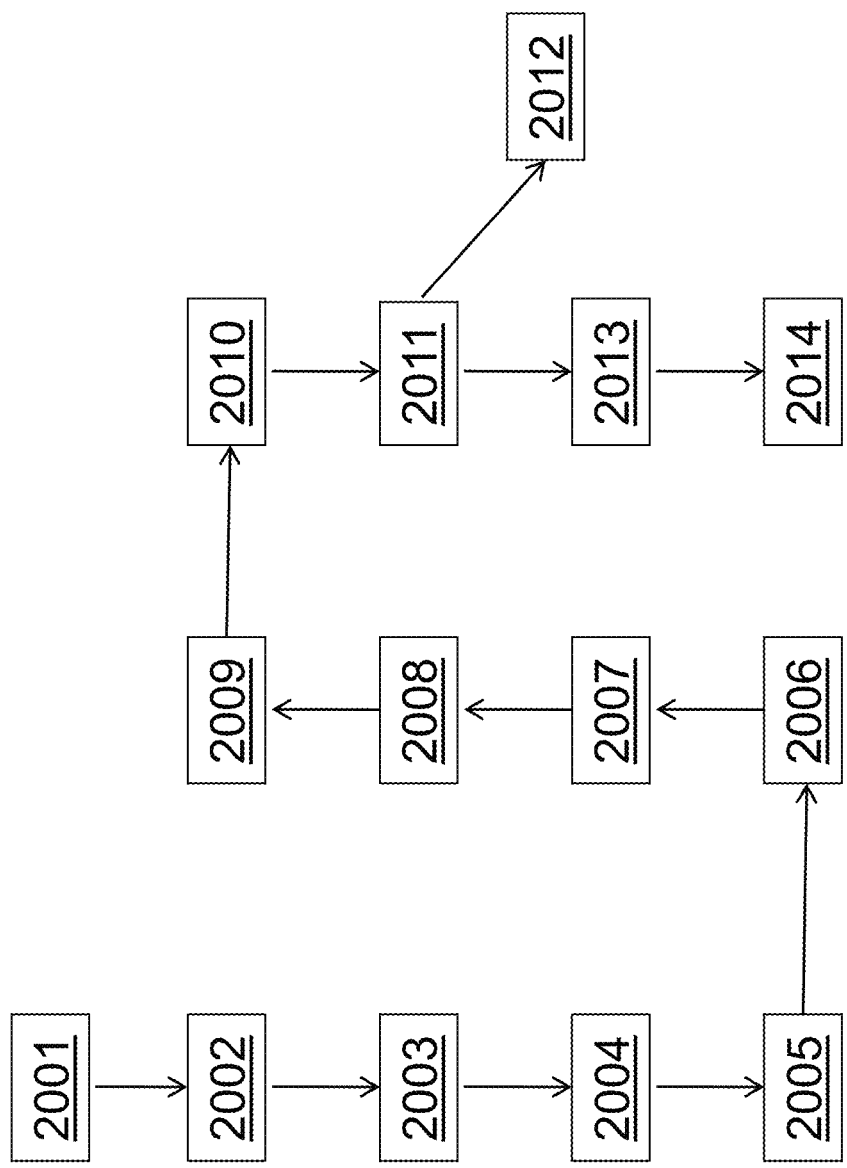
FIG. 20 illustrates aspects of a business method for selling and purchasing automated research system services according to an embodiment of the invention.

A further embodiment provides another example, illustrated by reference to FIG. 20, of a sequence of business steps according to the invention. FIG. 20 generally shows a flow chart describing a Web-based ordering process that is connected to automated generation of service-order that direct the steps of performing automated experiment service steps, reporting and delivering data results to a customer; and/or delivering to the customer digital keys to access the knowledge base, and/or code-release keys to initiate electronic delivery of the stored data results from a server. In more detail, the following steps are illustrated in FIG. 20: At step 2001, a customer accesses a web site that offers the automated experiment service product. At step 2002, the customer orders services on the web site, such as, for example, providing experiment domain and user-specified goal information, providing dates, choosing level of service, entering data or meta-data to be included later in (or on) the results. This information can include names, dates, prior experiment and/or data history, inter alia. as well as information that may be subsequently and automatically pulled from other $3^{rd}$ party databases through the Internet in response to information entered by the customer. At step 2003, the customer pre-pays for automated services (such as, for example, paying by credit card, or paying by passthrough billing to an automated laboratory and/or through collaboration fees). At step 2004, the customer agrees to a binding contract (including, without limitation, a legal electronic signature, a waiver concerning liability, and/or the customer expressly assuming risk and liability on behalf of the experiment, or the risk is partitioned).

At step 2005, the ARS company server connects the customer's order information to a ARS company database or to one or more $3^{rd}$ party databases to obtain additional data or information to be used in generating a service order and/or used in subsequent formation and delivery of the service, such as, without limitation, information about procedures, locations, practitioners, laboratories, regulations, materials, costs, risks, probabilities, service delivery, postal delivery, scientific data, data analysis and other information related to the customer-provided information and/or related to information needed for the service order. Typically, this data will be pulled from the ARS company and $3^{rd}$ party databases by software program routines that automatically generate the service order; some of this information can be independent of the information provided by the customer's order entry, while other information can be dependent upon the customer's order entries. At step 2006, the company software automatically generates a service order to participating laboratories and/or other service providers. At step 2007, the ARS company software transmits electronically the Service Orders and portion of prepayment to the laboratory (optionally including a preaddressed postal or courier mailer envelope that can be subsequently used by the laboratory professional(s) to send the results directly to the customer if requested). At step 2006, the laboratory services are performed by the professional practitioners in the automated experiment chamber (for example, without limitation the Experiment Object is parsed by the ExpDir module and the Exp Controller directs the initiation of the experiment at the laboratory, samples delivered labeled with data and/or code tracking information if applicable). At step 2009, data is entered by laboratory professionals, converted and/or transferred automatically onto the data component that is to be stored with the results (such as, for example, information about customer, experiment, the experiment sequence and/or protocol, the sampling, data processing and analysis procedures. At step 2010 the data component is merged with the results onto the ARS server, such as by an automated electronic transmission procedure. At step 2011, the results report is packaged in a transmission, which can be an electronic report that has been preaddressed to the customer or to a centralized server facility (such as described at step 2007 above) or which can be an electronic, data-structure packaging for electronic transmission directly to a data processing module and/or DAE module. At step 2012, the transmission is sent/delivered to the customer, or at step 2013, the package can be sent to a centralized domain knowledge base server or to a $3^{rd}$ party, such as a collaborator handling the next stage of the R&D. At step 2014, a code or key can be sent to the customer allowing later recovery from the server facility or knowledge base (where the code can be a digital password that allows the customer to signal a server to automatically transmit the stored data to the customer or to another $3^{rd}$ party).

Figure 21:
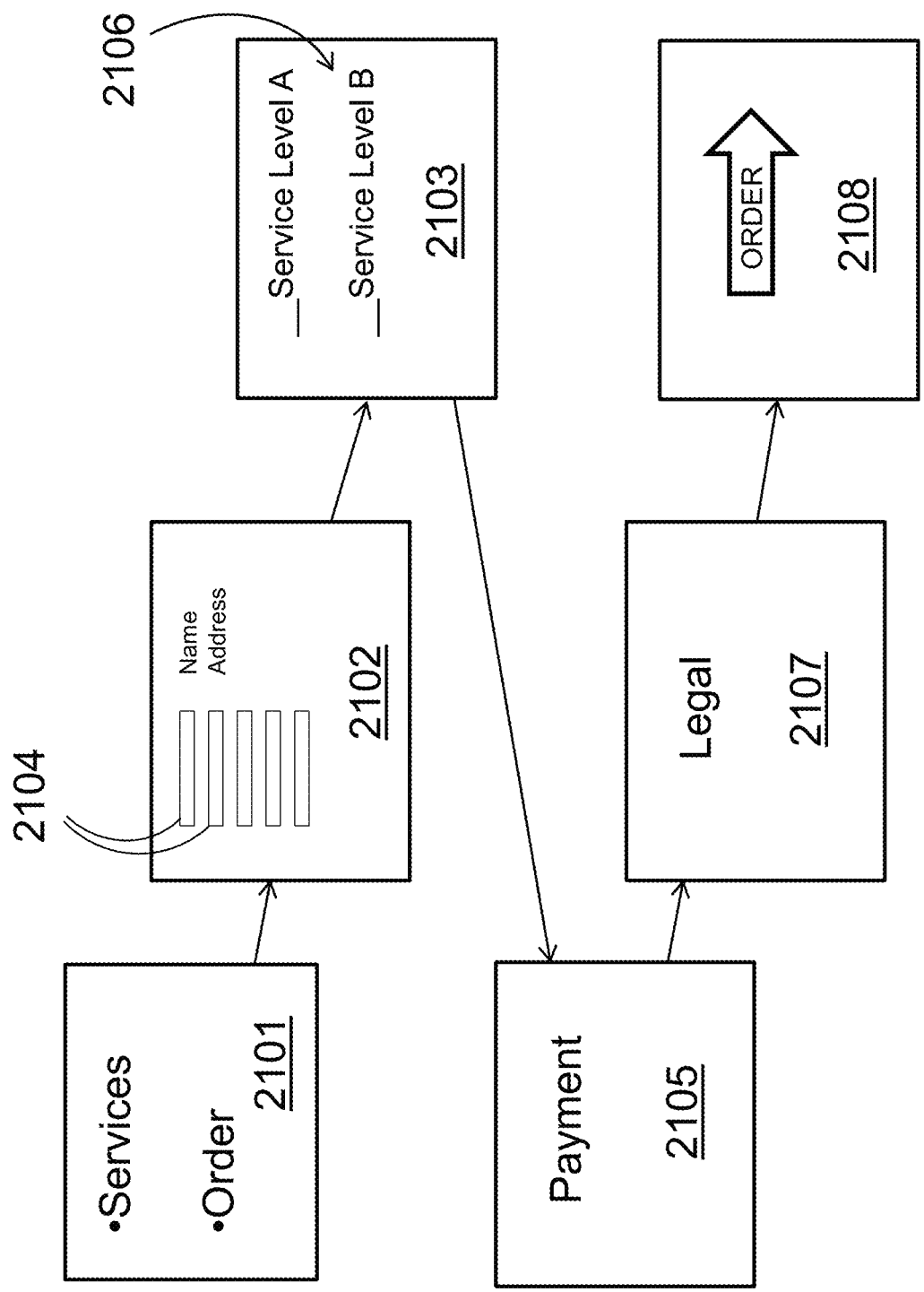
FIG. 21

FIG. 21 illustrates a succession of web pages or web screens that can appear according to an embodiment as part of the business method of providing an offer to a potential customer and the recording of order information and completion of the ordering transaction, wherein: a first business offering web page 2101 can present to the customer a choice of obtaining a description of services and/or a hyperlink to begin an order; a subsequent web page 2102 can include data-entry (or text-entry) windows 2104, which can include pull-down data selection windows (or menus of participating professionals, automated laboratory services), for the customer to enter identifying and transaction information, such as but not limited to customer name and address, experiment desired (or estimated sampling procedure required); a further secondary screen 2103 containing level of service choices 2106 (e.g., an inexpensive customer option can include simplest lab method, with results simply delivered to customer, whereas a more expensive option may include an expensive data analysis method, modeling and simulation analysis, etc., being more elaborate and/or complete, then a further secondary screen 2105 providing cost, invoice and/or payment information (for example, without limitation, an initial order fee, a experiment preparation fee, a results report and delivery, shipping fees if applicable, if the ARS Company is providing licensed subscription, an annual subscription fee); a further web-page screen 2107 providing legal terms, which screen can include an interactive button to register customer's agreement to the legal terms (such as, without limitation, providing Regulatory Documents); and, inter alia. a further page 2106 that can include an interactive button ("ORDER") to cause the order to be generated, and/or to initiate the processing of the submitted order, i.e. initiating the automated research.

Figure 22:
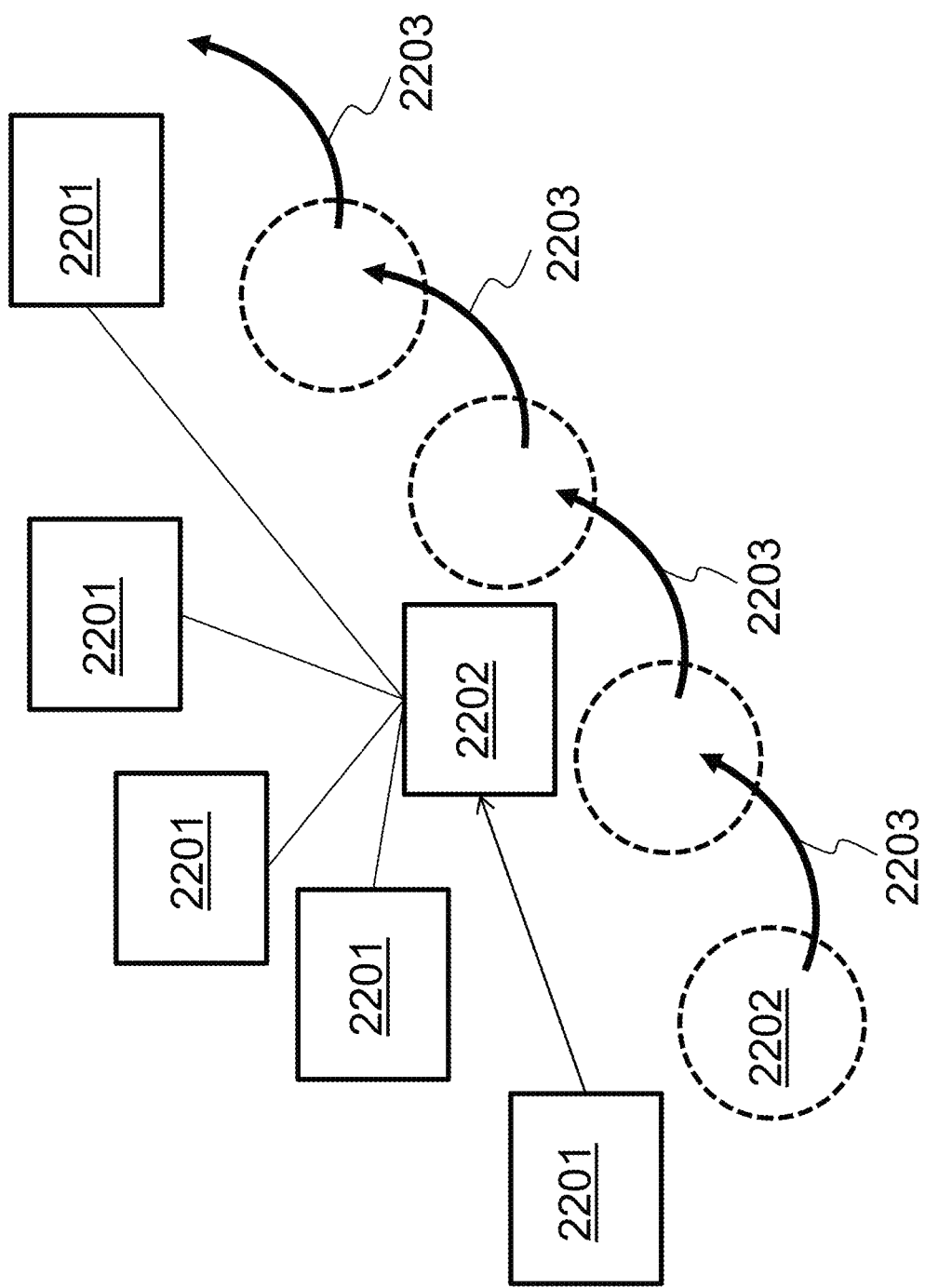
FIG. 22 illustrates aspects of a business method for multi-party collaboration using automated research system services according to an embodiment of the invention.

Referring to FIG. 22, according to an embodiment of the invention, automated research system services can be used as an aspect of a business method for multi-party collaboration 2202, wherein successive stages 2203 of R&D 2200 can be created by multiple parties 2201 interacting to promote the automated research progression.

Architecture: Modularizing Control Code in EOs

In another aspect of the subject invention, a standards-based model can be employed to modularize the control code into easily testable blocks. By applying and using modules as the building blocks for each Experimental Object application, the creator of the EOs are able to test each of the components, one at a time. This provides a systematic testing protocol. As the solutions presented by the EOs incorporating sub-EO techniques grow, the higher order modules are built upon tested and approved modules. The testing of the higher order modules can be limited to the new code in the higher order modules.

In yet another aspect thereof, a rules-base engine is utilized which accommodates decision-making for research laboratory processes, as well as steady-state and long-term projections for high-level research process decisions (e.g., minutes, hours, and days between decisions). This decision-making capability enables the equipment and/or research tools to achieve faster performance (throughput) for multiple, distributed end users. The rules engine provides an environment for sophisticated programming of continuous and discontinuous expert-based decision making procedures with regard to lab research processes in a manner understandable to non-process experts, non-batch experts and non-control experts. This is applicable also to ease of use, system maintainability, repeatability, testability, reduction of complexity, programming/development efficiency.

Preferred embodiments of the subject invention achieve improved learning, research process and laboratory equipment utilization and enhanced experimental results in the conduct of investigating one or more studied systems (such as, e.g., environmental or biological systems, by implementing a smart rules engine in conjunction with Experiment Objects that can automatically direct laboratory experiments. The experiment objects (EOs), in a preferred embodiment, can be developed by many different groups, persons or companies having ordinary skill in the art, using the ISA S88.01 International Batch Control Standard (hereinafter "S88"). A rules engine can be employed with the standards-based control code in order to optimize the flow of experimental control through an individual piece of equipment or group(s) of equipment (such as a research robot and/or an automated laboratory). The S88 methodology provides opportunities for modularity and standardization which is strongly compatible with an object oriented design. Standard instrumentation protocols, and equipment configurations, for example, can be grouped into Equipment Modules (EM) classes and control module classes. The EM is a grouping of control modules that represent process functionality, wherein the control modules are equipment used in the process. A symbol is provided for each state of the EM. The control module provides a symbol for each operator interface (e.g., auto-manual switches), a symbol for each control system input and output, and a definition of the control logic of the control module. Each instance of a module class is easily linked to unique field devices and equipment using aliases.

An embodiment of the invention provides for utilizing the S88 standards-based model to modularize experimental control code into easily maintainable modules. Each module can have a standard communication protocol to interact with another module. Functionality within the module is documented and isolated from other modules. By separating and isolating the modules, when a change or a problem occurs it is easier to isolate the module that corresponds to the required functional module. The overall solution is assembled from the modular structure. The solution can be controlled and monitored by a commercial, S88-based software package.

This standardization can start with automation software within the research equipment in an automated lab and/or can extend to automation directive software in the EOs and in an experiment control module of the automated research system, creating a lower cost, more reliable solution and ends with an interconnected, information-enabled research environment that can utilize process data to optimize the process within a piece of equipment or across multiple pieces of equipment.

The rules-base engine accommodates decision making for high-speed processes (which in one preferred embodiment of the invention can be on the order of about 10 msec per decision), as well as steady-state and long-term projections for high-level process decisions (e.g., minutes, hours, and days between decisions). This high-speed decision-making capability enables the equipment to achieve faster performance (throughput) for end users.

An embodiment of the invention increases functionality by applying the S88 architecture at the controller level along with S88-based supervisory software. All equipment functionality can be broken down into elementary control and equipment modules. Supervisory execution software can then used to link these equipment modules into deterministic sequences to support the overall experimental procedure specifications. This separation of equipment control and supervisory execution supports the capability to create any allowable sequencing of events across the equipment, thereby increasing the overall functionality of the integrated, distributed laboratory. Rather than being constrained by conventional "hardwired" sequencing control strategies, the developer and end user now have the flexibility to provide any required sequence of events across the research laboratory or many laboratories.

The rules engine provides an environment for sophisticated programming of continuous and discontinuous expert-based decision-making procedures in a manner understandable to non-process experts, non-batch experts and non-control experts. This is applicable also to ease of use, system maintainability, repeatability, testability, reduction of complexity, programming/development efficiency.

This innovation significantly reduces the cost of developing new equipment, maintaining existing equipment, trouble shooting field problems, and retrofitting/updating existing equipment.

Although the description focuses on the S88 architecture, other similar modularization architectures (e.g., object-oriented designs) can be employed in combination with the rules-based engine in order to achieve the benefits described herein with respect to the S88 architecture.

Figure 23:
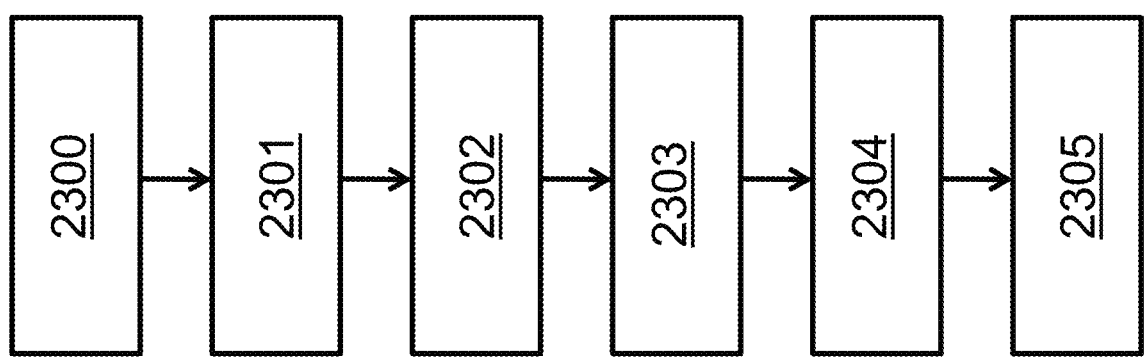
FIG. 23 illustrates automated research control steps according to an embodiment of the invention.

Referring now to FIG. 23, there is illustrated a methodology of object oriented and rules-based lab research process monitor and control in accordance with the invention. While, for purposes of simplicity of explanation, the one or more methodologies shown herein, e.g., in the form of a flow chart, are shown and described as a series of acts, it is to be understood and appreciated that the subject invention is not limited by the order of acts, as some acts may, in accordance with the invention, occur in a different order and/or concurrently with other acts from that shown and described herein. For example, those skilled in the art will understand and appreciate that a methodology could alternatively be represented as a series of interrelated states or events, such as in a state diagram. Moreover, not all illustrated acts may be required to implement a methodology in accordance with the invention.

FIG. 23 illustrates a methodology of object-oriented and rules-based process monitor and control in accordance with the invention, where the Experiment Director can control the automated laboratory process at step 2300 as the program receives the process, at step 2301 the S88 model modularizes code module(s), at step 2302 invoke the communications protocol, at 2303 load the code modules, at 2304 use the rule-engine to make research decisions and at 2305 make process adjustments. In slightly more detail, at 2300, a research process (such as a biomedical research process) is received for control and data acquisition. At 2301, a standards-based model (e.g., S88) is employed that is based on control code modularized into libraries of code modules. At 2302, a communications protocol is provided for inter-module communications, which protocol standardizes communications between most, if not all, of the code modules. At 2303, one or more code modules are loaded into compatible automated experimental process devices for execution to control one or more pieces of automated research equipment. At 2304, the rules engine is employed in communication with devices and/or code modules such that rules which are written can be imposed by execution via the rules-engine in the Experiment Director Module to make intelligent decisions in real-time associated with, for example, corrections and adjustments of research process conditions, as indicated at 2305. This facilitates optimization of at least process flow, device use, and experimental result throughput.

Figure 24:
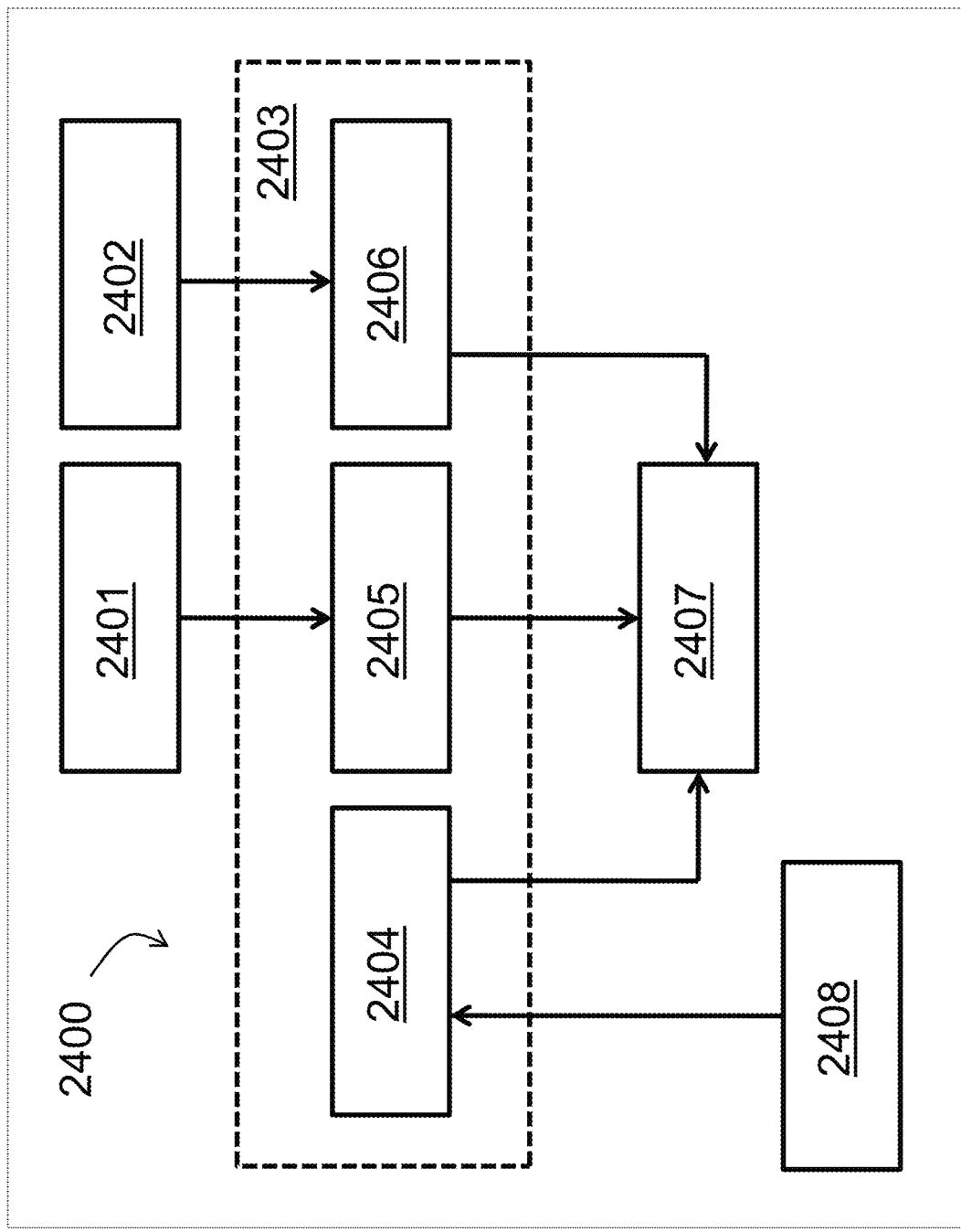
FIG. 24 illustrates automated device control functions according to an embodiment of the invention.

FIG. 24 illustrates a system 2400 of devices that can be employed and configured for process control in accordance with the invention. Depicted is a plurality of the devices 2403 (denoted as DEVICE.sub.1, DEVICE.sub.2, . . . , DEVICE.sub.M) that can be utilized to instrument one or more processes and associated equipment (denoted collectively as 2407). Each of the devices 2403 can be used for a different purpose. For example, a first device 2404 can be used to control a robot arm, and a second device 2405 can be configured to monitor and control a process chamber, such as an incubator. Accordingly, the first device 2404 will be loaded with one or more code modules 2408 (denoted as MODULE.sub.1, . . . , MODULE.sub.N) that perform dedicated functions for which the first device is assigned. Similarly, the second device 2405 can be loaded with one or more code modules 2401 (denoted MODULE.sub.1, . . . , MODULE.sub.X) that form the modularized code needed for operation and functioning of the second device to monitor and control the process chamber of the equipment/process 2407. Furthermore, the system 2400 can include an Mth device 2406 utilized for data acquisition of various sensor measurements associated with the equipment and/or process 2407. Accordingly, the device 2406 includes one or more code modules 2402 (denoted as MODULE.sub. 1, . . . , MODULE.sub.Y) which are uploaded thereinto for acquiring data and operation of the device 2406.

The modules 2408 of the first device 2404 intercommunicate with each other via the standardized communications protocol. Similarly, modules 2401 of the second device 2405 intercommunicate with each other via the standardized communications protocol, and modules 2402 of the Mth device 2406 communicate with each other via the standardized communications protocol. It is further to be appreciated that since the code modules (2408, 2401, and 2402) intercommunicate with the standardized protocol, inter-module communications can also occur inter-device. In other words, the first module (denoted MODULE.sub.1) of the first device 2404 can communicate across a communications network (or bus) to a first module (denoted MODULE.sub.1) of the second device 2405. Moreover, some of the modules employed in the devices (2404, 2405, and 2406) can be the same. For example, the first modules (denoted MODULE.sub.1) of each device (2404, 2405, or 2406) can be code that performs basic setup and configuration of the device, where the devices are the same model, etc. Yet other code modules loaded thereinto facilitate operation and functionality for different purposes related to the equipment and/or part of the process to be instrumented.

Figure 25:
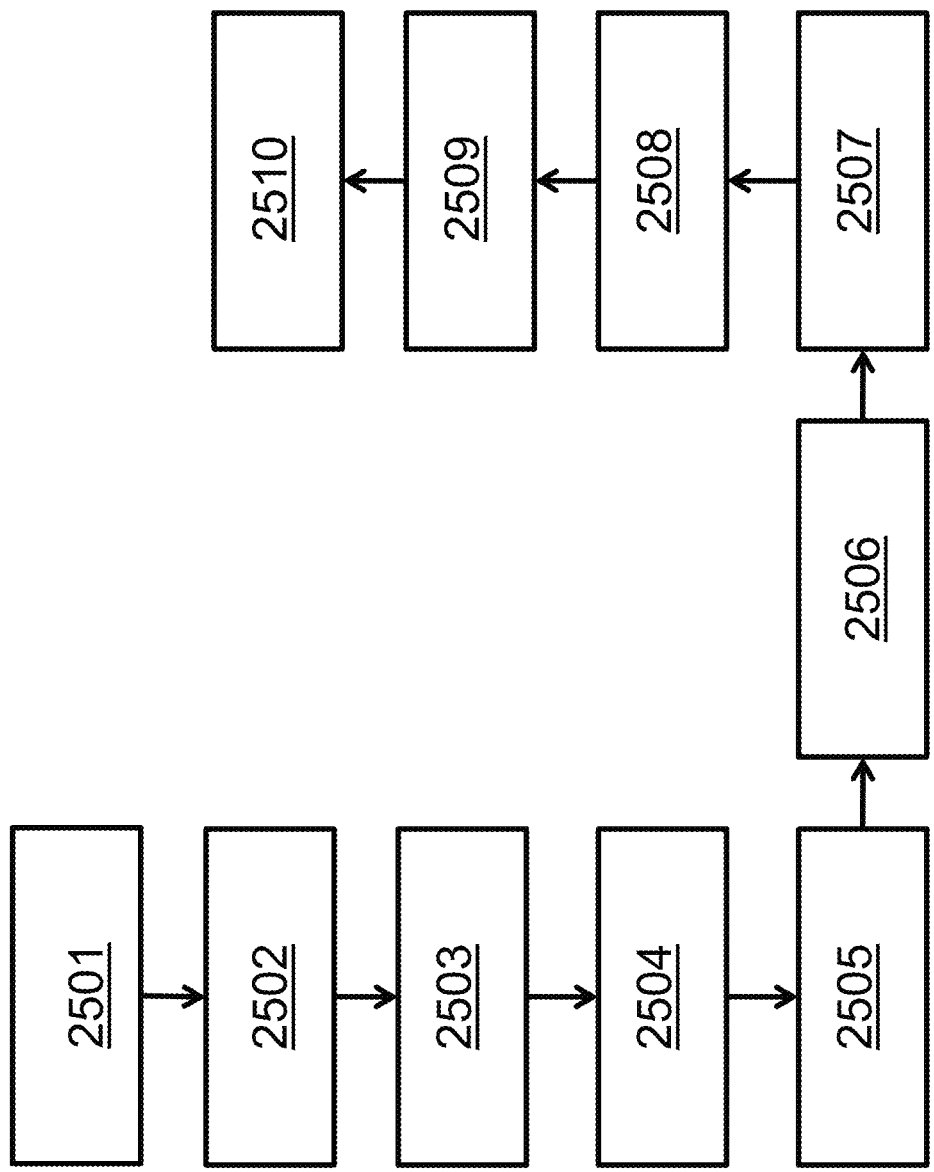
FIG. 25 illustrates research modeling components for an automated, integrated, monitoring, modeling and management (AIM3) energy resources learning model according to a preferred embodiment.

FIG. 25 illustrates a method of device preparation and operation for a process in accordance with the invention. At step 2501, the EO process to be performed is determined. At step 2502, one or more tools in an Experiment Chamber are assigned to the process. At step 2503, a device is assigned to the process and/or process equipment for toll control and/or data acquisition. At step 2504, modules compatible with the selected device are selected and uploaded to the device. At step 2505, one or more of the uploaded code modules are tested in the device. At step 2506, the device can then be installed in the system. Note that it is to be appreciated that the device can already be installed in the system such that a tool replacement is required and not the device itself. The process is then started, as indicated at step 2507. At step 2508, rules are imposed and executed before, during, and/or after the experimental process runs to make adjustments and/or corrections to optimize system processes, for example. At step 2509, device software modules parameters can be adjusted in real-time according to the rules to account for process changes and/or equipment wear and failure.

A preferred embodiment provides for a methodology of implementing parallel devices for a critical process in accordance with the invention. The critical process is determined and two or more devices can be selected and assigned to the process. Note that the two or more devices can be the same or different, which is not a limiting factor, since the code modules are optimized for the given device model. Supervisory control exists for any device type, since inter-module communications is according to a standard protocol. At step 2508, Rules can be imposed and executed to determine device integrity and health of the device and associated tools and process being controlled and/or monitored. If a change is not detected in a first device, parameter, tool or the process, flow is returned to continue rules execution for determining if changes have occurred. If changes have occurred, flow is passed to second or third devices, and can even move the affected first device offline, leaving the second device online to handle the processing required. While offline, a diagnostics module of the changed device can be executed (step 2510) to determine a cause of the change.

Artificial Intelligence Components to Automate Features of Automated Research

In still another aspect of the invention, an artificial intelligence component is provided that employs a probabilistic and/or statistically-based analysis to prognose or infer an action that a user desires to be automatically performed.
Programming An ARS according to one embodiment of the invention can be programmed by one of ordinary skill in the art using a number of build environments (such as, for example, MS Visual Studio; MS InterDev; C++; Java; RDF/XML/OWL.

In a preferred embodiment of the invention, object-oriented programming (OOP) approaches are used to build software objects, such as, for example, without limitation as to numbers of object categories or number of objects per category:

1. Automated Laboratory Objects
   Laboratory Control Objects
   Robot and Automated Instrument Driver Objects
   Sample and Materials-Handling Objects
   Annotation Tracking Objects
   Laboratory Information Management System Objects
   Variable/data acquisition and recording Objects
   Laboratory Resources Objects
   Laboratory Contract Services Objects
   Laboratory Technical Objects
   Laboratory Experiment Controller Objects
   Environmental sampling control objects
   Laboratory QMS documentation management objects
   Laboratory Safety Objects
2. Experimental Director Objects
   Experiment Design Objects
   Parameter List Objects
   Parameter Uncertainty Objects
   Constraint-Modeling Objects
   Hypothesis-Formation Objects
   Value-of-Information Objects
   Goal Objects
      Goal Seeking Objects
      Goal Creation Object
   Experiment Chooser Objects
   Experiment Chooser Rule-Engine Object
   Experiment Director Experiment Controller Objects
   Quality Assurance/Quality Control Objects
   QMS documentation management objects
   Experiment Safety objects
3. Data Analysis Objects
   Data Analysis Rule-Engine Objects
   Data Processing Objects
      Image processing objects
      Data Annotation Tracking Objects
      Data normalization Objects
      Data Tabulation and Graphing Objects
   Statistical Analysis objects (OTS-Spotfire; GeneLinker-Platinum)
   Association Mining and Reverse Engineering Objects (GL-P)
   Math Solver Objects/Algorithm Objects [numerous]
4. Dynamic Modeling and Simulation Objects
   I/O exchange/transaction objects
   Structural & Network Graph Differentiation Objects
   Self-organization-level Objects
   Hierarchical Nesting Objects
   Node/Component Interaction Objects
   Nested dynamics sequencing objects
   Dynamic modeling parameter objects
   Simulation Run Objects
   Positive Feedback Modeling Object (system invokes when certain conditions met)
   Negative Feedback Modeling Object
5. Knowledge Base Assembly Objects
   Knowledge Base access and update objects
   Congruence testing objects
   Fitness measure objects
   Ontology objects
   Pathway objects
   Bayesian Inference Objects
   Causal Networks objects
   Signaling objects 6. Query Manager Objects
Query formulation and SQL objects
Network access objects
Knowledge base parsing objects
User-interactive I/O objects
User-Specified Goal definition objects
User Business Broker objects
7. User Interface Objects
GUI and visualization objects
User customization objects
8. Database and DB Management Objects
Information Library Objects (interact w/Ontology Objects)
   Domain Ontologies and Semantic Web objects
Library of Possible Experiment Objects
   Experiment Objects
      Experimental Technique Objects
      Experimental Equipment Menu Objects
      Experimental Procedure Objects
      Experimental Outcomes Objects
      Experimental Materials Objects
      Experimental Equipment Control Objects
      Experimental Sequencing/Scheduling Objects
      Experimental Costing Objects
      Experimental Sourcing/Siting Objects
      Experimental Technical Objects
      Experimental Variable/Data Objects
      Experimental Contract Services Objects
      Experimental QMS/Regulatory Objects
      Experimental Safety Objects
      Experimental IP Ownership Objects
9. Business Objects
Business Method Management objects
   ARS owner hosting/subscriber objects
   Transaction templates objects
   Contract Brokering objects
   Contact Management support objects
RFP/Proposal management objects
Market analysis objects
Price modeling and quantity adjustment objects
Legal objects
   Template terms objects
   Royalties terms and calculations objects
   IP ownership and FTO analysis objects
   Licensing and contract terms and adjustments objects
   Warranty and indemnification objects
   Arbitration terms and management objects
   Regulatory and QMS certification objects
Budgeting analysis and assistance objects
Risk analysis objects
Web 2.0 Social Networking Interface Objects It will be appreciated that the ARS described herein in certain embodiments, including pseudo-code illustrating the methods and system of embodiments of the invention, can be implemented by one skilled in the art of software programming in one or more different programming languages, or combinations of programming languages, including, for example, such languages and programming tools and approaches as object-oriented programming (or OOP, including, without limitation, software objects, software classes, databases, loops, relational operators, pointers, inheritance, polymorphism), C#(including C# version 3.0), JavaScript, Python, C++, C, Perl, Visual Basic, PHP, Asynchronous Javascript and XML (AJAX), the .NET Framework 3.5, ASP.NET 3.5 and ASP.NET AJAX, Database/SQL/LINQ, XML/LINQ, WCF Web Services, OOD/UML, XAML, Visual Studio 2008, SQL Server Express, Transaction-Structured Query Language (T-SQL), HTML, XHTML, DOM API, XSLT and XPATH, CSS, XML, SVG, HTTP, SQL, XForms, WS-* Services and SOAP, CORBA, DAML+OIL, RDF, OWL, Web 2.0, WSDL, WS-* Services and WSDL, JSON, Java Servlets, secure socket layers (SSL), Mashups, RSS, Atom Syndication Format (ASF), AtomPub, web-based ontologies, and further using, among other known and described programming methods and approaches, the programming methods, routines, techniques and technologies known to practitioners and described in the following treatises, which are each incorporated herein in their entirety: "Ajax Bible." Steve Holzner. Wiley Publishing, Inc., 2007, Indianapolis, Ind. 695 pp.; "C#2008 for Programmers. Third Edition (Deitel Developer Series). Paul J. Deitel and Harvey M. Deitel. Prentice Hall, New York N.Y., 2008. 1251 pp.; "Programming Python." Mark Lutz, O'Reilly Media, Inc., Sepastapol, Calif. 2006. 1552 pp.; "Pro T-SQL 2008 Programmer's Guide, "Michael Coles, Apress, Berkely Calif. (2008), 659 pp.; "Professional Web 2.0 Programming," Eric van der Vlist, Danny Ayers, Erik Bruchez, Joe Fawcett, Alessandro Vernet, 2007, Wiley Publishing, Indianapolis, Ind. 522 pp.; "Beginning C#3.0: An introduction to Object-Oriented Programming," Jack Purdum, 2007, (Wrox) Wiley Publishing, Inc., Indianapolis, Ind. 523 pp.

The Data Analysis Engine (DAE) module according to one embodiment can be programmed readily by one skilled having ordinary skill the art following methods outlined in "Introduction to Combinatorial Analysis, John Riordan, Dover Publications, Mineola, N.Y., (2002), hereby incorporated herein by reference in its entirety, and can include any one or more of methods for combinatorial analysis, including without limitation, permutations, partitions, compositions, trees, networks, functions, inclusion and exclusion.

One embodiment of the ARS according to the invention provides for an automated research system prediction of next-round (or next loop) experimental results to be able to satisfy the new constraints in the structured data of the newly updated knowledge base (updated by the new experimental results), which can utilize a multitude of well-known methods for pattern recognition and machine learning, including without limitation Bayesian regression and Bayes model comparison, probabilistic discriminative models, discriminant functions, neural networks, sparse kernel methods, Markov Random fields, K-means clustering, approximate inference, sampling (including Markov chain Monte Carlo, Gibbs sampling and hidden Markov models), kernel-Hilbert spaces, support vector machines (SVMs), regression for string-to-string mapping, energy-based models and linear dynamical systems (LDS) analysis, any and all of which can be programmed by a person having ordinary skill in the art with reference to and guidance from "Pattern Recognition and Machine Learning," Christopher M. Bishop, Springer (2006), 738 pp., which is hereby incorporate by reference herein in its entirety.

Additional aspects of the reverse-engineering function in the DAE and Modeling modules can be programmed by one having ordinary skill with guidance found in "Artificial Intelligence: Sixth Edition: Structure and Strategies for Complex problem Solving, George F. Luger, Addison Wesley/Pearson, (2008), 754 pp., and in "Paradigm of Artificial intelligence Case Studies in Common LISP", Peter Norvig, (1992), Morgan Kaufmann, both hereby entirely incorporated by reference herein, including such methods and approaches as, without limitation, PROLOG, LISP, symbol-based machine learning, ID3 Decision tree Induction, unsupervised learning, version space search, perceptron learning, back-propagation learning (such as, for example, NETtalk), and natural language programming (NLP).

Optimization of any step in the ARS modules, including for example, optimization in Experimental Chooser and optimizing fit of Congruence Module with the user-specified goals and change in the knowledge base, can be programmed using any methods outlined by M. Athans and P. L Falb in "Optimal Control: An Introduction to the Theory and Applications, Dover Publications, Mineola, N.Y., (2007), 877 pp., which is hereby incorporated herein by reference in its entirety.

The DAE and Modeling modules can include, through distributed access, any number of analytical functions that can operate on data, wherein a preferred embodiment of the invention can include at least filtering, regression and correlation, a more preferred embodiment can additionally include one or more of recursion analysis, hash tables, binary search trees and B-trees, and a most preferred embodiment can additionally include methods for sub-linear association mining (SLAM), integrated Bayesian Inference (IBIS), self-organizing maps (SOMs), and reverse-engineering, among other algorithms, wherein these module can be programmed accordingly by one having ordinary skill in the art and using such techniques, methods and approaches as are provided in Brian D. O. Anderson, "Optimal Filtering, "Dover Publications (2005), Mineola, N.Y., 357 pp.; in "Mathematical Techniques for Biology and Medicine, William Simon, (1987), Dover Publications, New York, N.Y., 295 pp.; in "Introduction to Algorithms, $2^{nd}$ Edition, Thomas H. Cormen et al., MIT Press, Cambridge, Mass., (2001); "Statistical Digital Signal Processing and Modeling", Monson H. Hayes, John Wiley & Sons (1996), 608 pp.; and in "Pattern Classification, $2^{nd}$ Edition", Richard O. Duda, Peter E. Hart and David G. Stork, (2001), J. Wiley and Sons; all of teachings are hereby incorporated herein by reference in their entirety.

Modeling Module (MM) The Modeling Module and/or Congruence Module can be used in developing and/or combining a domain knowledge base in conjunction with a domain-specific dynamic model (or simulation). The ARS can add and integrate through its modeling module one or more of a set of principles of general systems and principles of energetics associated with general systems models and/or the domain-specific models of the studied system. This can include, e.g., functions such as growth model functions, competition, structures, cooperation, decomposition, aggregation, decentralization, perturbation, stability, decentralized control, hierarchical models, subsystem analysis, and stability regions, among others, and these principles can be programmed readily by a person having ordinary skill in the art from methods described by Dragislov D. Siljak, in "Large-Scale Dynamic Systems: Stability and Structure," (1978), Dover Publications, Mineola, N.Y., 416 pp., and from methods described in "Predicting Structured Data," MIT Press, Cambridge, Mass., edited by Gokhan Bakir et al., (2007), both of which are hereby incorporated by reference herein in their entirety.

Data Analysis Engine (DAE) and Congruence Module—Knowledge Model Assembly

The Data Analysis Engine can include specific unique and custom algorithms and/or data analysis routines and/or it can provide an interface (by 'wrapping' and/or interconnecting to) to multiple off-the-shelf (OTS) commercial software packages that are well known to those skilled in the art of data analysis, such as, for example without limitation, Rosetta®, GeneSpring®, SAS®, Excel®, Spotfire®, GeneLinker® (Integrated Outcomes Software, Kingston, Ontario) and other packages).

Additional functionality can be programmed into the DAE according to one embodiment, including evolutionary algorithms, fitness functions, multiple objective functions and constraint functions, cellular automata and neural systems, by one having ordinary skill in the art with guidance from "Bio-Inspired Artificial Intelligence: Theories, Methods and Technologies," Dario Floreano and Claudio Mattiussi, (2008), MIT Press, Cambridge Mass. 659 pp., incorporate herein in its entirety by reference hereby.

Knowledge Base and Domain Ontology

The structure of the domain knowledge base that can be utilized by an ARS according to an embodiment of the invention can be developed using methods that include, without limitation, KBs, backward and forward chaining, rule formulation and search, object-oriented representation (objects and frames), structured descriptions, taxonomies, autoepistemic logic, reasoning, vagueness principles, GOLOG, STRIPS and other aspects of semantic knowledge representation such as can be programmed by a person having ordinary skill in the art with the methods found in "Knowledge Representation and Reasoning," Ronald J. Brachman and Hector J. Levesque, Morgan Kaufman/Elsevier, New York, N.Y. (2004), 381 pp., which is incorporated herein by reference in its entirety. Further, in implementing code to direct the user interface and query manager to examine correspondence between semantically related ontologies (such as those of a prior knowledge base and of an updated knowledge base, or when simply searching for related ontologies in the domain, a programmer having skill in the art can be sufficiently guided by the methods described in "Ontology matching," Jerome Euzenat and Paul Shvaiko, Springer, (2007), 334 pp., hereby entirely incorporated herein by reference.

Experiment Chooser and Congruence Module

The Experiment Chooser (ExpCh) and Congruence Modules (CM) according to embodiment of the invention can utilize multi-objective decisions, decision rules, scaling (including nominal, ordinal, interval, ratio and multi-dimensional scaling), utility theory, vector optimization, weighting, assessment methodologies (including the ELECTRE method), priorities, goals and goal programming methods that can be readily programmed by a person having ordinary skill in the art with reference to "Multi-objective Decision Making Theory and Methodology," Vim Chankong and Yacov Y. Haimes, Dover Publications, Mineola, N.Y., (1983), 406 pp, the teachings of which are hereby incorporated herein by reference in their entirety.

Also relevant to the functionality of the Experiment Chooser, DAE and optimizing the modeling steps according to an embodiment, one having ordinary skill in the art can program functional objects for multi-objective optimization, MO-evolutionary algorithm, multi-criteria decision-making, fuzzy logic, Pareto ranking, goals, and utility functions by referring to the methods contained in "Evolutionary Algorithms for Solving Multi-Objective Problems: $2^{nd}$ Edition," Carlos A. Coello Coello, Gary Lamont and David Van Veldhuizen, Springer, (2007), 800 pp., hereby incorporated by reference herein in it entirety.

Computing System

Figure 26:
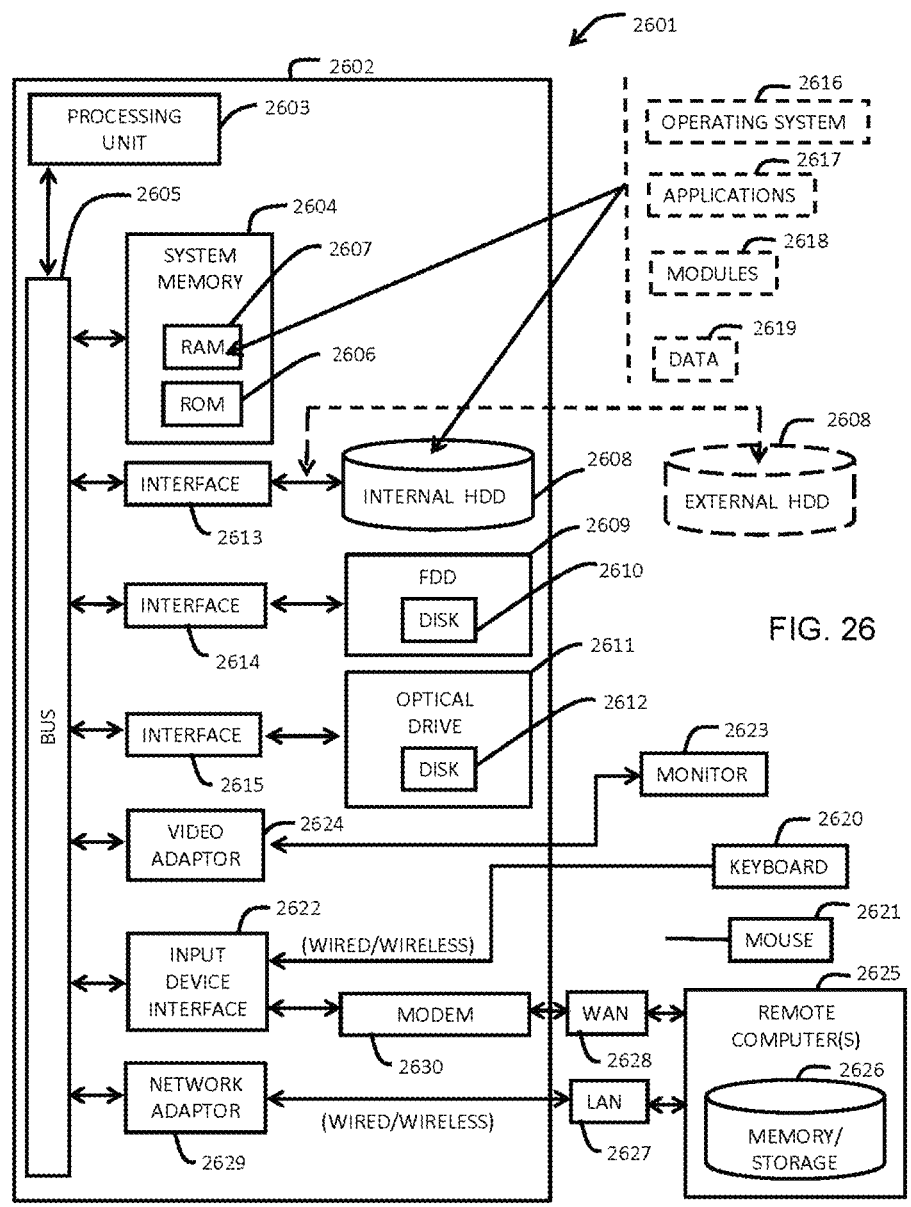
FIG. 26 is a block diagram illustrating computing hardware and network according to embodiments of the invention.

Referring now to FIG. 26, there is illustrated a block diagram of a computer operable to execute the disclosed architecture. In order to provide additional context for various aspects of the subject invention, FIG. 26 and the following discussion are intended to provide a brief, general description of a suitable computing environment 2601 in which the various aspects of the invention can be implemented. While the invention has been described above in the general context of computer-executable instructions that may run on one or more computers, those skilled in the art will recognize that the invention also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the invention may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer readable media can comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 26, there is illustrated an exemplary environment 2601 for implementing various aspects of the invention that includes a computer 2602, the computer 2602 including a processing unit 2603, a system memory 2604 and a system bus 2605. The system bus 2605 couples system components including, but not limited to, the system memory 2604 to the processing unit 2603. The processing unit 2603 can be any of various commercially available processors. Dual microprocessors and other multi-processor architectures may also be employed as the processing unit 2603.

The system bus 2605 can be any of several types of bus structure that may further interconnect to a memory bus (with or without a memory controller), a peripheral bus, and a local bus using any of a variety of commercially available bus architectures. The system memory 2604 includes read only memory (ROM) 2606 and random access memory (RAM) 2607. A basic input/output system (BIOS) is stored in a non-volatile memory 2606 such as ROM, EPROM, EEPROM, which BIOS contains the basic routines that help to transfer information between elements within the computer 2602, such as during start-up. The RAM 2607 can also include a high-speed RAM such as static RAM for caching data.

The computer 2602 further includes an internal hard disk drive (HDD) 2608 (e.g., EIDE, SATA), which internal hard disk drive 2608 may also be configured for external use in a suitable chassis (not shown), a magnetic floppy disk drive (FDD) 2609, (e.g., to read from or write to a removable diskette 2610) and an optical disk drive 2611, (e.g., reading a CD-ROM disk 2612 or, to read from or write to other high capacity optical media such as the DVD). The hard disk drive 2608, magnetic disk drive 2609 and optical disk drive 2611 can be connected to the system bus 2605 by a hard disk drive interface 2613, a magnetic disk drive interface 2614 and an optical drive interface 2615, respectively. The interface 2613 for external drive implementations includes at least one or both of Universal Serial Bus (USB) and IEEE 1394 interface technologies.

The drives and their associated computer-readable media provide nonvolatile storage of data, data structures, computer-executable instructions, and so forth. For the computer 2602, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the invention.

A number of program modules can be stored in the drives and RAM 2607, including an operating system 2616, one or more application programs 2617, other program modules 2618 and program data 2619. All or portions of the operating system, applications, modules, and/or data can also be cached in the RAM 2607. It is appreciated that the invention can be implemented with various commercially available operating systems or combinations of operating systems.

A user can enter commands and information into the computer 2602 through one or more wired/wireless input devices, e.g., a keyboard 2620 and a pointing device, such as a mouse 2621. Other input devices (not shown) may include a microphone, an IR remote control, a joystick, a game pad, a stylus pen, touch screen, or the like. These and other input devices are often connected to the processing unit 2603 through an input device interface 2622 that is coupled to the system bus 2605, but can be connected by other interfaces, such as a parallel port, an IEEE 1394 serial port, a game port, a USB port, an IR interface, etc.

A monitor 2623 or other type of display device is also connected to the system bus 2605 via an interface, such as a video adapter 2624. In addition to the monitor 2623, a computer typically includes other peripheral output devices (not shown), such as speakers, printers, etc.

The computer 2602 may operate in a networked environment using logical connections via wired and/or wireless communications to one or more remote computers, such as a remote computer(s) 2625. The remote computer(s) 2625 can be a workstation, a server computer, a router, a personal computer, portable computer, microprocessor-based entertainment appliance, a peer device or other common network node, and typically includes many or all of the elements described relative to the computer 2602, although, for purposes of brevity, only a memory storage device 2626 is illustrated. The logical connections depicted include wired/wireless connectivity to a local area network (LAN) 2627 and/or larger networks, e.g., a wide area network (WAN) 2628. Such LAN and WAN networking environments are commonplace in offices, and companies, and facilitate enterprise-wide computer networks, such as intranets, all of which may connect to a global communication network, e.g., the Internet.

When used in a LAN networking environment, the computer 2602 is connected to the local network 2627 through a wired and/or wireless communication network interface or adapter 2629. The adaptor 2629 may facilitate wired or wireless communication to the LAN 2627, which may also include a wireless access point disposed thereon for communicating with the wireless adaptor 2629.

When used in a WAN networking environment, the computer 2602 can include a modem 2630, or is connected to a communications server on the WAN 2628, or has other means for establishing communications over the WAN 2628, such as by way of the Internet. The modem 2630, which can be internal or external and a wired or wireless device, is connected to the system bus 2605 via the serial port interface 2622. In a networked environment, program modules depicted relative to the computer 2602, or portions thereof, can be stored in the remote memory/storage device 2626. It will be appreciated that the network connections shown are exemplary and other means of establishing a communications link between the computers can be used.

The computer 2602 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Advantages and Importance

The method and system according to preferred embodiments providing for automated biomedical research systems provide for more rapid and customized access to state-of-art computational analyses using an easy-to-use user interface, where researchers can access experimental techniques, results and data analyses without needing the specific expertise in-house (i.e., the expertise is made accessible via the ARS from numerous experts who build the intelligent Experiment Objects that are accessed by the system.

The innovation disclosed herein brings to the automated research industry at least the following:

Firstly, the invention facilitates standard equipment control methodologies and terminologies for automation software solutions using the S88 modularization practices and methods within the equipment, between like pieces of equipment, and across the research environment from Facility Applications (FA) to Process Tool and back end test, assembly, and related applications.

Secondly, the invention reduces costs, time to market, and increases reliability by utilizing commercial S88-based software packages to modularize the software code for greater engineering efficiency and quality.

Thirdly, improved equipment utilization and experimental result throughput is achieved by implementing the smart rules engine in conjunction with the S88-based control code in order to optimize the flow of experimental result through an individual piece of equipment or group(s) of equipment. The rules engine utilizes real-time process information and responds to system prompts to make intelligent decisions based on rule sets designed by a process expert and implemented by a control system expert.

Finally, an optimized research process is achieved by providing real-time streaming research data to achieve run-to-run comparisons, apply statistical process control, apply Adaptive Control Methodologies, enable e-bioresearch equipment evaluation with Security, and enable Genealogy for each Biotechnology and biomedical experimental result and/or individual component of new biomedical knowledge.

This innovation increases reliability by creating, testing, and implementing S88 control and equipment modules in the controller; the creation of EO recipes from this point forward includes linking together pre-tested equipment module logic, thus increasing the overall reliability of the execution layer.

One or more further aspects of the invention can be illustrated by one or more preferred embodiments which provide for a computer-based and Internet-based method of facilitating a transaction online between a customer and a third-party service provider, wherein the online method can be performed by a single facilitator company and wherein the method comprises the steps of providing an online, computer-based transaction system communicably coupled to a database, storing service-order information relating to a plurality of services and service providers in the database, wherein at least service-providers can access the database via a first interface and enter information into the database and at least one customer can access the website and/or database via a second interface, displaying on a web site offered services from the database, which step of displaying services can include providing an online presentation or menu of at least one of medical, biomedical, medical research and biomedical research services selectable by a customer, said services performable by at least one medical, biomedical, medical research and biomedical research service provider, providing an offer online to sell at least one service, detecting an order on a computer from a customer for the at least one service, generating a service order automatically by a computing module, and outputting the automatically generated service-order from a computer.

A further aspect of the invention can be illustrated by an e-commerce web site that offers at least one medical and/or biomedical service, such as, for example, providing for a parent and/or guardian of a soon-to-be born child to order, schedule and/or purchase the service of sampling, preserving and storing their child's stem cells in a manner that allows the parent easy long-term storage and control over the sample.

A further preferred embodiment of the invention provides a system for generating a stem-cell-storage service order, relative to a prospective new-born baby or an adult customer, or both, comprising: a database storing stem-cellstorage service-order information about each of a plurality of medical device service providers; and a computer system communicably coupled to the database, the computer system including computer program instructions to:

(a) provide a first user interface to accept, from a first user, an identification of one of the plurality of medical service providers and information identifying a service provider who is to be authorized to provide the service of stem-cell extraction, preservation, packaging and package delivery, relative to a baby, a customer, or both;

(b) determine if the first user is authorized to enter information into the database;

(c) if the first user is authorized, store information provided by the first user in the database in association with the one of the plurality of medical service providers;

(d) provide a second user interface to accept user credentials and an identification of one of the plurality of medical service providers, wherein the second user interface is accessible by a customer who is not the first user or one of the plurality of medical service providers;

(e) determine if the customer is authorized to generate a stem-cell-storage service-order, relative to the one of the plurality of medical service providers, comprising accessing the database to determine if the user credentials accepted from the customer by the second user interface correspond to information requirements criteria stored in the database in association with the one of the plurality of medical service providers; and (f) if the customer is authorized, generate a service order relating to the one of the plurality of medical service providers and provide the generated service order to the medical service provider.

Ordering and Purchasing Step

Upon signing up for obstetrician's care, or signing up for the hospital birthing services, or by one or more other means at a time prior and/or proximate to the child's birth, a requesting parent can order and purchase the taking of sample, and or further pre-pay for the preservation and long-term storage of the stored stem cells. For instance, FIG. 19 illustrates a sign-up or purchase/order form that can allow a parent and guardian of a soon-to-be born child and/or a newborn child to order or schedule the storage service to be conducted and to specify the delivery of the stored product to the purchasing parent and or guardian and/or to the parent or guardian's representative.

The sign-up or purchase form can be on paper, or can be electronic via the Internet and a web service. It is considered within the scope of the invention to provide a web-page presented service for such cord-blood stem cell storage, whereby the service provided arranges directly with the attending physician and/or the birthing clinic or the hospital to provide the desired storage procedure according to the service details selected.

FIGS. 4, 19, 21 and 31 illustrate a service presentation and customer sign-up procedure effected over the Internet, with the data being moved to a server and then a secondary order being placed by the service, based on the information in the form, with a forwarded order sheet being delivered by the Internet to participating medical providers, doctors, technicians, clinics and or hospitals. According to known methods, such as, for example, by use of RSA public-key encryption, this ordering service can utilize encryption to keep information confidential.

It is within the scope of the invention to provide further for automated forwarding and/or automated secondary ordering procedures, whereby the parent and or guardian requestor (or a representative of said party) can prepay for the service on a web-page, and the automated service-order is forwarded to the medical professionals and service professionals responsible for attending the birth, and whereby the stored and sealed sample is collected, extracted, preserved, contained, sealed, packaged and posted directly from the birthing clinic and/or hospital, or by the primary attending medical professionals, and delivered to the storage facility or to the customer for long-term storage. Alternatively, an intermediary service step can occur whereby an intermediate team receives cryo-preserved blood samples from the hospital and/or medical clinic and/or birthing location and this team performs the preservation and storage-sealing steps and delivers the completed stored samples to the requesting parent and/or guardian, and/or to the representative(s) of same.

Example 19

A preferred embodiment of the business method according to the invention enables a parent of a soon-to-be child to browse to a web-site that offers the service according to the invention. The requesting parent orders the taking of sample, and pre-pays for the preservation and long-term storage of the stem cells. In alternative embodiments of the invention the processing materials can include an address label so that the technician's mailing of a completed stored sample can be made directly to the requesting parent. Additionally, the delivery can be by courier service or mailing service that provides careful tracking of the delivery for greater security.

Example 20

Figure 27:
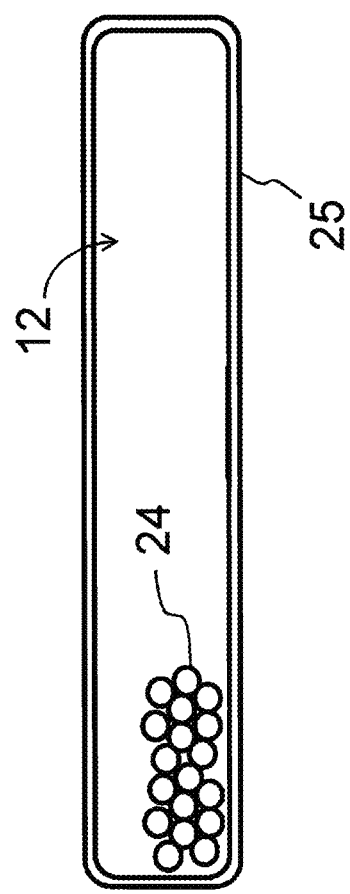
FIG. 27 illustrates a stem-cell storage container according to an embodiment of the invention.
Figure 28B:
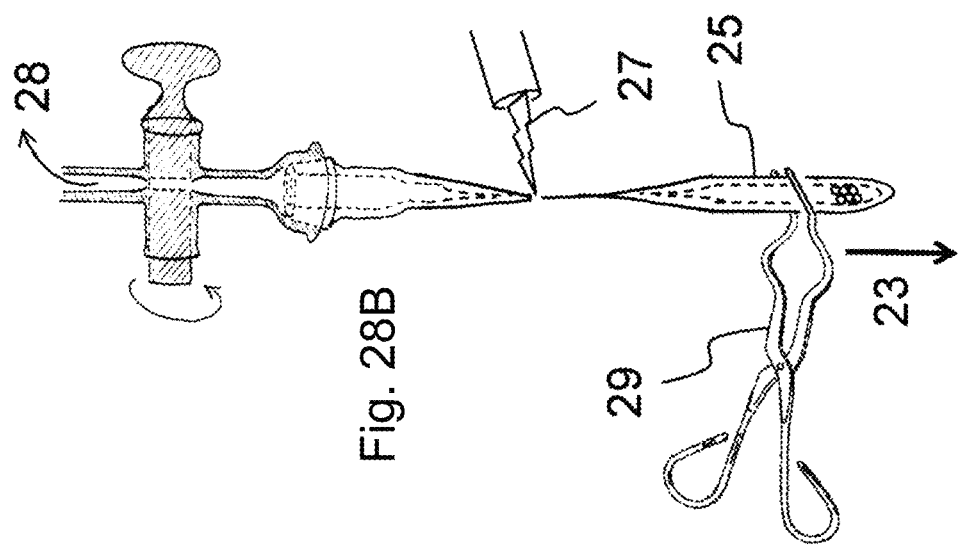
FIG. 28B illustrates a flame-off step to create a sealed, glass ampule having a specialized gaseous environment within.
Figure 28A:
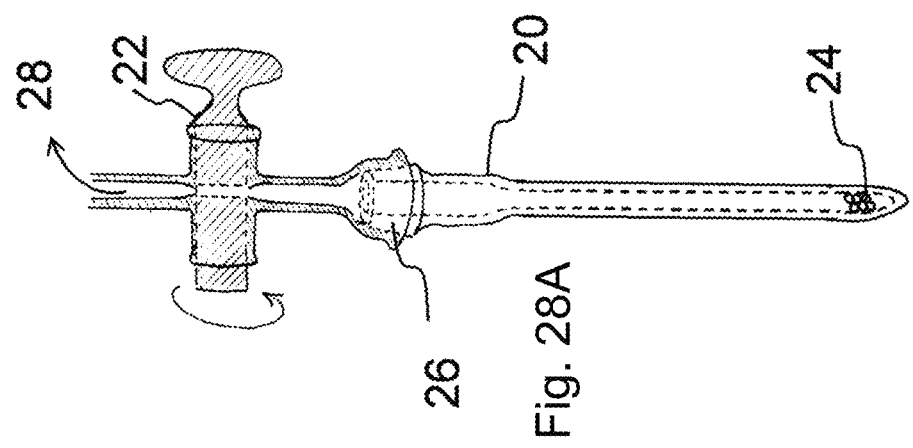
FIG. 28A illustrates a glass flame-off pipette containing stem cells according to an embodiment.
Figure 29:
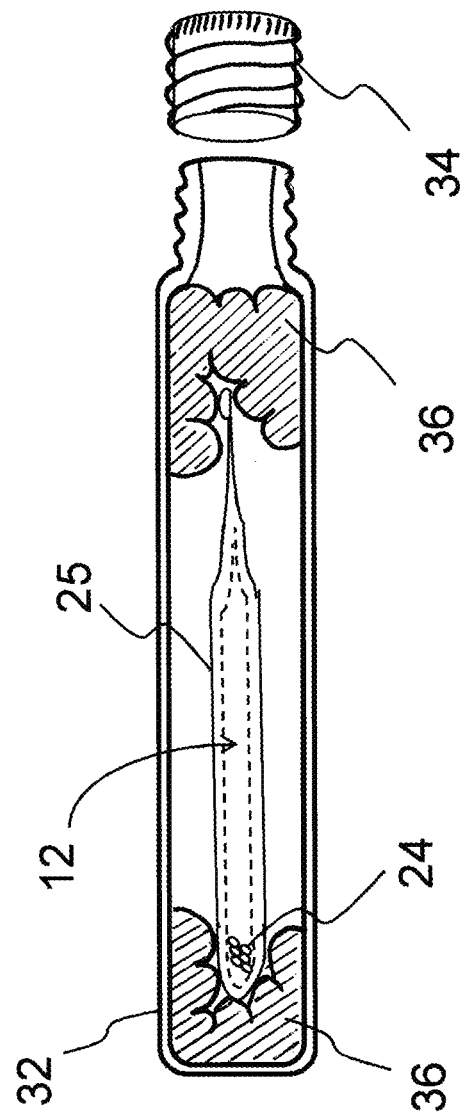
FIG. 29 illustrates a two-layer storage container according to an embodiment, wherein an airtight, permanently sealed ampule is located within an outer storage cylinder.

Embodiments of the invention can be further illustrated with reference to the Figures. Referring to FIG. 27, a container 25, which can be, for example, a plastic, glass or metal ampule or vial, contains preserved stem cells 24, immediately surrounded by a specialized environment 12, which environment can be, without limitation, a vacuum, a nitrogen gas, a gas mixture low in oxygen or devoid of oxygen, or a denser medium, such as a non-reactive plastic, or a preservative gel or other preserving medium. An ampule with a relative vacuum or low oxygen environment can be created as in FIG. 28A, wherein a glass flame-off pipette 22 containing stem cells 24, is located adjacent a stopcock 22 in a glass vacuum rack, with the glass pipette 22 being sealably connected by a greased, ground-glass stopper/flange 26. A vacuum 28 can be exerted (by a vacuum pump or cryotrap) through a conduit in the stopcock 22 to pull air and/or oxygen out of the pipette 22. Referring to FIG. 28B, the flame-off step is accomplished while a vacuum is being exerted (or a non-oxygen environment maintained), with the pipette held by tongs 29 as a torch flame 27 heats the pipette above the stored stem cells and then the melted portion of the pipette is stretched in a downward direction 23 to pull the melting glass closed at a narrow waist region. At this narrow waist point, after melting the tube closed, the glass can rapidly cool after removal of the flame 27 and the glass waist easily snapped to form ampule 25. A two-layer storage container according to an embodiment is illustrated in FIG. 29, wherein an airtight, permanently sealed ampule 25 containing stem cells 24 in the presence of a vacuum or nitrogen environment (or inert gas, or protective medium) 12 is located with an outer storage cylinder 32 having a screw cap 34, and with cotton wadding 36 further protecting the ampule 25.

FIG. 21 illustrates a succession of web pages or web screens that can appear according to an embodiment as part of the business method of providing an offer to a potential customer and the recording of order information and completion of the ordering transaction, wherein: a first business offering web page 2101 can present to the customer a choice of obtaining a description of services and/or a hyperlink to begin an order; a subsequent web page 2102 can include data-entry (or text-entry) windows 2104, which can include pull-down data selection windows (or menus of participating professionals, hospitals and clinics), for the customer to enter identifying and transaction information, such as but not limited to customer name and address, physician, hospital or clinic and/or expected birth date (or estimated sampling procedure date); a further secondary screen 2103 containing level of service choices 2106 (e.g., an inexpensive customer option can include simplest sampling/extraction/storage method, information storage and simple ampule sent to customer, whereas a more expensive option may include an expensive ampule, expensive sampling method, more elaborate and/or complete storage information and record, dual storage in safe-deposit box with a partner bank and in an ampule sent to the customer) a further secondary screen 2105 providing cost, invoice and/or payment information (for example, without limitation, an initial order fee, a specimen preparation fee, a storage container fee, shipping fees and, if the SSP Company is providing custodial storage, an annual storage fee); a further screen 2107 providing legal terms, which screen can include an interactive button to register customer's agreement to the legal terms (such as, without limitation, providing notice to the child at age of majority); and, inter alia, a further page 2108 that can include an interactive button to cause the order to be generated, and/or to initiate the processing of the submitted order.

FIG. 19 illustrates business steps according to another embodiment, wherein: at step 1901 a customer places an order; at step 1902 the order information is received and/or registered and/or recorded; at step 1903 the order information is matched against a database listing 1904; at step 1905 a service order is generated, which can be an automated step; at step 1906 a service order memo is created in email and or printed (in which fields are automatically filled in from the order information and/or the database information extracted in correspondence to the order information. The memo can read as follows, or in similar fashion:

"Dear <<SERVICE PROVIDER>> Please carry out standard procedure <<STORAGE I>> for customer <<XYZ>>. Attached are procedure protocols, specimen mailers and payment details. Sincerely, <<SSP Company>>"

At step 1907 the medical procedure is specified from a rule-based software engine that links the customer information and desired location for the procedure to appropriate and available protocols that are stored and indexed in the SSP Company database (which can include specific protocols for the blood and/or tissue sampling, stem cell extraction, cell freeze-drying, preservation and ampule storage), a mailer specification and label are generated, and payment to the service provider is detailed and scheduled; and step 1908 is transmission of the completed service order to the medical professional. Steps 1906, 1907 and 1908 can be automated.

Figure 30:
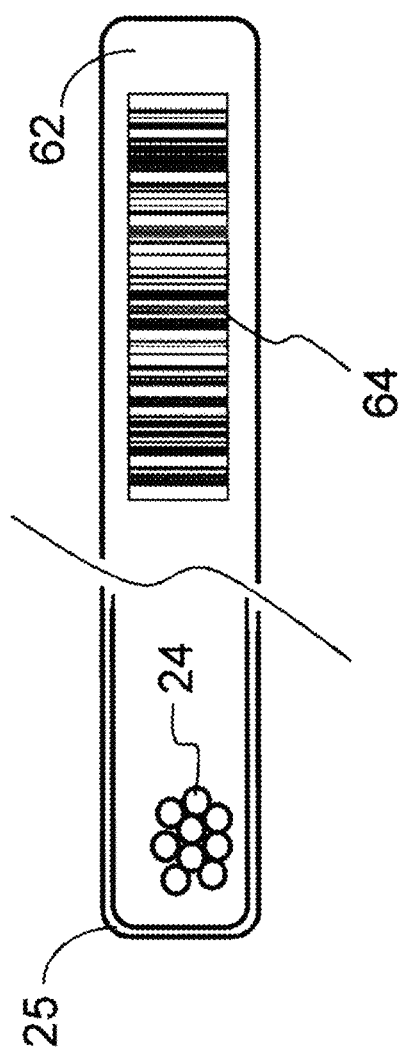
FIG. 30 illustrates a storage ampule upon which is permanently affixed a data component, according to an embodiment.

FIG. 30 illustrates a storage ampule 25 containing stem cells 24 having a covering layer 62 upon which is permanently affixed a data component 64, which data component 64 can be, for example, without limitation, bar code, optical storage, microfiche or other information record.

Example 21

Figure 31:
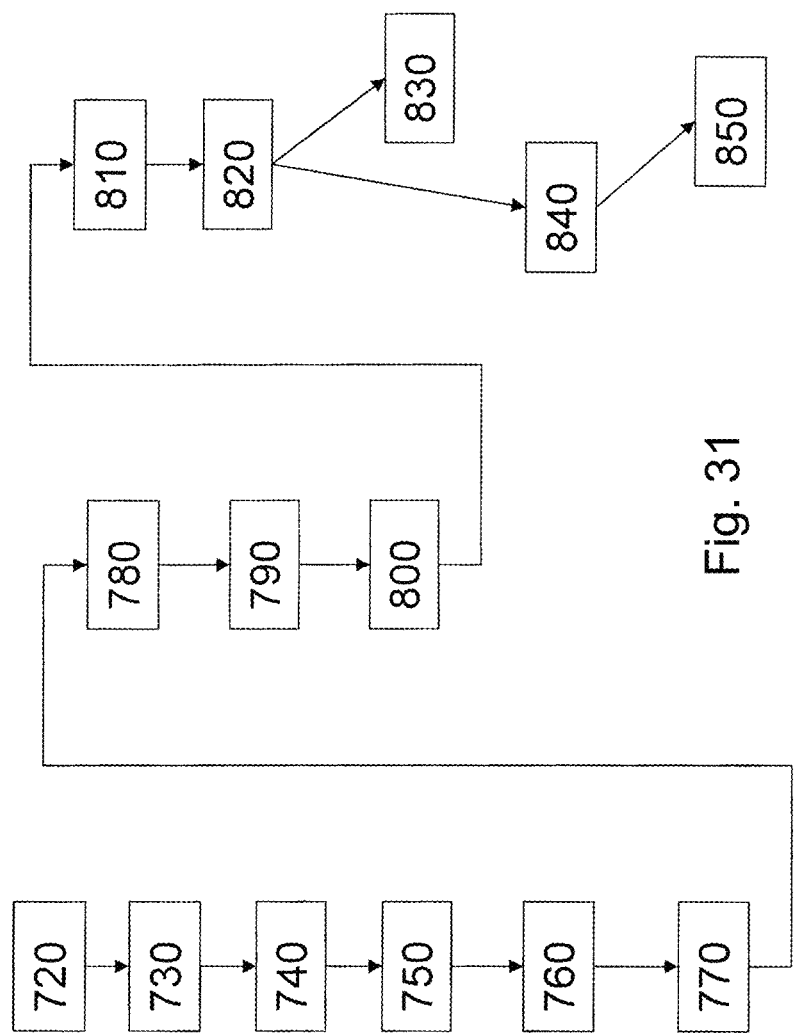
FIG. 31 illustrates a sequence of business steps according to an embodiment of the invention.

A further embodiment provides another example, illustrated by reference to FIG. 31, of a sequence of business steps according to the invention. FIG. 31 generally shows a flow chart describing a Web-based ordering process that is connected to automated generation of service-order that direct the steps of performing medical service steps, packaging and delivering storage containers to a storage site or to a customer; and/or delivering to the customer physical or digital keys to access the storage site, and/or code-release keys to initiate physical delivery of the stored vial to the customer. In more detail, the following steps are illustrated in FIG. 31. At step 720, a customer accesses a web site that offers the storage service or storable stem-cell product. At step 730, the customer orders services on the web site, such as, for example, providing medical professional and hospital/clinic information, providing dates, choosing level of service, entering data or meta-data to be included later in (or on) the storage container. This information can include names, dates, parents' DNA data, parents' medical history, inter alia, as well as information that may be subsequently and automatically pulled from other 3rd party databases through the Internet in response to information entered by the customer. At step 740, the customer pre-pays for extraction and storage (such as, for example, paying by credit card, or paying by pass-through billing to an obstetrician and/or through hospital and/or clinic fees). At step 750, the customer agrees to a binding contract (including, without limitation, a legal electronic signature, a waiver concerning liability, and/or the customer expressly assuming risk and liability on behalf of the minor child). At step 760, the SSP company server connects the customer's order information to a SSP company database or to one or more $3^{rd}$-party databases to obtain additional data or information to be used in generating a service order and/or used in subsequent formation and delivery of the storage method and service, such as, without limitation, information about procedures, locations, practitioners, hospitals, clinics, regulations, materials, storage facilities, banks, costs, risks, re-infusion, probabilities, service delivery, postal delivery, scientific data, storage containers and other information related to the customer-provided information and/or related to information needed for the service order. Typically, this data will be pulled from the SSP company and 3rd party databases by software program routines that automatically generate the service order; some of this information can be independent of the information provided by the customer's order entry, while other information can be dependent upon the customer's order entries. At step 770, the company software automatically generates a service order to participating professionals, hospitals, clinics and/or other service providers. At step 780, the SSP company software transmits electronically the Service Orders and portion of prepayment to practitioners, hospitals and clinics (optionally including a preaddressed postal or courier mailer envelope that can be subsequently used by the medical professional(s) to send the sampled and stored stem cells directly to a chosen storage facility or to the customer). At step 790, the medical and preservation services are performed by the professional practitioners in the hospital or clinic (for example, without limitation the umbilical cord is sectioned, blood extracted, stem cells extracted, stem cells preserved, stem cells stored in a storage container, and the container labeled with data and/or code tracking information). At step 800, data is entered by medical professionals, converted and/or transferred automatically onto the data component that is to be stored with the stored stem cells (such as, for example, information about the child/patient, the birth event, the sampling, extraction and preservation procedures. At step 810 the data component is merged with the storage container, such as by an automated labeling procedure. At step 820, the storage container is packaged in a mailer, which can be a mailer that has been preaddressed to the customer or to a centralized storage facility (such as described at step 780 above). At step 830, the mailer is sent/delivered to the customer, such as by U.S. postal service or by a courier service, and/or, at step 840, the package can be sent to a centralized storage facility or to a $3^{rd}$-party storage location, such as a safety-deposit box in a bank. At step 850, a code or key can be sent to the customer allowing later recovery from the storage facility or safety deposit box (where the code can be a digital password that allows the customer to signal a storage facility to automatically ship the stored sample to the customer or to another 3rd party).

Figure 32:
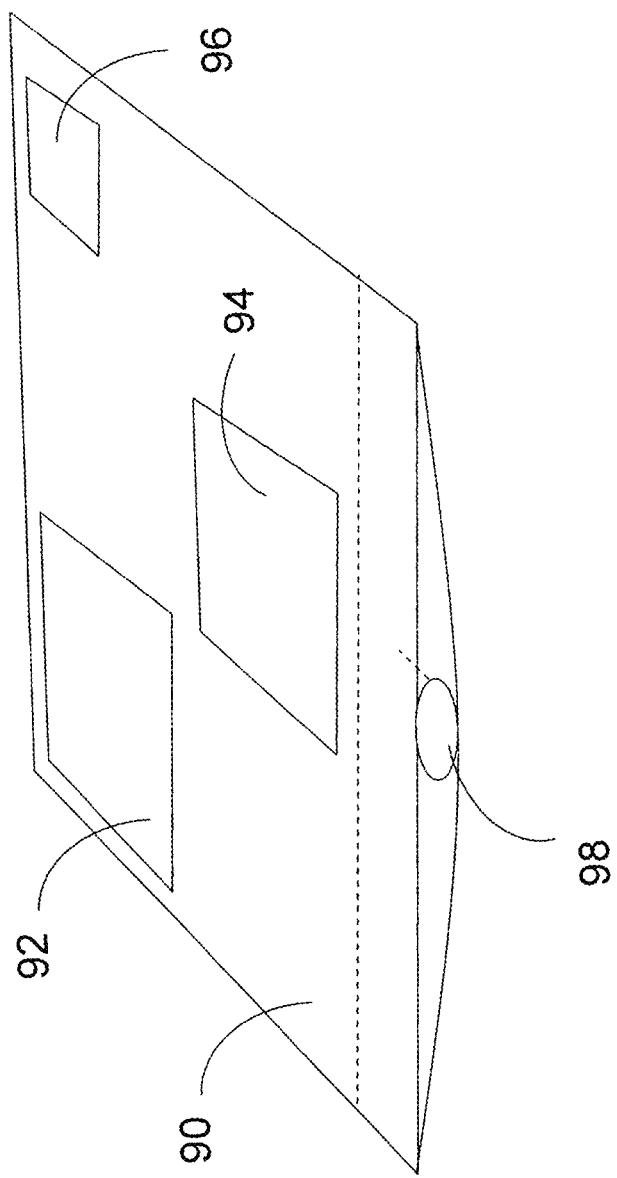
FIG. 32 illustrates a specialized transmittal envelope according to an embodiment of the invention.

FIG. 32 shows a transmittal envelope 90 that is especially suited and/or designed for a particular storage container 98 and for routing by addressing 94 to a particular storage facility, whereby the transmittal envelopes bear prepaid postage % and sufficient identifying coding 92 so that the envelopes can be automatically manipulated by robotic handling, including being processed, stored and later retrieved and reshipped to an end-user customer based on the information in the exterior coding 92. In the storage facility, automated storage methods can include providing sorting, processing, aligning and storage placement machinery wherein the specialized envelopes are stored efficiently and compactly in storage carousels and/or other automated containers that allow machine access, deposit and retrieval and automated reshipment based on the storage facility receiving a password-protected, storage-release directive from an end-user customer.

What has been described above includes examples of the invention. It is, of course, not possible to describe every conceivable combination of components or methodologies for purposes of describing the subject invention, but one of ordinary skill in the art may recognize that many further combinations and permutations of the invention are possible. Accordingly, the invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

While the present invention has been described in conjunction with one or more preferred embodiments, one of ordinary skill, after reading the foregoing specification, will be able to effect various changes, substitutions of equivalents, and other alterations to the systems and methods set forth herein. It is therefore intended that the patent protection granted hereon be limited only by the appended claims and equivalents thereof.

What is claimed is:

1. A web-based and computer-implemented system comprising:
    one or more processors residing on an application server, at least one processor electronically connected to a memory storing non-generic, specialized machine-readable instructions;
    a database electronically connected to at least one processor, the database configured to store information about a plurality of medical or biomedical service providers that offer medical or biomedical services, wherein the offered biomedical services are related to a plurality of functional biomedical objectives, and wherein each functional biomedical objective is related in the database to one or more medical or biomedical service providers;
    wherein one or more of the non-generic, specialized instructions instruct the one or more processor to perform the following:
        host one or more web pages displaying information about one or more medical or biomedical services;
        allow a customer to input information to the system relative to the customer;
        select a medical or biomedical service that is related to a functional objective for a customer accessing the system, and
    wherein the system is configured such that a customer accessing the application server through an Internet connection causes the system software to perform the steps of:
    determining a user-specified goal based on user input about choice of a studied-system domain, the studied system having components and dynamic relationships between components, and further user settings from the group consisting of goal type and sub-goal type, budget, deadline and relevant domain database source,
    assembling, via a knowledge-base-assembly software module responsive to a user's input choice of studied-system, a knowledge-base-assembly comprising a graph-based, causal-network computer model related to at least a sub-system of the studied system,
    enabling and constraining forward simulation of the graph-based, causal-network computer model, by a device, to reveal effects from upstream perturbations on downstream behavior in the studied system by using variables from the group comprising time-dynamic data, energy parameters, material balances and thermodynamic variables, said thermodynamic variables being from the group comprising temperature, Gibbs free energy, enthalpy, entropy and electrical potential,
    constructing automatically, by a device, a research goal statement based on the user-specified goal selection, the statement having parameter settings that enable gathering expert information from a studied-system domain manual related to the components and relationships between components in the studied system,
    transforming, by a device, the research goal statement into a declarative statement of information that is needed to reduce uncertainty in the knowledge assembly by evaluating a studied-system knowledge model in view of the research goal statement and by analyzing the highest probability path to reduce a gap in information that corresponds with uncertainty in the knowledge assembly;
    selecting, automatically by a computer device, one or more research services, based on the services providing procedures or protocols likely to produce experimental results to reduce uncertainty in the knowledge assembly,
    wherein the software-directed steps relate the customer's input information to information about the biomedical services and retrieve from the database information sufficient to complete and deliver a standard service order.

2. The system of claim 1, wherein at least one of said functional biomedical objectives comprises at least one of the group of (a) characterizing normal system function, (b) one or more of detecting and characterizing abnormal system function and detecting and characterizing system dysfunction, (c) one or more of testing and finding modes for correcting system function and testing and finding adaptive and protective modes for system function, and (d) optimizing modes for correcting, adapting or protecting system function.

3. The system of claim 1, wherein at least one of the functional biomedical objectives comprises a biomedical service product comprising the performance of a biomedical service protocol by a third-party vendor subsequent to and in response to the service order.

4. The system of claim 3, wherein the biomedical service product is a biomedical research service product comprising the performance of a biomedical research service protocol by a third-party vendor subsequent to and in response to the service order.

5. A computer-based and internet-based biomedical service business method comprising the steps of:
(a) providing one or more processors residing on an application server, at least one processor electronically connected to a database and accessible to customers via an Internet connection;
(b) storing information in the database about a plurality of biomedical service providers offering biomedical services, the offered biomedical services being related to a plurality of functional biomedical objectives, and wherein each functional biomedical objective is related in the database to one or more biomedical service providers;
(c) communicating, by a computer device, information about the service providers to potential customers;
(d) receiving, by a computing device, from a customer, input information to the application server relative to the customer;
(e) initiating, by a computer device, a query based on input information from the customer; comprising the performance of a biomedical service protocol by a third-party vendor subsequent to and In response to the service order;
(f) receiving, by a computer device, information from one or more customers with respect to a customer's choosing of a service of a service provider;
(g) relating, by a computer device, the customer's input information to information about the biomedical services by the further steps of:
(g.1) determining a user-specified goal based on user input about choice of a studied-system domain, the studied system having components and dynamic relationships between components, and further user settings from the group consisting of goal type and sub-goal type, budget, deadline and relevant domain database source,
(g.2) assembling, via a knowledge-base-assembly software module responsive to a user's input choice of studied-system, a knowledge-base-assembly comprising a graph-based, causal-network computer model related to at least a sub-system of the studied system,
(g.3) enabling and constraining forward simulation of the graph-based, causal-network computer model, by a device, to reveal effects from upstream perturbations on downstream behavior in the studied system by using variables from the group comprising time-dynamic data, energy parameters, material balances and thermodynamic variables, said thermodynamic variables being from the group comprising temperature, Gibbs free energy, enthalpy, entropy and electrical potential,
(g.4) constructing automatically, by a device, a research goal statement based on the user-specified goal selection, the statement having parameter settings that enable gathering expert information from a studied-system domain manual related to the components and relationships between components in the studied system,
(g.5) transforming, by a device, the research goal statement into a declarative statement of information that is needed to reduce uncertainty in the knowledge assembly by evaluating a studied-system knowledge model in view of the research goal statement and by analyzing the highest probability path to reduce a gap in information that corresponds with uncertainty in the knowledge assembly; and
(g.6) selecting, automatically by a computer device, one or more research services, based on the services providing procedures or protocols likely to produce experimental results to reduce uncertainty in the knowledge assembly;
(h) retrieving from the database, by a computer device, information sufficient to complete and deliver a standard service order;
(i) completing, by a computer device, the service order; and
(j) outputting, by a computer device, the service order and delivering, by a computer device, the service order.

6. The method of claim 5, wherein said functional biomedical objectives comprise at least one of the group of (a) characterizing normal system function, (b) one or more of detecting and characterizing abnormal system function and detecting and characterizing system dysfunction, (c) one or more of testing and finding modes for correcting system function and testing and finding adaptive and protective modes for system function, and (d) optimizing modes for correcting, adapting or protecting system function.

7. The method of claim 5, wherein at least one of the functional biomedical objectives comprises a biomedical service product comprising the performance of a biomedical service protocol by a third-party vendor subsequent to and in response to the service order.

8. The method of claim 7, wherein the biomedical service product is a biomedical research service product comprising the performance of a biomedical research service protocol by a third-party vendor subsequent to and in response to the service order.

9. The method of claim 5, wherein the steps of (h)-(j) further comprise the steps of
detecting an order on at least one of a computer and the application server from the customer for at least one of the functional biomedical objectives,
connecting or relating via the database the customer's order to information about at least one biomedical service provider offering a biomedical service capable of accomplishing the at least one of the functional biomedical objectives,
retrieving, by a computing device, from the database information sufficient to complete a service order to the at least one biomedical service provider who is offering a biomedical service capable of accomplishing the at least one of the functional biomedical objectives corresponding to the customer's order, and
notifying the at least one biomedical service provider of the customer's order by completing a service order, by a computer device, and delivering the service order, by a computing device, to the at least one biomedical service provider.

* * * * *